(12) United States Patent
Bonutti et al.

(10) Patent No.: US 12,014,289 B2
(45) Date of Patent: Jun. 18, 2024

(54) ARTIFICIAL INTELLIGENCE AND/OR VIRTUAL REALITY FOR ACTIVITY OPTIMIZATION/PERSONALIZATION

(71) Applicant: P Tech, LLC, Effingham, IL (US)

(72) Inventors: Peter M. Bonutti, Manalapan, FL (US); Justin E. Beyers, Effingham, IL (US); Tonya M. Bierman, Dieterich, IL (US)

(73) Assignee: P TECH, LLC, Manalapan, FL (US)

( * ) Notice: Subject to any disclaimer, the term of this patent is extended or adjusted under 35 U.S.C. 154(b) by 0 days.

(21) Appl. No.: 17/395,177

(22) Filed: Aug. 5, 2021

(65) Prior Publication Data

US 2021/0365815 A1  Nov. 25, 2021

Related U.S. Application Data

(63) Continuation of application No. 16/118,025, filed on Aug. 30, 2018, now Pat. No. 11,687,800.
(Continued)

(51) Int. Cl.
*G06N 5/04* (2023.01)
*A61B 3/00* (2006.01)
(Continued)

(52) U.S. Cl.
CPC ............ *G06N 5/04* (2013.01); *A61B 3/0025* (2013.01); *A61B 3/005* (2013.01); *A61B 5/021* (2013.01); *A61B 5/163* (2017.08); *A61B 5/4809* (2013.01); *A61B 5/6817* (2013.01); *A61N 1/36514* (2013.01); *G06N 20/00* (2019.01); *G06T 7/0012* (2013.01); *G08B 21/02* (2013.01); *G08B 21/0423* (2013.01); *G08B 21/043* (2013.01); *G08B 21/182* (2013.01);
(Continued)

(58) Field of Classification Search
CPC ........ G06N 5/04; G06N 20/00; A61B 3/0025; A61B 3/005; A61B 5/021; A61B 5/163; A61B 5/4809; A61B 5/6817; A61B 5/0059; A61B 5/6815; A61N 1/36514; G06T 7/0012; G06T 2207/10048; G06T 2207/30041; G08B 21/02; G08B 21/0423; G08B 21/043; G08B 21/182; G08B 25/016; G08B 31/00; G16H 20/10; G16H 20/30; G16H 20/60; G16H 40/67; G16H 50/20
See application file for complete search history.

(56) References Cited

U.S. PATENT DOCUMENTS 5,589,818 A * 12/1996 Queen ............... G08B 25/016
                                                      379/49
5,722,418 A *  3/1998 Bro ..................... H04M 11/00
                                                      128/920
(Continued)

FOREIGN PATENT DOCUMENTS

CN       205514564 U  *  8/2016
WO       2016018856 A1    2/2016

OTHER PUBLICATIONS

International Search Report and Written Opinion for PCT/US2018/48892, Dec. 31, 2018, 17 pages.

*Primary Examiner* — Mohamed Barakat
*Assistant Examiner* — Rufus C Point
(74) *Attorney, Agent, or Firm* — Stinson LLP

(57) ABSTRACT

Optimizing and/or personalizing activities to a user through artificial intelligence and/or virtual reality.

23 Claims, 39 Drawing Sheets

Related U.S. Application Data

(60) Provisional application No. 62/552,096, filed on Aug. 30, 2017, provisional application No. 62/552,091, filed on Aug. 30, 2017.

(51) Int. Cl.

| | |
|---|---|
| *A61B 5/00* | (2006.01) |
| *A61B 5/021* | (2006.01) |
| *A61B 5/16* | (2006.01) |
| *A61N 1/365* | (2006.01) |
| *G06N 20/00* | (2019.01) |
| *G06T 7/00* | (2017.01) |
| *G08B 21/02* | (2006.01) |
| *G08B 21/04* | (2006.01) |
| *G08B 21/18* | (2006.01) |
| *G08B 25/01* | (2006.01) |
| *G08B 31/00* | (2006.01) |
| *G16H 20/10* | (2018.01) |
| *G16H 20/30* | (2018.01) |
| *G16H 20/60* | (2018.01) |
| *G16H 40/67* | (2018.01) |
| *G16H 50/20* | (2018.01) |

(52) U.S. Cl.
CPC ........... *G08B 25/016* (2013.01); *G08B 31/00* (2013.01); *G16H 20/10* (2018.01); *G16H 20/30* (2018.01); *G16H 20/60* (2018.01); *G16H 40/67* (2018.01); *G16H 50/20* (2018.01); *A61B 5/0059* (2013.01); *A61B 5/6815* (2013.01); *G06T 2207/10048* (2013.01); *G06T 2207/30041* (2013.01)

(56) References Cited

U.S. PATENT DOCUMENTS

| | | | |
|---|---|---|---|
| 7,034,691 B1 | 4/2006 | Rapaport et al. | |
| 8,725,243 B2* | 5/2014 | Dilorenzo | G16H 20/10 |
| | | | 600/544 |
| 8,868,172 B2* | 10/2014 | Leyde | G16H 20/10 |
| | | | 600/544 |
| 8,879,813 B1 | 11/2014 | Solanki | |
| 8,885,901 B1 | 11/2014 | Solanki | |
| 8,958,882 B1* | 2/2015 | Hagedorn | A61B 5/6803 |
| | | | 607/45 |
| 9,002,085 B1 | 4/2015 | Solanki | |
| 9,008,391 B1 | 4/2015 | Solanki | |
| 9,044,188 B2* | 6/2015 | DiLorenzo | A61N 1/37258 |
| 9,143,569 B2* | 9/2015 | Mensinger | A61B 5/0022 |
| 9,622,675 B2* | 4/2017 | Leyde | A61B 5/4094 |
| 10,371,945 B2* | 8/2019 | Samec | G02B 21/0032 |
| 10,664,569 B2* | 5/2020 | McMahon | G16H 70/00 |
| 10,796,549 B2* | 10/2020 | Roberts | A61B 5/486 |
| 2003/0112144 A1* | 6/2003 | Campman | G08B 21/0453 |
| | | | 340/384.1 |
| 2004/0122702 A1* | 6/2004 | Sabol | G06Q 10/10 |
| | | | 706/45 |
| 2007/0075965 A1 | 4/2007 | Huppi et al. | |
| 2007/0136102 A1 | 6/2007 | Rodgers | |
| 2007/0150025 A1* | 6/2007 | Dilorenzo | G16H 50/30 |
| | | | 607/45 |
| 2009/0121930 A1* | 5/2009 | Bennett | G08B 25/016 |
| | | | 342/357.55 |
| 2009/0177068 A1* | 7/2009 | Stivoric | A61B 5/0022 |
| | | | 600/365 |
| 2009/0187389 A1* | 7/2009 | Dobbins | G06F 3/011 |
| | | | 715/757 |
| 2009/0234199 A1 | 9/2009 | Takahashi et al. | |
| 2011/0213222 A1* | 9/2011 | Leyde | A61B 5/0031 |
| | | | 600/301 |
| 2011/0238478 A1 | 9/2011 | Gottfurcht et al. | |
| 2013/0095459 A1* | 4/2013 | Tran | G09B 19/00 |
| | | | 434/247 |
| 2013/0217986 A1 | 8/2013 | Lengyel | |
| 2013/0339043 A1 | 11/2013 | Bakar | |
| 2014/0052465 A1 | 2/2014 | Madan et al. | |
| 2014/0100464 A1 | 4/2014 | Kaleal et al. | |
| 2014/0156308 A1 | 6/2014 | Dacadoo | |
| 2014/0213857 A1* | 7/2014 | Teller | A61B 5/4809 |
| | | | 600/595 |
| 2014/0245783 A1 | 9/2014 | Proud | |
| 2014/0247135 A1 | 9/2014 | Proud | |
| 2014/0247145 A1 | 9/2014 | Proud | |
| 2014/0310013 A1 | 10/2014 | Ram et al. | |
| 2015/0110368 A1 | 4/2015 | Solanki | |
| 2015/0110372 A1 | 4/2015 | Solanki | |
| 2015/0112606 A1 | 4/2015 | He et al. | |
| 2015/0294086 A1* | 10/2015 | Kare | G16H 20/70 |
| | | | 705/2 |
| 2016/0000324 A1 | 1/2016 | Rege et al. | |
| 2016/0034671 A1 | 2/2016 | Hyde et al. | |
| 2016/0142407 A1 | 5/2016 | Chun et al. | |
| 2016/0147959 A1 | 5/2016 | Mariottini | |
| 2016/0235323 A1* | 8/2016 | Tadi | A61B 5/0006 |
| 2017/0136289 A1* | 5/2017 | Frank | A63B 22/025 |
| 2017/0169689 A1* | 6/2017 | Vagelos | G08B 25/016 |
| 2017/0289704 A1* | 10/2017 | Frederiksen | G16H 40/63 |
| 2017/0290528 A1* | 10/2017 | Ternes | G16H 40/67 |
| 2018/0001184 A1* | 1/2018 | Tran | A63B 60/46 |
| 2018/0122511 A1* | 5/2018 | Apte | G16H 50/20 |
| 2018/0193589 A1* | 7/2018 | McLaughlin | G06F 3/016 |
| 2018/0279911 A1* | 10/2018 | Lucisano | G08B 3/10 |
| 2019/0065970 A1* | 2/2019 | Bonutti | A61B 5/6817 |
| 2019/0125227 A1* | 5/2019 | Koya | A61N 1/3606 |
| 2019/0343456 A1 | 11/2019 | Kahlert et al. | |
| 2020/0410891 A1* | 12/2020 | Baeuerle | G16H 20/70 |

* cited by examiner

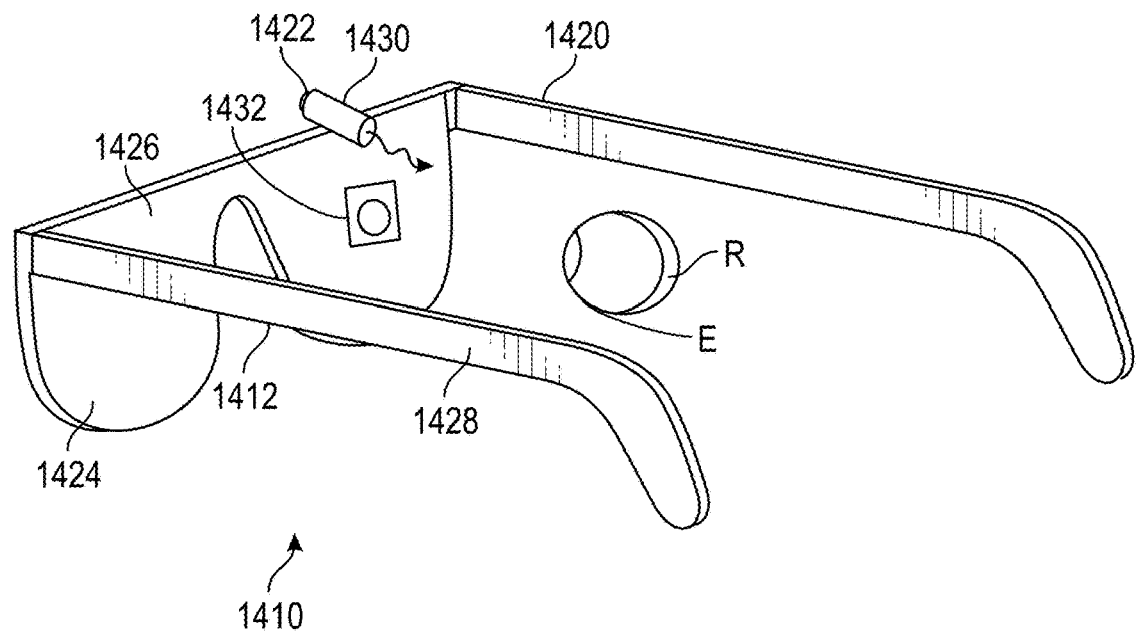
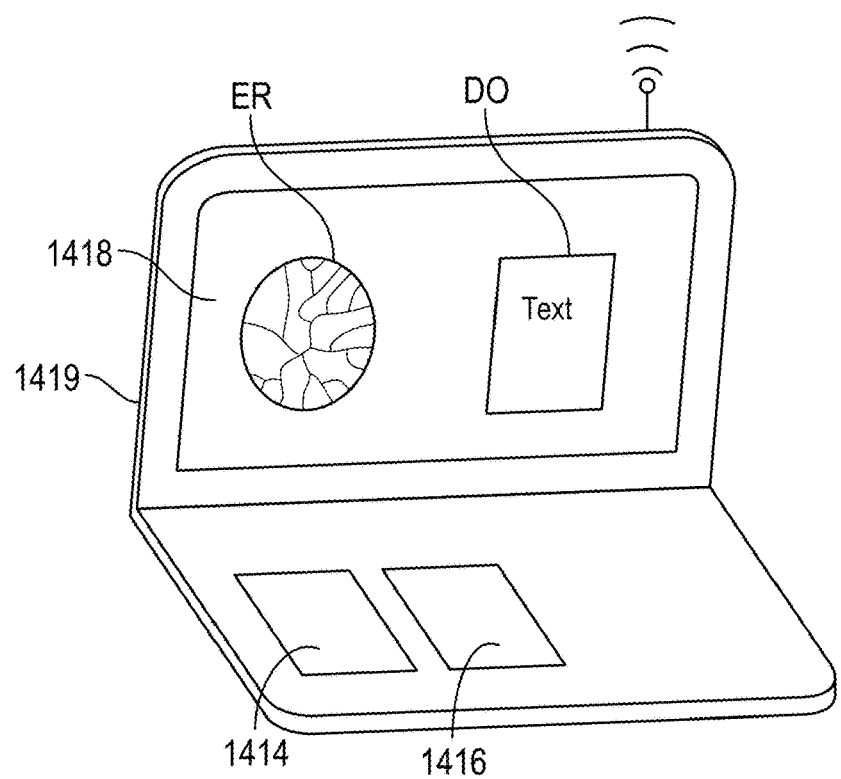
FIG. 24

ARTIFICIAL INTELLIGENCE AND/OR VIRTUAL REALITY FOR ACTIVITY OPTIMIZATION/PERSONALIZATION

CROSS-REFERENCE TO RELATED APPLICATIONS

The present application is a continuation of U.S. patent application Ser. No. 16/118,025, filed Aug. 30, 2018, which claims the benefit of U.S. Provisional Application No. 62/552,096, filed Aug. 30, 2017, and which claims the benefit of U.S. Provisional Application No. 62/552,091, filed Aug. 30, 2017, the entireties of which are hereby incorporated by reference.

FIELD OF THE DISCLOSURE

The field of the disclosure relates generally to artificial intelligence and virtual/augmented reality, and more specifically, to methods and systems for optimizing/personalizing user activities through artificial intelligence and/or virtual reality.

BACKGROUND

Artificial intelligence (AI) is slowly being incorporated into the medical field. AI systems and techniques can be used to improve health services—both at the physician and patient levels, used to improve the accuracy of medical diagnosis, manage treatments, provide real time monitoring of patients, and integrate the different health providers and health services together—all while decreasing the costs of medical services. However, some previous attempts to use artificial intelligence in medicine have failed. For example, IBM's Watson attempted to use artificial intelligence techniques for oncology therapy. Watson failed to help oncologic treatments because Watson was not a linear artificial intelligence dictated purely by logic and was unable to analyze variances in biologic functions at a variety of different levels.

BRIEF DESCRIPTION

In an aspect, a system includes a monitor device and an artificial intelligence (AI) system. The monitor device is configured to monitor one or more physical properties of a user. The AI system is configured to receive and analyze the monitored physical properties to generate one or more activity parameters optimized or personalized to the user. The AI system is configured to implement one or more artificial intelligence techniques such as predictive learning, machine learning, automated planning and scheduling, machine perception, computer vision, affective computing to generate one or more activity parameters optimized or personalized to a user.

In another aspect, a system includes a goggle device and a controller. The goggle device is configured to provide one or more images to a user of the system and perform at least one vision test on the user. The controller is configured to execute an algorithm for tracking at least one vision-related impairment of the user based on the vision test and/or enhancing the vision of the user based on the vision test.

In another aspect, a method of diagnosing diseases and assessing health is performed by retinal imaging or scanning. The pupil is dilated by, for example, dark glasses, and then the retina is imaged. In an embodiment, the image of the retina is evaluated by a computing device, a person, or both to glean information relating to not only health, but also emotional reactions, physiological reactions, etc.

In another aspect, optical imaging, especially of the retina, is used to obtain real-time feedback data, which can be analyzed by a computer, a person, or both to determine emotional response, pain, etc. This feedback data can be fed into a VR/AR program or otherwise used to determine a subject's emotional and/or physiological response to certain stimuli.

In still another aspect, optical imaging or scanning is used for continuous health monitoring. For example, continuous or regular imaging of the eye is used to track blood pressure. Reactions to a stimulus, such as exercise for example, could help doctors and could be utilized by a computer to automatically check for signs of disease and/or poor health in various areas. In an embodiment, findings are integrated with other systems, such as those used to collect medical data for example, to provide more accurate and/or comprehensive findings.

In yet another aspect, a retina is evaluated to allow a computer to make adjustments based on real-time user feedback. For example, if the person is playing a VR/AR game, a processor can use instantaneous feedback from the user to adjust difficulty, pace, etc.

In another aspect, alternate methods of measuring blood pressure and other health statistics are used for continual monitoring. In an exemplary and non-limiting embodiment, a wrist-wearable monitor or an earpiece monitor with a Doppler ultrasound imaging system is adapted to estimate blood pressure. In a preferred embodiment, continual retinal imaging and evaluation and health monitoring devices work in combination with a device to continuously measure blood pressure. In such an embodiment, a processor will preferably have access to any data gathered by retinal imaging and/or other health monitoring devices.

The features, functions, and advantages that have been discussed can be achieved independently in various embodiments or may be combined in yet other embodiments, further details of which can be seen with reference to the following description and drawings.

BRIEF DESCRIPTION OF THE DRAWINGS

FIG. 24 is a schematic illustration of a retinal evaluation system according to an embodiment.

Corresponding reference characters indicate corresponding parts throughout the drawings.

DETAILED DESCRIPTION

The systems and methods described herein, in an embodiment, enable the optimization and/or personalization of health-related tasks through artificial intelligence (AI). Aspects described herein also enable optimization and/or personalization in microclimate, robotics, management information systems, and the like.

Figure 1:
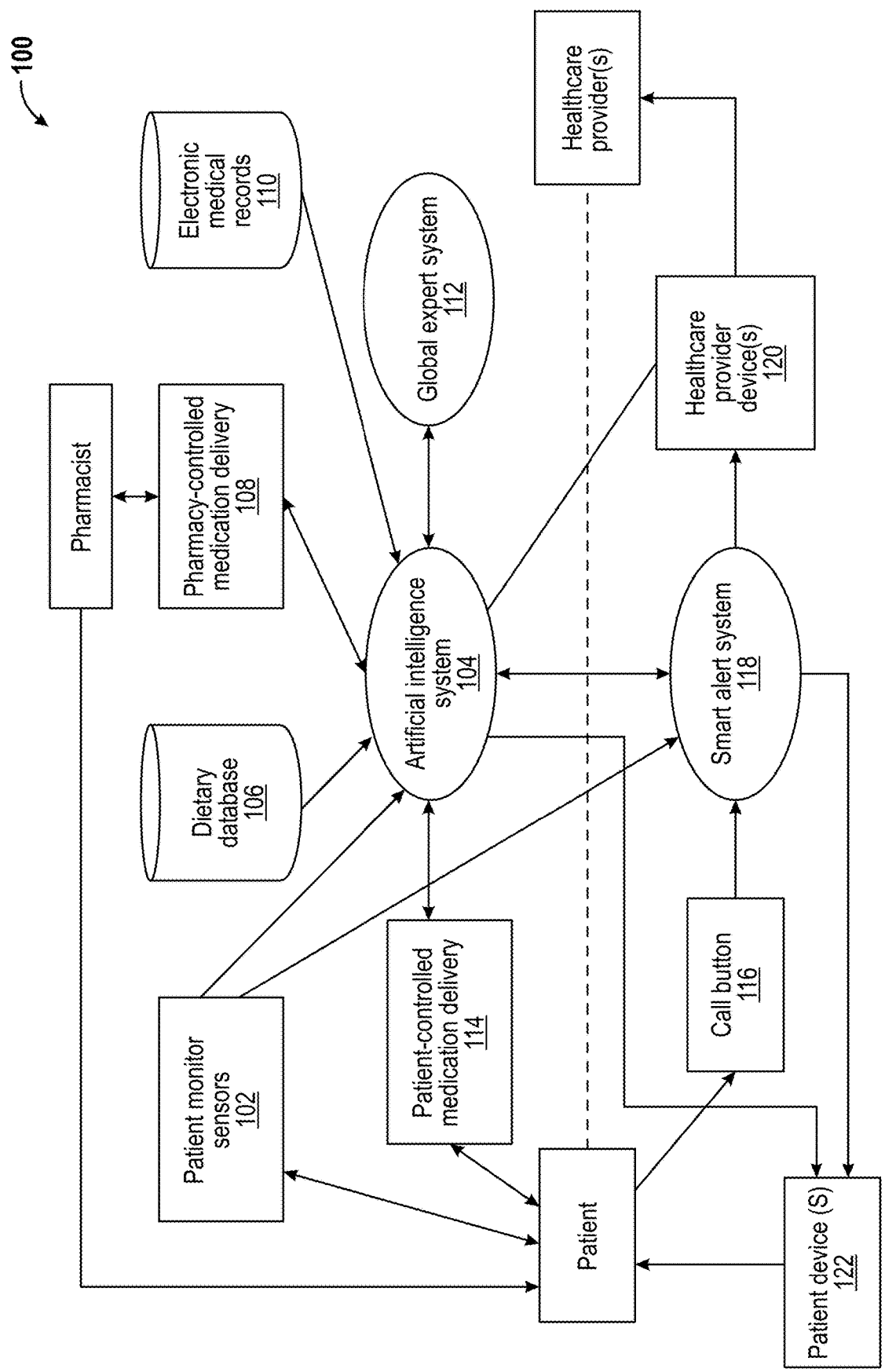
FIG. 1 is a block diagram illustrating an exemplary system and data flow according to an embodiment.

FIG. 1 is a block diagram illustrating an exemplary system 100 for optimizing and/or personalizing health-related tasks, for example. The system 100 includes one or more patient monitor sensors 102, an AI system 104, a dietary database 106, a pharmacy-controlled medication delivery subsystem 108, an electronic medical records database 110, a global expert system 112, a patient-controlled medication delivery subsystem 114, a call button 116, a smart alert system 118, one or more healthcare provider devices 120, and one or more patient devices 122. In an embodiment, system 100 enables automated planning and scheduling (e.g., AI planning) of strategies or action sequences for execution by healthcare providers and/or patients such that delivery of healthcare services is optimized (e.g., optimal for a healthcare provider and/or group of healthcare providers, optimal for the patient care and/or satisfaction, etc.) and/or personalized (e.g., personalized to needs/requirements of a healthcare provider and/or group of healthcare providers, personalized to needs/requirements of the patient, etc.).

The patient monitor sensors 102, the dietary database 106, the pharmacy-controlled medication delivery subsystem 108, the electronic medical records database 110, the global expert system 112, and the patient-controlled medication delivery subsystem 114 are electrically and/or communicatively coupled to the AI system 104. Additionally or alternatively, healthcare provider devices 120 and/or patient devices 122 are electrically and/or communicatively coupled to AI system 104. The patient monitor sensors 102, the AI system 104, and the call button 116 are electrically and/or communicatively coupled to the smart alert system 118. The smart alert system 118 is electrically and/or communicatively coupled to the healthcare provider devices 120 and the patient devices 122. In an exemplary and non-limiting embodiment, the electrical and/or communicative couplings described herein are achieved via one or more communications networks capable of facilitating the exchange of data among various components of AI system 100. For example, the one or more communications networks may include a wide area network (WAN) that is connectable to other telecommunications networks, including other WANs or portions of the Internet or an intranet, including local area networks (LANs) and/or personal area networks (PANs). The one or more communications networks may be any telecommunications network that facilitates the exchange of data, such as those that operate according to the IEEE 802.3 (e.g., Ethernet), the IEEE 802.11 (e.g., Wi-Fi™) and/or the IEEE 802.15 (e.g., Bluetooth®) protocols, for example. In another embodiment, the one or more communications networks are any medium that allows data to be physically transferred through serial or parallel communication channels (e.g., copper wire, optical fiber, computer bus, wireless communication channel, etc.).

The patient monitor sensors 102 are configured to sense physical properties associated with the patient. The patient monitor sensors 102 can be generally any type of biometric sensor that generates biometric data and may be positioned outside or inside the body of a patient. Exemplary sensors include, but are not limited to, contactless bed sensors such as the Murata SCA11H, activity trackers (e.g., wireless-enabled wearable devices available from Fitbit, Inc., etc.), smartwatches (e.g., the Apple® Watch available from Apple, Inc., etc.), smartphone computing devices, tablet computing devices, smart rings (e.g., MOTA® DOI SmartRing available from Mota Group, Inc., Token available from Tokenize Inc., etc.), smart glasses, smart contact lenses, video cameras, implants, retinal scanners, flexible sensors, surgical implants, medical implants, voice/sound input (e.g., microphones), accelerometers, goniometers, and like commercial or custom tracking devices with the ability to record and/or transmit patient metrics (e.g., distance walked or ran, calorie consumption, heartbeat, quality of sleep, movements, sleep patterns, blood pressure, pulse, sweat, skin resistance, etc.). Exemplary sensors further include, but are not limited to, existing sensors used in hospital monitoring systems, such as hospital records, pulse oximeters, retinal changes, implantable defibrillators, temperature, thermal gradients, changes in diet or food patterns (e.g., from dieticians), medication (e.g., from the pharmacy), test results from lab service (e.g., blood work and urinalysis) and the like. Additional exemplary sensors include, but are not limited to, devices configured to collect data relative to medications and/or exercise, such as motion patterns, eye movement, body temperature, core vs. peripheral breathing, shaking and/or tremors, heart rate, cardiac rhythms and/or arrhythmias, blood pressure, pulse, oximeters, respiration rate, diaphragm excursion, stride length, sleep patterns (e.g., EMGs, EEGs, etc.), oxygenation (e.g., pulse odometers), hair follicle movement and/or position change, lactic acidosis in muscles locally and/or systemically, sweat, thermal changes to skin and/or deep tissue, salinity or particles, blood flow, vasoconstriction, vasodilation, foot orthotic sensors on stride length, frequency, load, where load is applied, timing between steps, asymmetry in gait cadence and/or timing cadence, arm movement, pupillary and/or retinal response, retinal vascular changes, cheek movement (e.g., for retained air resistance, etc.), thermal gradients between one body part and another (e.g., quadriceps and chest or neck, etc.), blood flow between different body parts (e.g., neck and foot, etc.) such as measurements from laser flow sensors, ultrasonic sensors, acoustic sensors, electromagnetic field sensors, tension sensors, compression sensors, magnetic resonance imaging (MRI), positron emission tomography (PET), and the like. Further exemplary sensors include, but are not limited to, one or more aspects of a virtual reality system as further described herein. In an embodiment, a single patient monitor sensor 102 may provide a plurality of data points. In an embodiment, patient monitor sensors 102 transmit and/or provide data to other aspects of system 100 via wireless, radio frequency (RF), optical, and the like communications means. Further, if the sensor is implanted, the sensor can generate electricity by electromagnets, motion analysis and/or thermal changes. Moreover, the sensors are not limited to use with a patient and can be used in cellular testing, animal testing, and bacterial testing.

Accordingly, aspects of system 100, through the one or more patient monitors 102, enable patient properties such as biometric data, cellular data, biologic data, and non-biologic data to be collected and analyzed. This data can then be utilized by the AI system 104 to optimize and/or personalize health-related tasks, as described herein. The data collected can relate to any patient property such as body functions, organ function, cellular functions, and metabolic functions, for example. Moreover, aspects of system 100 are not limited to people and can be used for any biologic function. For example, aspects of system 100 can be used to analyze animal biologic functions and/or microbiologic functions. In all embodiments the capture of information could be done via wireless communication, or wired communication. The information could be uploaded to and stored in a central repository or processed on site.

The AI system 104 is configured to implement one or more artificial intelligence techniques (e.g., predictive learning, machine learning, automated planning and scheduling, machine perception, computer vision, affective computing, etc.) that optimize and/or personalize one or more aspects of monitoring, diagnosis, treatment, and prevention of disease, illness, injury, physical and/or mental impairments of the patient. In an embodiment, AI system 104 comprises processor-executable instructions embodied on a storage memory device of a computing device to provide predictive learning techniques via a software environment. For example, AI system 104 may be provided as processor-executable instructions that comprise a procedure, a function, a routine, a method, and/or a subprogram utilized independently or in conjunction with additional aspects of system 100 according to an exemplary embodiment of the disclosure. Additional details regarding AI system 104 are provided herein.

The dietary database 106 is configured to store an organized collection of data representing one or more of a dietary history (e.g., food and/or nutrient consumption levels, etc.) of the patient, dietary preferences of the patient, food and/or nutrient consumption levels of populations in a given geographic area (e.g., worldwide, in a geographic locality of the patient, etc.), food composition (e.g., USDA National Nutrient Database for Standard Reference, USDA Branded Food Products Database, etc.), dietary supplement labels (e.g., Dietary Supplement Label Database from the National Institutes of Health), and the like.

The pharmacy-controlled medication delivery subsystem 108 is configured to allow a pharmacy actor (e.g., pharmacist, pharmacy staff member, pharmacy automated system, etc.) to administer medication to the patient. In one aspect, the system 100 (e.g., AI system 104) sends data to the pharmacy actor via the pharmacy-controlled medication delivery subsystem regarding the medication. Such data can include information related to the medication's dosage, type, and administration for example. In addition, aspects of AI system 104 can be used with systems and methods of pharmaceutical delivery, such as those described in U.S. Pat. No. 9,750,612, the entire disclosure of which is hereby incorporated by reference.

The electronic medical records database 110 is configured to store an organized collection of data representing one or more of demographics, medical history, medication history, allergies, immunization status, laboratory test results, radiology images, vital signs, personal statistics (e.g., age, weight, etc.), billing information, and the like for the patient and/or an entire population.

The global expert system 112 is configured to emulate decision-making abilities of one or more human experts regarding one or more aspects of monitoring, diagnosis, treatment, and prevention of disease, illness, injury, physical and/or mental impairments of the patient. In an embodiment, global expert system 112 includes a knowledge base of facts and/or rules (e.g., global rule set) for each patient and an inference engine that applies the rules to known facts to deduce new facts, explain situations, and the like. In an embodiment, global expert system 112 comprises processor-executable instructions embodied on a storage memory device of a computing device to provide predictive learning techniques via a software environment. For example, global expert system 112 may be provided as processor-executable instructions that comprise a procedure, a function, a routine, a method, and/or a subprogram utilized independently or in conjunction with additional aspects of system 100 according to an exemplary embodiment of the disclosure. Additional details regarding global expert system 112 are provided herein.

The patient-controlled medication delivery subsystem 114 is configured to allow the patient to administer his or her own medication. Exemplary routes of administration include, but are not limited to, oral, intravenous, epidural, inhaled, nasal, transcutaneous, and the like. Exemplary patient-controlled medication delivery systems include, but is not limited to, patient-controlled analgesia (PCA), an intravenous (IV) drip system, and the like.

The call button 116 is configured to enable the patient to alert the healthcare provider (e.g., doctor, nurse, staff member, etc.) of a need for aid.

The smart alert system 118 is configured to monitor and record physical properties associated with the patient (e.g., recent food, movement, sleep pattern, blood pressure, pulse, sweat, skin resistance, etc.) during a time period leading up to an activation of call button 116 by the patient, compile the monitored and recorded properties into an adaptive system, monitor the physical properties during a future time period, and proactively alert healthcare providers (e.g., via healthcare provider devices 120) when a similar set of property conditions are met. In this manner, smart alert system 118 is configured to alert healthcare providers, via healthcare provider devices 120, before the patient presses call button 116, for example. In an embodiment, smart alert system 118 comprises processor-executable instructions embodied on a storage memory device of a computing device to provide predictive learning techniques via a software environment. For example, smart alert system 118 may be provided as processor-executable instructions that comprise a procedure, a function, a routine, a method, and/or a subprogram utilized independently or in conjunction with additional aspects of system 100 according to an exemplary embodiment of the disclosure. Additional details regarding smart alert system 118 are provided herein.

The healthcare provider devices 120 are configured to provide access to AI system 104 and/or smart alert system 118 and/or provide alerts from smart alert system 118 to the healthcare providers. In an aspect, healthcare provider devices 120 are computing devices including, but not limited to, smartphone computing devices, smartwatches, tablet computing devices, desktop computing devices, and the like. Additionally or alternatively, healthcare provider devices 120 may include pagers, alarm clocks, buzzers, lights, printed notifications, and the like.

The patient devices 122 are configured to provide alerts from smart alert system 118 to the patient and/or provide access to AI system 104 by the patient. In an aspect, patient devices 122 are computing devices including, but not limited to, smartphone computing devices, activity monitoring devices, smartwatches, tablet computing devices, desktop computing devices, telpad computing devices (e.g., HC7-M Telpad available from PLDT Inc., etc.), and the like.

In an embodiment, medical devices are electrically and/or communicatively coupled to the AI system 104 and are configured to provide a medical treatment to a patient. For example, bone stimulators, neuro stimulators, and/or pain stimulators can be connected with the AI system 104 and controlled/operated by the AI system to delivery optimized and/or personalized patient treatment. In an embodiment, the medical device may be a robotic medical device such as those disclosed by U.S. Pat. No. 9,192,395, which is hereby incorporated by reference in its entirety. For example, aspects of system 100 (e.g., AI system 104) can direct a robotic medical device to deliver blood flow or pharmaceuticals to a specific locations through minimally invasive approaches, such as by magnetic guidance. In an embodiment, the medical device may be an endotracheal tube such as those disclosed by U.S. Pat. Nos. 6,820,614 and 7,320, 319, both of which are hereby incorporated by reference in their entirety.

In an embodiment, aspects of system 100 enable data for a specific patient to be compared relative to data (e.g., trends, etc.) for a group and/or subgroup of patients. Exemplary subgroups include, but are not limited to, age, gender, race, disease type, multiple disease types (e.g., ASA classification, etc.), and the like. For example, a 60 year old patient with diabetes and hypertension differs from an 80 year old patient with no disease-specific markers. Aspects of system 100 enable creating data trends for an individual, a subgroup (e.g., defined by healthcare provider to share and/or compare data, etc.) and a general group (e.g., age, sex, gender, country, location, etc.). For example, aspects of system 100 enable comparisons and identifications of variances on an individual basis, group basis, daily basis, nocturnal basis, day/night basis, based on when people eat and/or exercise and/or when people are exposed to different environmental conditions, such as sunlight. Moreover, this is just not limited to patient comparisons but can also include cellular functions and/or bacterial functions such as to optimize growth and/or inhibition.

In an embodiment, data collected by patient monitor sensors 102 is encrypted and/or is covered by regulatory (e.g., HIPPA, etc.) requirements. The data may be associated with the patient or the data may be anonymous and/or encrypted. Such data may include, but is not limited to, age, weight, gender, biometrics (e.g., macro, micro, cellular and/or mitochondrial), videos, and/or financials. A patient may choose to temporarily (e.g., during a hospital stay) and/or for a long term (e.g., at home) share data for use by aspects of system 100 or the data can be shared automatically with the system. For example, patient data may be collated to optimized medical treatments, workout regimens and/or timing, generic vs. specific drugs, neutraceutocals vs. over the counter drugs vs. no medication vs. workout time, and the like. In another embodiment, aspects of system 100 (e.g., AI system 104) utilize data collected by patient monitor sensors 102 to determine when a workout is most effective for a patient based on characteristics personal to the patient and/or a group to which the patient belongs and/or provides a best response for energy, endurance, and the like. In another embodiment, aspects of system 100 (e.g., AI system 104) utilize data collected by patient monitor sensors 102 to determine when is the best time for a patient to receive medication (i.e., not just if to take and dosage). In another embodiment, aspects of system 100 (e.g., AI system 104) utilize data collected by patient monitor sensors 102 to determine effects of food and/or physical activities on medication delivery. In another embodiment, aspects of system 100 (e.g., AI system 104) utilize data collected by patient monitor sensors 102 to determine whether a patient should workout and what is the best time to workout relative to medications and/or treatments. In aspect, these considerations are important for patients exhibiting multiple diseases, such as cancer and hypertension, diabetes and cardiovascular disease, and the like. In another embodiment, aspects of system 100 (e.g., AI system 104) predicts how patterns change over time (e.g., hourly, daily, monthly, etc.) for an individual and/or groups and optimizes efforts for schools, employers, families, churches, other social groups, and the like. The AI system 104 performs these determinations to optimize healthcare delivery for an individual patient instead of for healthcare provider staffing concerns, in an embodiment.

In another embodiment, aspects of system 100 (e.g., AI system 104) utilize data collected by patient monitor sensors 102 to determine an optimal and/or sub-optimal time for the user (e.g., patient) to study, eat, take medications, sleep, read for comprehension, concentrate, work, rest, socialize, call, text message, diet, eat, what to eat, and the like. For example, these determinations may be made on data sub-classified based on data points and may change as more data is obtained. In an embodiment, the user (e.g., patient) can actively control and turn on/off as desired.

In another embodiment, aspects of system 100 (e.g., AI system 104) determines how user actions can be modified by diurnal patterns and how to optimize environment, food, medications, local events, and the like and to predict and/or optimize body function and/or activity. In another embodiment, aspects of system 100 (e.g., AI system 104) determine when is the best time for a surgery or procedure, when to take medications, when to eat food, and the like. In an embodiment, a patient verbalizes discomfort (e.g., "I feel sick," "I have a headache," etc.) and aspects of system 100 (e.g., AI system 104) modifies recommendations on when to study, read, exercise, take medications, dosage levels, level of activity (e.g., how strenuous), and the like. In an embodiment, aspects of system 100 (e.g., AI system 104) communicate to an employer and/or healthcare provider how much activity, stress, medications, and the like is appropriate for an individual/patient. In an embodiment, aspects of system 100 (e.g., AI system 104) give direct feedback to the users/patients themselves on when, where, and how to complete various activities to obtain an optimal effect. In an embodiment, a user/patient can obtain an image of himself (e.g., a "selfie") to see facial movements or activity to determine health-related parameters and/or how active to be. In another embodiment, aspects of system 100 (e.g., AI system 104) utilize information from a reference (e.g., the Old Farmer's Almanac, horoscopes, etc.) in the intelligence mix to determine trends, such as diurnal (e.g., best time during day), and the like.

In another embodiment, patient monitor sensors 102 modify midstream so if the patient slept poorly, is under stress, is slower responding to questions, and the like, aspects of system 100 (e.g., AI system 104) change the patient's activity pattern for that day but not subsequent days. In this manner, aspects of the disclosure are not just comparing to a group but also with an individual's variation patterns note and modified on a daily, hourly, and the like basis. For example, if the individual is hung over he or she will be slower and won't perform as well during that day. The same concept applies in a hospital setting, school setting, and the like. For example, knowing status of employees (e.g., hung over, sleepy, etc.) affects how the individual is treated and the employer can staff a shift based on their abilities, problems, and the like.

In another embodiment, aspects of system 100 (e.g., AI system 104) determine if a patient needs a pain medication and if/when they need anxiolytics, anti-inflammatories, or just someone to talk to and/or music to pacify. For example, aspects of system 100 (e.g., patient monitor sensors 102 and/or AI system 104) determine these patterns by eye movement, temperature, sweating, core vs. peripheral movement, sweating palms vs. general sweating, heart rate changes, rate of breathing, how deep breathing is, shaking, tremors, tone of voice and the like. These "tells" (e.g., like in poker) may vary between patients but learning their response outside a hospital setting helps inside the hospital setting and/or after surgery and the like. In an embodiment, knowledge of these "tells" by aspects of system 100 also help healthcare providers (e.g., nurses) respond.

In another embodiment, aspects of system 100 (e.g., AI system 104) can be used to regulate or control medical devices were a treatment is varied based on body motion, activity, diet, nutrition, sunlight, and/or environmental conditions. Such medical devices may include, for example, neuromuscular stimulators, pain stimulators and/or pacemakers that deliver an electrical flow (broadly, treatment) to the patient. For example, internal pacemakers simply try to regulate the heart rate to a known condition using electrical flow. However, pacemakers, generally, are set to regulate the heart rate of a patient to a set rate to treat a heart condition (e.g., atrial-fibrillation or ventricular fibrillation or when the heart as asystolically or has multiple heartbeats in a shorter period of time). Aspects of system 100 can monitor the patient and vary or adjust the heat rate the pacemaker regulates the heart of the patient at. For example, AI system 104 can identify when a patient is under a high degree of stress, such as by analyzing data from a patient monitor sensor 102, and control the pacemaker to adjust or alter the heart rate based on the amount of stress. A change in a patient's stress level may be due to a fear, apprehension, or exercise. Moreover, AI system 104 may change the heart rate for other conditions such as when a patient is eating, moving, or resting. Accordingly, instead of a constant heart rate set by the pacemaker, the AI system 104 can regulate the heart rate imposed by the pacemaker based on the needs of the patient.

In another embodiment, aspects of system 100 (e.g., AI system 104) are not just limited to patients and can be used in other areas such as for animals, living cells, bacteria, cell growth, cell culture, tissue culture, and other aspects of microbiology. In addition, the aspects system 100 can be used for cellular growth, cellular mechanics mitochondrial mechanics, bacterial growth, and bacterial functions. For example, aspects of system 100 can be used for cellular growth in 3D printing applications.

In accordance with one or more embodiments:

Aspects of system 100 (e.g., patient monitor sensors 102 and/or AI system 104) monitor physical properties of the patient, such as patient movement and sleep patterns, and shift drug delivery, blood pressure measurements, and blood draws, food delivery, and the like up/back to a predetermined amount of time so they are performed at an optimal time in the patient's sleep schedule.

Aspects of system 100 (e.g., AI system 104) combine sleep patterns for multiple patients to create an optimal room order for a phlebotomist, dietician, nurse, food deliverer, and the like to follow to minimize patient disturbances.

When a patient is checked in, a local copy of the global rules set (e.g., global expert system 112) is created. Aspects of system 100 (e.g., AI system 104) integrate patient-specific information in the patient's rule set. Aspects of system 100 (e.g., AI system 104) add adaptive rules based on patient behaviors.

When the patient presses the bed-side call button 116 the signal is sent to a nurse either via a traditional call system or through smart alert system 118. Aspects of system 100 (e.g., AI system 104, smart alert system 118, etc.) would then record the conditions when the button was pressed (e.g., recent food, movement, sleep patterns, BP, pulse, sweat, etc.). Aspects of system 100 (e.g., AI system 104, smart alert system 118, etc.) uses this information to compile an adaptive system that could set alerts before the patient presses the call button 116 in the future. For example, when a similar set of conditions are met or the conditions are within a threshold the alert would be set. In one or more embodiments, after the hospital staff is notified, there is a feedback mechanism for the patient and/or the hospital staff that would indicate if the alert was a false alert. Reduced call button presses could indicate that the AI generated rules are having a positive result. Aspects of system 100 (e.g., AI system 104, smart alert system 118, etc.) would then use this scoring system to intelligently modify the created rule set. Other known AI weighting algorithms could be used. The AI System 104 could also ensure the nurse responds to the call button 116.

Aspects of system 100 include safety measures to ensure that the alerts generated by AI system 104 and/or smart alert system 118 cannot bypass the global/expert system rules in global expert system 112.

Rules generated by AI system 104 and/or smart alert system 118 are compiled and integrated into global expert system 112.

Aspects of system 100 (e.g., AI system 104) monitor the food and/or water intake patterns of the patient so that changes in diet, portion size, and the like can be monitored.

Aspects of system 100 (e.g., smart alert system 118) queue the patients information by severity of alert (e.g., higher priority given to more critical cases). For example, a patient with critical blood pressure levels would get a higher rating than a patient who had all normal readings.

A hospital medical records system is integrated into system 100 so that all information in a patient's records could be used as an input to system 100.

A goal of AI is the creation of an intelligent computer system. These intelligent systems can be used to optimize systems and methods for healthcare delivery to provide better care and increase patient satisfaction. At a high level, AI has been broken into strong AI, which believes machines can be sentient, and weak AI, which does not. Although embodiments described herein focus on weak AI, they can also be implemented with a strong AI system in accordance with one or more aspects of the disclosure. While the embodiments disclosed herein are related to healthcare, it is understood that aspects of system 100 may also apply to non-medical applications, such as but not limited to industrial systems, commercial systems, automotive systems, aerospace system and/or entertainment systems.

Data analysis by the AI system 104 can include pure algorithms or individual or panels that review and comment at specific data analysis points ("opinion" data). The "opinion" data could be included for further analysis or bifurcated into a column with and without expert (e.g., humanistic) data analysis and evaluate conclusions. Human analysis could be individual specialist or pooled group specialists or different specialists like oncologist then a statistician then economist then ethics expert. Each can add analysis at certain critical points, and then reanalyze the data for conclusions. The AI system 104 may then analyze the human conclusion and compare them to its own. This adds a biological factor to analysis and not pure analysis from data.

In all embodiments there may be an advantage to combining known types of AI such as expert systems, genetic algorithms, deep learning, and convolutional neural networks (CNN) to implement a unique approach to the system. Convolutional neural networks and deep learning can be very useful in image recognition, such as recognizing a cat. There are cases such as robotic surgery, medical diagnosis, or reviewing medical journals which may not lend itself to traditional AI methods. For example, when using peer reviewed journals to assist in diagnosing a medical condition it may be necessary to perform an interim analysis of the data to ensure that all the conditions and symptoms of the patient are being considered or articles which not applicable are being excluded. Because interim analysis of traditional CNN is not something that can be easily done due to the encoding of the data. Because of this it could be preferable to break the CNN into multiple CNN with an expert system or evaluation by experts at each stage. The interim could be done could be done by a single user, or a system could be setup where the results are done by peer review where multiple users review. In a system with multiple users reviewing the interim of final results, it could be done through a website interface where in exchange for the reviewing of the data the users were given access to the peer reviewed articles or the input data at no charge.

Another embodiment of the AI system 104 may be constructed in a way to question data points and how it affects the entire algorithm. For example, one looks at entire chaining of information to end up with a conclusion. For example, if one looks at a research article, the conclusions of a research article are often based upon the references within the article. However, if one of these references is erroneous, it would be necessary to remove this data and through machine learning change the ultimate algorithm so that the conclusion is changed based on changing or altering one of the reference or data points. The operator could change this data format or this reference as and mark it as an invalid or questionable point. Grouping AI algorithms could also be used to do this. This method of interim analysis could also be used to allow and experts to review and weight the results for search results that may not have a black and white or definitive answer. The expert, or an expert system algorithm, could be used to weight the output of the AI system 104 or search results. This could be used in internet search engines, drug databases, or any algorithm that produces none definitive results.

For example, if one changes the data point/reference of how a black male would function relative to a total knee replacement versus elderly white female. The AI system 104 would allow for changes to one of the data points in terms of functional return or risks of keloid formation and the impact on how this affects stiffness of the joint, range of motion, and function. It may have an impact on the algorithm for sensing the ligament balance within the joint or how one would allow bone resection via MAKO robotic system to move the knee. The AI system 104 would allow the user to alter that based on the risks of scar tissue forming and what would the scar risk be for elderly white female versus younger black male versus a patient with sickle-cell anemia versus patient that would have very elastic soft tissue. Current systems do not allow this change in concepts on the fly based on individual data. This could be inputted manually by the operator or it could allow multiple variables to say if the patient has sickle-cell, Ehlers-Danlos, or keloid formation. These changes of the data could affect the incision approach, robotic mechanism for tissue resection, tissue repair, and the amount of bone to be removed for a total knee replacement to optimize function. This would also link to sensors and postoperative function/rehabilitation so one could enhance the rehabilitation/recovery. If this patient needs more aggressive therapy to work on flexion or to deal with keloid/hyperelasticity of the tissue or how one could improve scar formation and function.

Embodiments described herein may be implemented using global expert system 112, which utilizes the knowledge from one or more experts in the algorithm executed thereby. A system of rules and data is required prior to the running of global expert system 112. Global expert system 112 can be implemented such that in the introduction of new knowledge is rebuilt into the code, or the code can dynamically update to include new knowledge generated by global expert system 112 and/or AI system 104. In an embodiment, updates to the code of global expert system 112 are validated with respect to regulatory requirements before implementation.

In an embodiment, AI system 104 implements one or more genetic algorithms. Genetic algorithms use the principles of natural selection and evolution to produce several solutions to a given problem. In an exemplary approach, AI system 104 randomly creates a population of solutions of a problem. The AI system 104 then evaluates and scores each solution using criteria determined by the specific application. The AI system 104 selects the top results, based on the score, and uses them to "reproduce" to create solutions which are a combination of the two selected solutions. These offspring go through mutations and AI system 104 repeats these steps or a portion of the steps until a suitable solution is found. Additionally or alternatively, AI system 104 utilizes other known AI techniques such as neural networks, reinforcement learning, and the like.

In an aspect, AI system 104 uses a combination of known AI techniques. In an embodiment, AI system 104 uses an expert system (e.g., global expert system 112) as a global ruleset that has a local copy of the rules created for each patient who is checked into system 100. AI system 104 uses adaptive rules to modify the local rule set for each individual patient. Instead of a complete local copy, only the modified rules could be kept locally at a computing device executing processor-executable instructions for implementing AI system 104 and/or global expert system 112 to reduce the required memory needed. In an embodiment, a safety control is included so that rules and/or alerts generated by AI system 104 and/or global expert system 112 (e.g., the inference engine) cannot bypass one or more (or a group) of the global or expert system rules. Rules generated by AI system 104 or rules from the predictive rules are compiled and/or integrated into the global or expert rule set in accordance with one or more embodiments.

Figure 2:
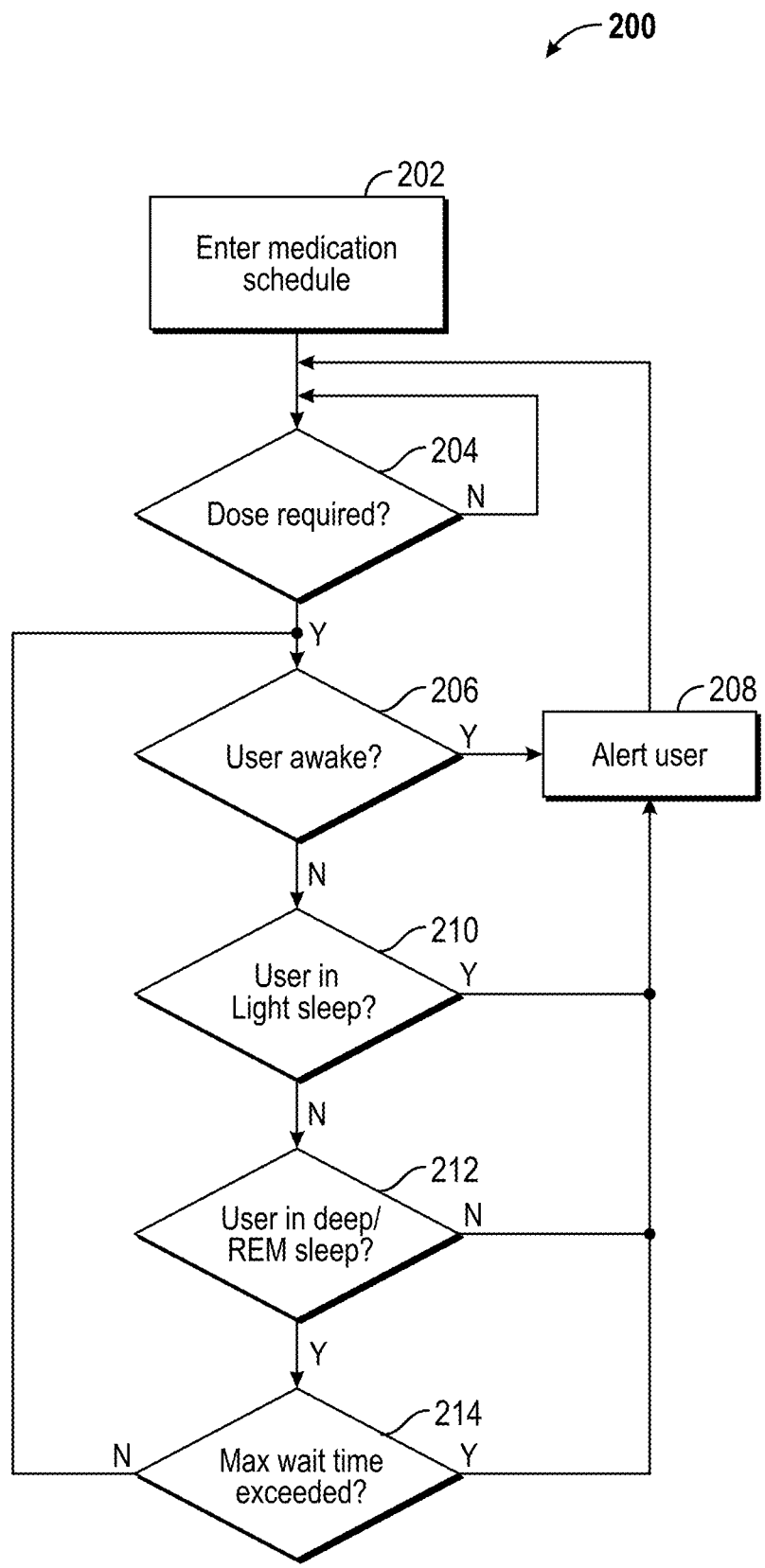
FIG. 2 is a block diagram of an exemplary waking/alerting algorithm according to an embodiment.

One embodiment of using system 100 in a hospital environment includes maximizing a patient's ability to rest at night by scheduling certain procedures and activities around the patient's sleep patterns. During a normal sleep pattern a person goes through different cycles of sleep, including light sleep, deep sleep, and REM. A patient's sleep patterns, heart rate, and movements at night are monitored using patient monitor sensors 102 (e.g., Fitbit® activity tracker, Apple® Watch, smartphone computing device, an electronic ring, or any commercial or custom tracker with the ability to record and or transmit patient's movements and sleep patterns). Additionally or alternatively, system 100 utilizes patient monitor sensors 102 in the form of existing sensors used in hospital monitoring systems, hospital records, pulse oximeter, retinal changes, temperature, or thermal gradients, changes in diet or food patterns from dieticians, and mediation from the pharmacy. The data collected from patient monitor sensors 102 is then uploaded (e.g., via a communications network) to AI system 104 in real time for analysis. Additionally or alternatively, the data collected from patient monitor sensors 102 is manually uploaded to AI system 104 for analysis. The AI system 104 then uses this information to ensure that the patient is in the correct sleep cycle when they must be woken up for procedures, such as by execution of a waking/alerting algorithm 200 (FIG. 2). For example, system 100 monitors all patients on a certain a floor and creates an optimized map or order of blood draws for the phlebotomist to minimize the patients being disturbed from deep sleep. This map could be printed along with the ordered bloodwork or could be sent wirelessly to healthcare provider device 120 (e.g., a tablet or smartphone computing device) and updated in real time. The same algorithm could be used by multiple departments in the hospital so that medication delivery, food, etc. is optimally scheduled.

For patients who are taking medications at night outside of the hospital the waking/alerting algorithm 200 may be implemented by one or more patient devices 122 (e.g., a smartwatch, smartphone computing device, tablet computing device, or other monitor) to wake the user at an optimal time in the sleep cycle to take medication. In an embodiment, system 100 is also used to determine the optimal time of the day to take a medicine for an individual user based on daily activity level, sleep patterns, metabolism, and like factors.

FIG. 2 illustrates an exemplary embodiment of the waking/alerting algorithm 200. In an embodiment, the waking/alerting algorithm 200 comprises processor-executable instructions embodied on a storage memory device of a computing device to provide waking/alerting techniques for medication delivery via a software environment. For example, the waking/alerting algorithm 200 may be provided as processor-executable instructions that comprise a procedure, a function, a routine, a method, and/or a subprogram utilized independently or in conjunction with additional aspects of system 100 according to an exemplary embodiment of the disclosure. In an embodiment, the waking/alerting algorithm 200 is executed by a computing device, such as one or more of a computing device implementing AI system 104, patient monitor sensors 102, and patient devices 122 in accordance with one or more embodiments of the disclosure.

At 202, the patient or healthcare provider enters the medication schedule. For example, the patient may enter the medication schedule via patient monitor sensors 102, patient device 122, and/or patient-controlled mediation delivery subsystem 114 and the healthcare provider may enter the medication schedule via healthcare provider device 120.

At 204, the computing device determines whether a dose is required at the current time according to the entered schedule. When a dose is determined to be not required at 204, the algorithm 200 loops back to 204. When a dose is determined to be required at 204, the algorithm advances to 206.

At 206, the computing device determines whether the user (e.g., patient) is awake. In an embodiment, the computing devices uses data collected from one or more patient monitor sensors 102 to make this determination as further described herein. Exemplary patient monitor sensors are described herein, including a smartwatch, an activity monitor, a camera, and the like. When the user is determined to be awake at 206, the user is alerted at 208 (e.g., via patient device 122 and/or patient monitor sensors 102) for medication delivery. After alerting the user at 208, the algorithm advances back to 204. When the user is determined to be not awake at 206, the algorithm advances to 210.

At 210, the computing device determines whether the user is in light sleep. In an embodiment, the computing devices uses data collected from one or more patient monitor sensors 102 to make this determination as further described herein. Light sleep includes sleep that falls into the categories of Stage 1 and Stage 2 in accordance with an aspect of the disclosure. When the user is determined to be in light sleep at 210, the user is alerted at 208 (e.g., via patient device 122 and/or patient monitor sensors 102) for medication delivery. After alerting the user at 208, the algorithm advances back to 204. When the user is determined to not be in light sleep at 210, the algorithm advances to 212.

At 212, the computing device determines whether the user is in deep sleep and/or rapid eye movement (REM) sleep. In an embodiment, the computing devices uses data collected from one or more patient monitor sensors 102 to make this determination as further described herein. Deep sleep includes sleep that falls into the categories of Stage 3 and Stage 4 in accordance with an aspect of the disclosure. When the user is determined to not be in deep or REM sleep at 212, the user is alerted at 208 (e.g., via patient device 122 and/or patient monitor sensors 102) for medication delivery. After alerting the user at 208, the algorithm advances back to 204. When the user is determined to be in deep and/or REM sleep at 212, the algorithm advances to 214.

At 214, the computing device determines whether a maximum wait time is exceeded. For example, the maximum wait time may be a predefined threshold for the maximum time allowed between medication dosage deliveries. When the maximum wait time is not exceeded at 214, the algorithm loops back to 206. When the maximum wait time is exceeded at 214, the user is alerted at 208 (e.g., via patient device 122 and/or patient monitor sensors 102) for medication delivery. After alerting the user at 208, the algorithm advances back to 204.

In an embodiment, the waking/alerting algorithm 200 executes on a computing device as a standalone system. In another embodiment, the waking/alerting algorithm 200 executes on a computing device as part of a larger (e.g., hospital-wide) system. Exemplary computing devices on which the waking/alerting algorithm 200 can be executed include, but are not limited to, a smartwatch, an activity monitor, a smartphone, and the like. In an embodiment, the user is alerted via the device that executes the waking/alerting algorithm 200 (e.g., a smartwatch, an activity monitor, a smartphone, etc.). In another embodiment, the user is alerted via an external device, such as a pager, an alarm clock, a notification given to a healthcare provider or other caregiver, and the like.

The alerting algorithm 200 is not limited to sleep and can be used when the user is performing other activities (e.g., work, personal, entertainment, employment). For example, the alerting algorithm 200 can be executed on a portable computing device, such as a smart watch, while the user is running or exercising. Similar to tracking a user's sleep, the alerting algorithm 200 can track the user's exercising and then the algorithm would alert the user to take the medication, via the portable computing device, after the user has finished exercising or the maximum wait time is exceeded. In addition, similar to light and deep sleep, the alerting algorithm 200 can determine if the user is experiencing light exercise or heavy exercise and alert the user accordingly regarding the medication. Moreover, the alerting algorithm 200 can include GPS and alert the user to take a medication once the user has reached a specific location, such as their home.

Figure 3:
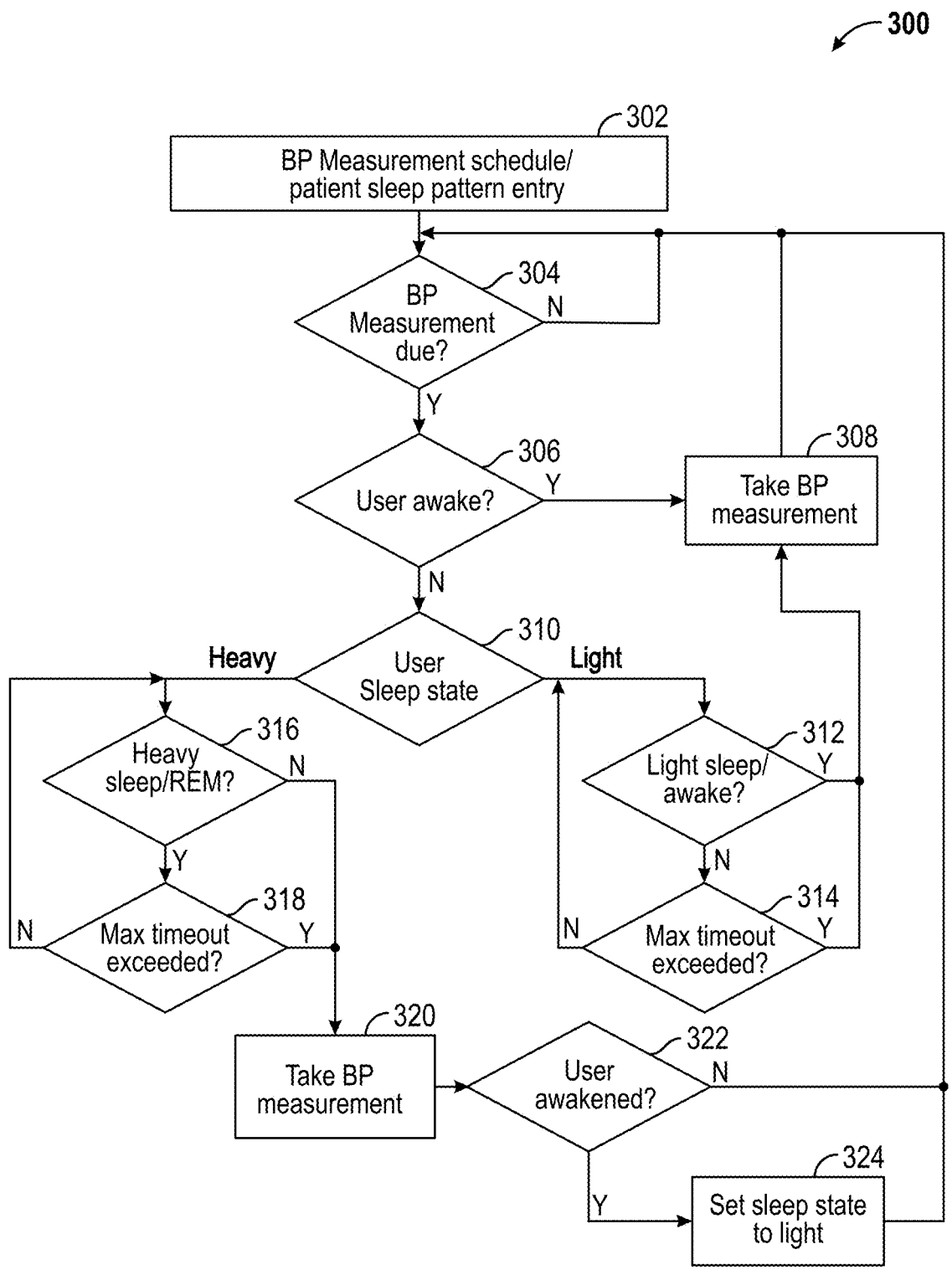
FIG. 3 is a block diagram of an exemplary automated blood pressure measurement algorithm according to an embodiment.

Referring again to FIG. 1, system 100 may be integrated into devices (e.g., patient monitoring devices 102, patient devices 122, etc.) in a room that can disturb the patient during sleep. The system 100 may be a central system or a local version thereof in accordance with one or more embodiments. An example includes automated blood pressure measurements (e.g., automated blood pressure measurement algorithm 300; FIG. 3) using a sphygmomanometer. By monitoring the patient's sleep pattern, the measurements are performed when the patient is in light sleep to maximize the amount of deep sleep the patient has. In other words, light sleep stages are interrupted while deep sleep stages are left uninterrupted. In an embodiment, AI system 104 executes a learning algorithm to determine if the patient is a heavy sleeper or a light sleeper and if taking the measurements during a deep sleep cycle did not disturb the patient they could be performed during those cycles. In another embodiment, system 100 puts hard limits on the amount of time a measurement can be shifted forward or backward to ensure that too much time does not elapse between measurements.

FIG. 3 illustrates an exemplary embodiment of an automated blood pressure measurement algorithm 300. In an embodiment, automated blood pressure measurement algorithm 300 comprises processor-executable instructions embodied on a storage memory device of a computing device to provide automated blood pressure measurement techniques via a software environment. For example, the automated blood pressure measurement algorithm 300 may be provided as processor-executable instructions that comprise a procedure, a function, a routine, a method, and/or a subprogram utilized independently or in conjunction with additional aspects of system 100 according to an exemplary embodiment of the disclosure. In an embodiment, the automated blood pressure measurement algorithm 300 is executed by a computing device, such as one or more of a computing device implementing AI system 104, patient monitor sensors 102, and patient devices 122 in accordance with one or more embodiments of the disclosure.

At 302, the patient or healthcare provider enters a blood pressure measurement schedule and/or patient sleep schedule. For example, the patient may enter the blood pressure measurement schedule and/or patient sleep schedule via patient monitor sensors 102, patient device 122, and/or patient-controlled mediation delivery subsystem 114 and the healthcare provider may enter the blood pressure measurement schedule and/or patient sleep schedule via healthcare provider device 120.

At 304, the computing device determines whether a blood pressure measurement is due at the current time according to the entered schedule. When a measurement is determined to not be due at 304, the algorithm 300 loops back to 304. When a measurement is determined to be required at 304, the algorithm advances to 306.

At 306, the computing device determines whether the user (e.g., patient) is awake. In an embodiment, the computing devices uses data collected from one or more patient monitor sensors 102 to make this determination as further described herein. Exemplary patient monitor sensors are described herein, including a smartwatch, an activity monitor, a camera, and the like. When the user is determined to be awake at 306, a blood pressure measurement is automatically taken at 308. After taking the measurement at 308, the algorithm advances back to 304. When the user is determined to not be awake at 306, the algorithm 300 advances to 310.

At 310, the computing device determines whether the user is in a light sleep or a heavy (i.e., deep) sleep. In an embodiment, the computing devices uses data collected from one or more patient monitor sensors 102 to make this determination as further described herein. Light sleep includes sleep that falls into the categories of Stage 1 and Stage 2 and heavy sleep includes sleep that falls into the categories of Stage 3 and Stage 4 and/or REM sleep in accordance with an aspect of the disclosure. When the user is determined to be in light sleep at 310, the algorithm advances to 312. When the user is determined to be heavy sleep at 310, the algorithm advances to 316.

At 312, the computing device determines whether the user is in light sleep or awake. In an embodiment, the computing devices uses data collected from one or more patient monitor sensors 102 to make this determination as further described herein. When the user is determined to be in light sleep or awake at 312, a blood pressure measurement is automatically taken at 308. After taking the measurement at 308, the algorithm advances back to 304. When the user is determined to not be in light sleep or awake at 312, the algorithm advances to 314.

At 314, the computing device determines whether a maximum timeout is exceeded. For example, the maximum timeout may be a predefined threshold for the maximum time allowed between blood pressure measurements. When the maximum timeout is not exceeded at 314, the algorithm loops back to 312. When the maximum timeout is exceeded at 314, a blood pressure measurement is automatically taken at 308. After taking the measurement at 308, the algorithm advances back to 304.

At 316, the computing device determines whether the user is in heavy or REM sleep. In an embodiment, the computing devices uses data collected from one or more patient monitor sensors 102 to make this determination as further described herein. When the user is determined to be in heavy or REM sleep at 316, the algorithm advances to 318. When the user is determined to not be in heavy or REM sleep at 316, a blood pressure measurement is automatically taken at 320 before proceeding to 322.

At 318, the computing device determines whether a maximum timeout is exceeded. For example, the maximum timeout may be a predefined threshold for the maximum time allowed between blood pressure measurements. When the maximum timeout is not exceeded at 318, the algorithm loops back to 316. When the maximum timeout is exceeded at 318, a blood pressure measurement is automatically taken at 308 before proceeding to 322.

At 322, the computing device determines whether the automated blood pressure measurement taken at 320 awakened the user. In an embodiment, the computing devices uses data collected from one or more patient monitor sensors 102 to make this determination as further described herein. When the user is determined to not be awakened at 322, the algorithm advances back to 304. When the user is determined to be awakened at 322, the computing device sets the user sleep state to "light" at 324 before advancing back to 304.

In an embodiment, the automated blood pressure measurement algorithm 300 executes on a computing device as a standalone system. In another embodiment, the automated blood pressure measurement algorithm 300 executes on a computing device as part of a larger (e.g., hospital-wide) system. Exemplary computing devices on which the automated blood pressure measurement algorithm 300 can be executed include, but are not limited to, a smartwatch, an activity monitor, a smartphone, and the like. While this embodiment utilizes a blood pressure monitor, it is understood that this system could be used for any automated test which is done during sleep. Moreover, it is understood that this embodiment could be used in non-medical applications where the interrupting activity might disturb sleep patterns such as, but not limited to, the operation of robotic vacuums, cleaning systems, air filters, heating ventilation and air conditioning systems, non-emergency alarms, washers and dryers, and/or dishwashers.

Referring again to FIG. 1, aspects of system 100 are integrated into the bedside call button (e.g., call button 116), in an embodiment. When the patient presses call button 116, a signal is sent to the healthcare provider (e.g., nurse, etc.) via a traditional call system and/or through smart alert system 118. A predictive alert subsystem of smart alert system 118 records one or more conditions when call button 116 was pressed (recent food, movement, sleep patterns, BP, pulse, sweat, skin resistance, etc.). The smart alert system 188 the uses this information to start to compile an adaptive system that is capable of alerting the healthcare provider (e.g., via healthcare provider devices 120) before the patient presses call button 116 in the future. For example, when smart alert system 118 determines that a similar set of conditions are met or the conditions are within a threshold, smart alert system sends the alert to the healthcare provider via healthcare provider devices 120. In an embodiment, after the healthcare provider responds to a system-generated call button press, the healthcare provider and/or the patient have the ability to score the alert. For instance, the healthcare provider may score the alert via healthcare provider devices 120 and the patient may score the alert via patient monitoring sensors 102 and/or patient devices 122. False alerts would receive a low rating and reduce the chance of a similar condition set triggering an alert in the future. A higher rating, or a reduction of call button 116 presses by the patient, could indicate a positive result and increase the chance that similar conditions would trigger an alert to the healthcare provider via healthcare provider devices 120. In an aspect, smart alert system 118 uses this scoring system and/or other known AI techniques to intelligently modify the rule set (e.g., rules in global expert system 112 and/or AI system 104) for each patient. In another embodiment, alerts from multiple patients are weighted by severity of the situation (e.g., higher priority given to more critical conditions, etc.) to ensure the healthcare providers are able to prioritize emergency situations.

In an embodiment, aspects of system 100 are integrated into medications delivered by patient-controlled medication delivery subsystem 114 (e.g., patient controlled analgesia (PCA), etc.). In an aspect, the AI system 104 monitors one or more physical properties of a patient, such as patient sleep patterns, pulse rate, blood pressure, skin resistance, and like properties, to determine when a patient's pain has increased. By predicting pain levels, AI system 104 then varies the dosing so that the patient's discomfort is minimized. In another aspect, the AI system 104 determines when a patient is pressing the button but not experiencing pain and adjusts the dosage accordingly to minimize abuse.

Figure 4:
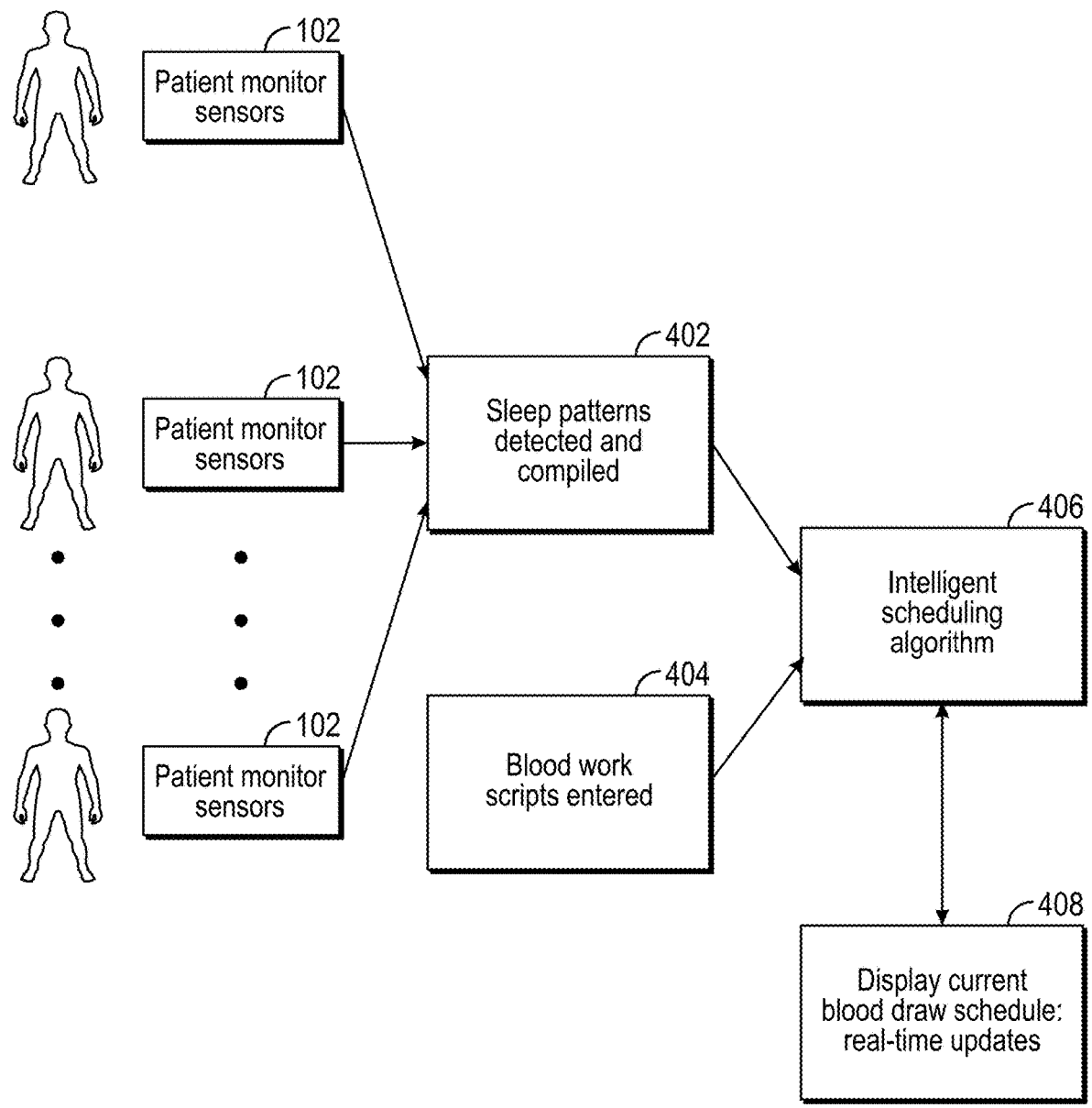
FIG. 4 is a block diagram of an exemplary blood draw algorithm and system according to an embodiment.

FIG. 4 is a block diagram of an exemplary blood draw algorithm and system. In an aspect, patient monitor sensors 102 sense physical properties associated with one or more patients. The data collected by patient monitor sensors are transmitted to AI system 104 via a communications network (e.g., wired communication, wireless communications, etc.), as further described herein. The data collected by patient monitor sensors may additionally or alternatively be transmitted via the communications network to a data repository (e.g., database, cloud service, etc.) for storing the data in advance of AI system 104 utilizing the data. At 402, AI system 104 detects and compiles patient sleep patterns from the collected data. At 404, blood work scripts are entered into AI system 104 and/or a data repository associated therewith. For example, the blood scripts may be entered by a healthcare provider via healthcare provider devices 120, obtained from electronic medical records database 110, and the like. At 406, AI system 104 executes an intelligent scheduling algorithm to generate an optimized and/or personalized blood draw procedure schedule for each patient and/or for the group of patients. At 408, the generated schedule and/or real-time updates thereto are communicated to one or more healthcare providers (e.g., phlebotomist, etc.). For example, the generated schedule and/or real-time updates are communicated to the healthcare provider via healthcare provider devices 120 (e.g., tablet computing device, etc.), as further described herein. In an embodiment, one or more aspects of the exemplary blood draw algorithm and/or system are integrated with a distributed medical record (DMR) system and/or laboratory software.

Figure 5:
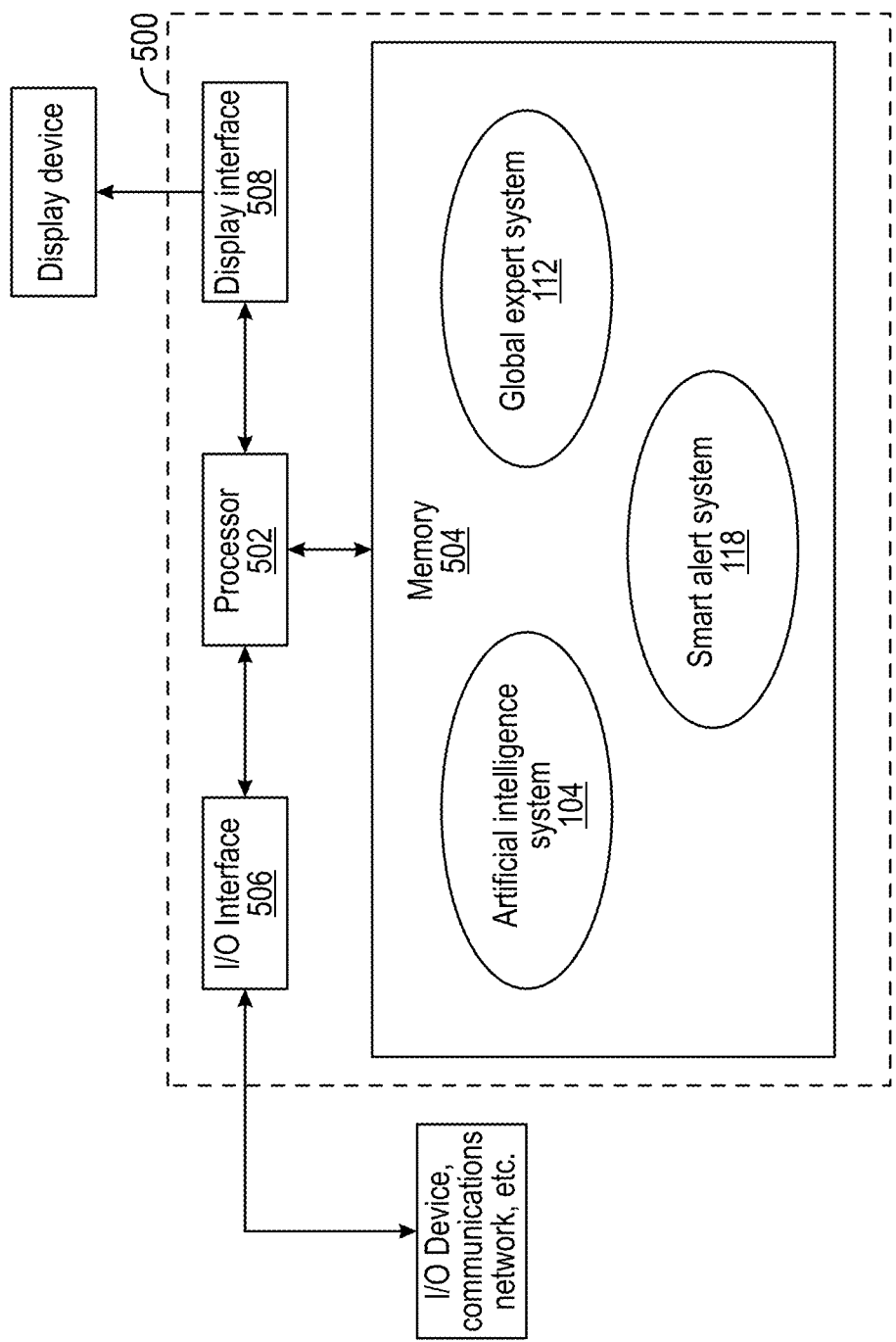
FIG. 5 illustrates an exemplary architecture of a computing device configured to provide aspects of the systems and processes described herein via a software environment.

FIG. 5 illustrates an exemplary architecture of a computing device 500 configured to provide aspects of the systems and processes described herein via a software environment. In this embodiment, the computing device 500 includes a processor 502, a memory device 504, an input/output (I/O) interface 506, and a display interface 508. The memory device 504 includes processor-executable instructions for executing by processor 502 that carry out processes for artificial intelligence techniques that optimize and/or personalize one or more aspects of monitoring, diagnosis, treatment, and prevention of disease, illness, injury, physical and/or mental impairments of the patient, emulate decision-making abilities of one or more human experts regarding one or more aspects of monitoring, diagnosis, treatment, and prevention of disease, illness, injury, physical and/or mental impairments of the patient, alert healthcare providers before the patient presses call button 116, provide waking/alerting techniques for medication delivery, and provide automated blood pressure measurement techniques, as further described herein. In this manner, computing device 500 comprises a special-purpose computing device for optimizing and/or personalizing one or more aspects of monitoring, diagnosis, treatment, and prevention of disease, illness, injury, physical and/or mental impairments of the patient, emulating decision-making abilities of one or more human experts regarding one or more aspects of monitoring, diagnosis, treatment, and prevention of disease, illness, injury, physical and/or mental impairments of the patient, alerting healthcare providers before the patient presses call button 116, providing waking/alerting techniques for medication delivery, and/or providing automated blood pressure measurement techniques in accordance with an aspect of the disclosure.

The processor 502, memory 504, I/O interface 506, and display interface 508 are communicatively connected and/or electrically connected to each other. The I/O interface 506 may be communicatively connected to a communications network, as further described herein, an I/O device, and the like. The processor 502 is adapted to execute processor-executable instructions stored in the memory 504 for optimizing and/or personalizing one or more aspects of monitoring, diagnosis, treatment, and prevention of disease, illness, injury, physical and/or mental impairments of the patient, emulating decision-making abilities of one or more human experts regarding one or more aspects of monitoring, diagnosis, treatment, and prevention of disease, illness, injury, physical and/or mental impairments of the patient, alerting healthcare providers before the patient presses call button 116, providing waking/alerting techniques for medication delivery, and/or providing automated blood pressure measurement techniques in real time. The I/O interface 506 of FIG. 5 provides a physical data connection between computing device 502 and a communications network, in an embodiment. In an embodiment, I/O interface 506 is a network interface card (NIC) or modem. The display interface 508 provides a physical data connection between computing device 502 and a display device. In an embodiment, the display device is an LCD indicator display that includes a keypad for human interface. In another embodiment, the display device is a touchscreen on computing device 502 and/or a touchscreen of a smartphone, tablet computing device, or the like comprising one or more of patient monitoring sensors 102, patient-controlled medication delivery subsystem 114, call button 116, healthcare provider devices 120, and patient devices 122.

In addition to using artificial intelligence in the healthcare environment, virtual reality (VR) and/or augmented reality ("VR/AR") games can play an important part in healthcare and rehabilitation. Virtual reality creates a convincing simulated 3D environment which allows the user to interact in a natural way for example, by projecting visible light directly onto the retina to create a virtual image. Virtual reality systems are traditionally classified as immersive, semi-immersive, and non-immersive systems. In an exemplary immersive VR system, the user wears a head mounted display (HMD). Sensory inputs are delivered through the HMD unit, gloves, suits, clothing, and the like. Additional movement and responses may be obtained with other handheld and/or body sensors, cameras, joysticks, and the like. In an exemplary semi-immersive system, multiple monitors and/or large screen projectors with a wide field of view are used. In an exemplary non-immersive system, conventional monitors, gaming platform, controllers or keyboards and a mouse are used. Embodiments described herein can be implemented using an immersive, semi-immersive, and/or non-immersive system.

Figure 6:
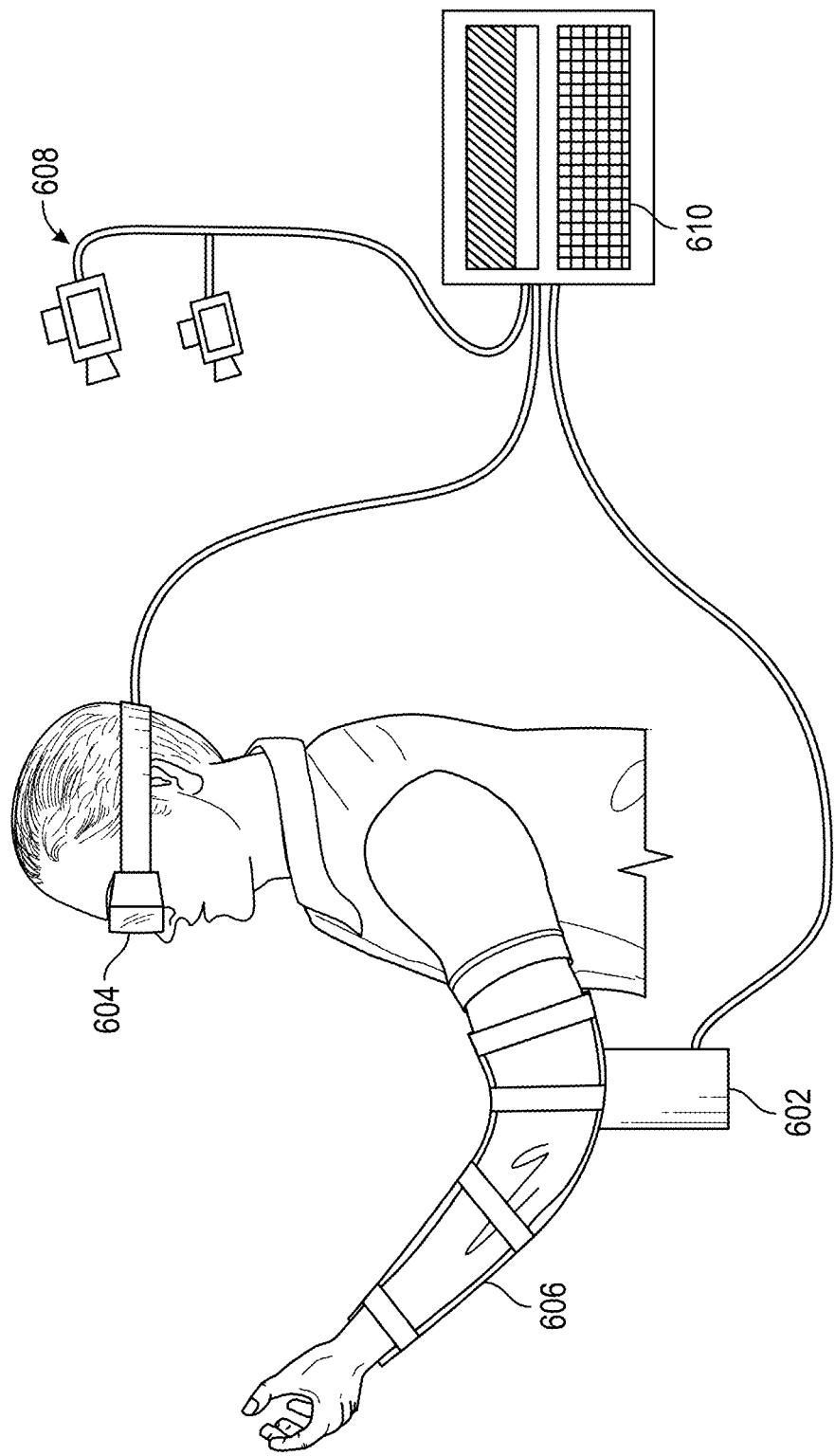
FIGS. 6-12 illustrate an exemplary virtual reality system according to an embodiment.

During physical therapy, VR can be used to create an environment where exercises and therapy can be personalized to an individual patient's needs. FIG. 6 illustrates an exemplary VR system in accordance with an aspect of the disclosure. The VR system includes a Joint Active System (JAS) device 602, a HMD 604, a cuff 606, sensors 608 in the form of cameras in this embodiment, and a computing device 610 (e.g., patient device 122).

In one embodiment, a static progressive stretch unit such as a Joint Active System (JAS) device 602 is integrated with sensors (e.g., patient monitor sensors 102) which would then be used as inputs to the VR system. The static progressive stretch unit may also be a dynamic splinting device, tens device, electro-stimulation device, ultrasound device, exercise bike, continuous passive motion device (CPM), bone growth stimulator, and any other therapy device. In an embodiment, the sensors are integrated into cuff 606, attached to the patient, and the like. The JAS device 602 could be manually driven or equipped with a motor to drive the movement. Traditionally, JAS devices are used in a home use environment. As the patient worked through the treatment protocol for the JAS device the virtual environment could appear to be in a physical therapy office, for example. A virtual physical therapist could instruct the patient through the stretch and hold protocol, in an embodiment. In addition to monitoring the position on the device, the system could monitor other inputs such as blood pressure, heart rate, and the like. The virtual therapist could use aspects of system 100 (e.g., AI system 104, etc.) to dynamically adjust the treatment in response to the patient's ability for movement and/or feedback from other sensors. In addition to monitoring the position of the JAS device 602 by using sensors, the system could use a camera and/or other methods to monitor the position of patient to determine the degree of stretch. Instead of using the virtual environment of a physical therapy office, any environment could be used that could enhance therapy, such as by relaxing the patient, motivating them to perform therapy, and the like. Instead of the patient or therapist selecting the virtual environment, one could be elected from existing patient information or web search history. Some forms of physical therapy and stretching could be done without an external device and could use gloves, position sensors, cameras, and the like to monitor the patient's position and move them through stretches. In an embodiment, the sensors and motor drive may be attached to standalone computing device 610. In another embodiment, processing is performed in HMD 604. In another embodiment, processing is integrated into JAS device 602. Although FIG. 6 illustrates an exemplary embodiment in which the elbow is used, the VR system can be used on any joint or extremity. Moreover, sensors 608 may include multiple cameras, infrared cameras, thermal cameras, electromagnetic cameras, and the like.

Figure 7:
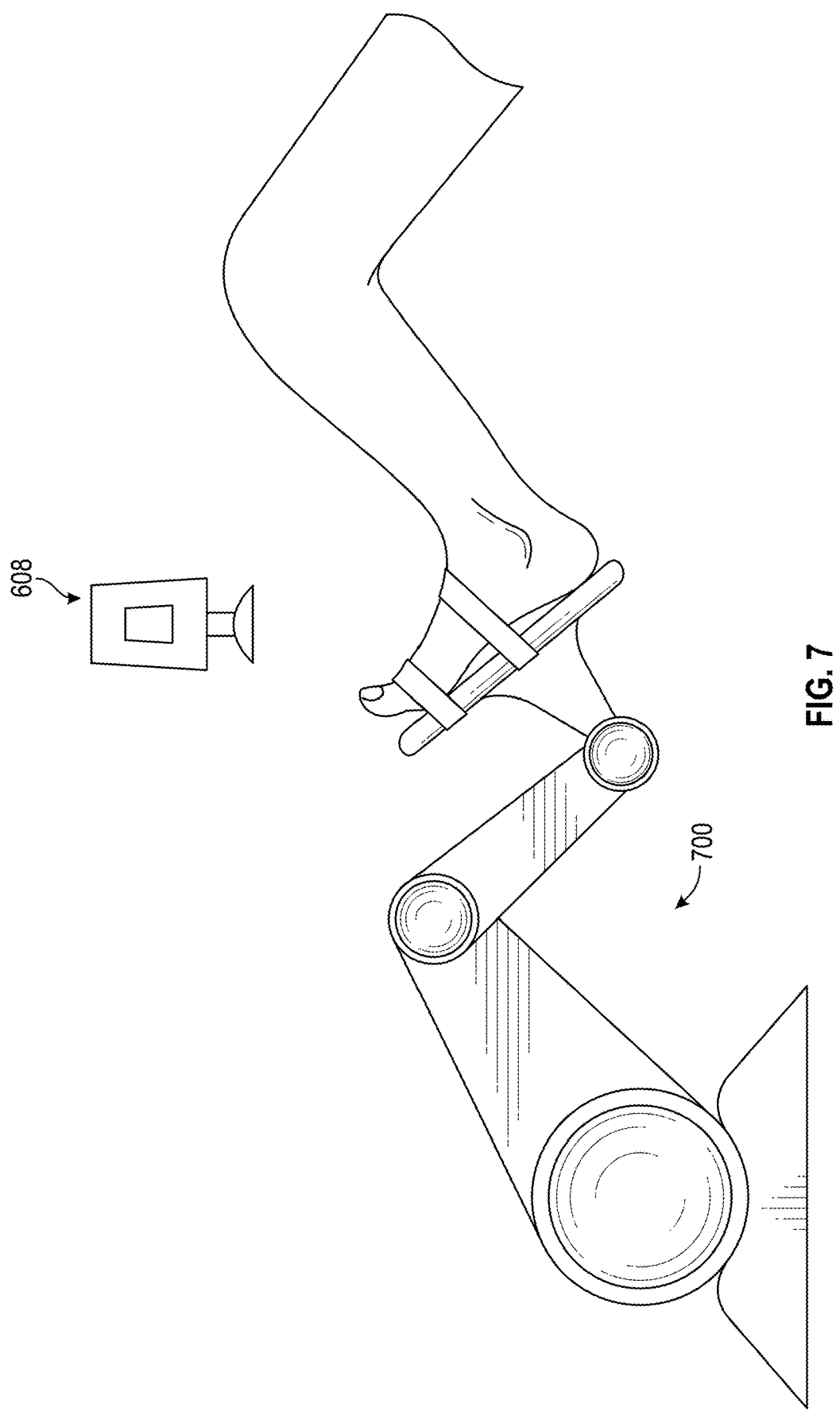

Other controllers include those created specifically designed for the purpose of physical rehabilitation. The devices are designed to provide resistance and/or actively stretch the treatment site, as illustrated by device 700 in FIG. 7. This is done with motors, magnets, electromagnets, pneumatics, hydraulics, piezoelectric breaks, and/or like methods. For example, the device may be used as a pressure controller, where the patient actively moves and the device provides resistance. In an aspect, the device is actively driven by the VR system to manipulate the joint or body part under therapy.

Figure 8:
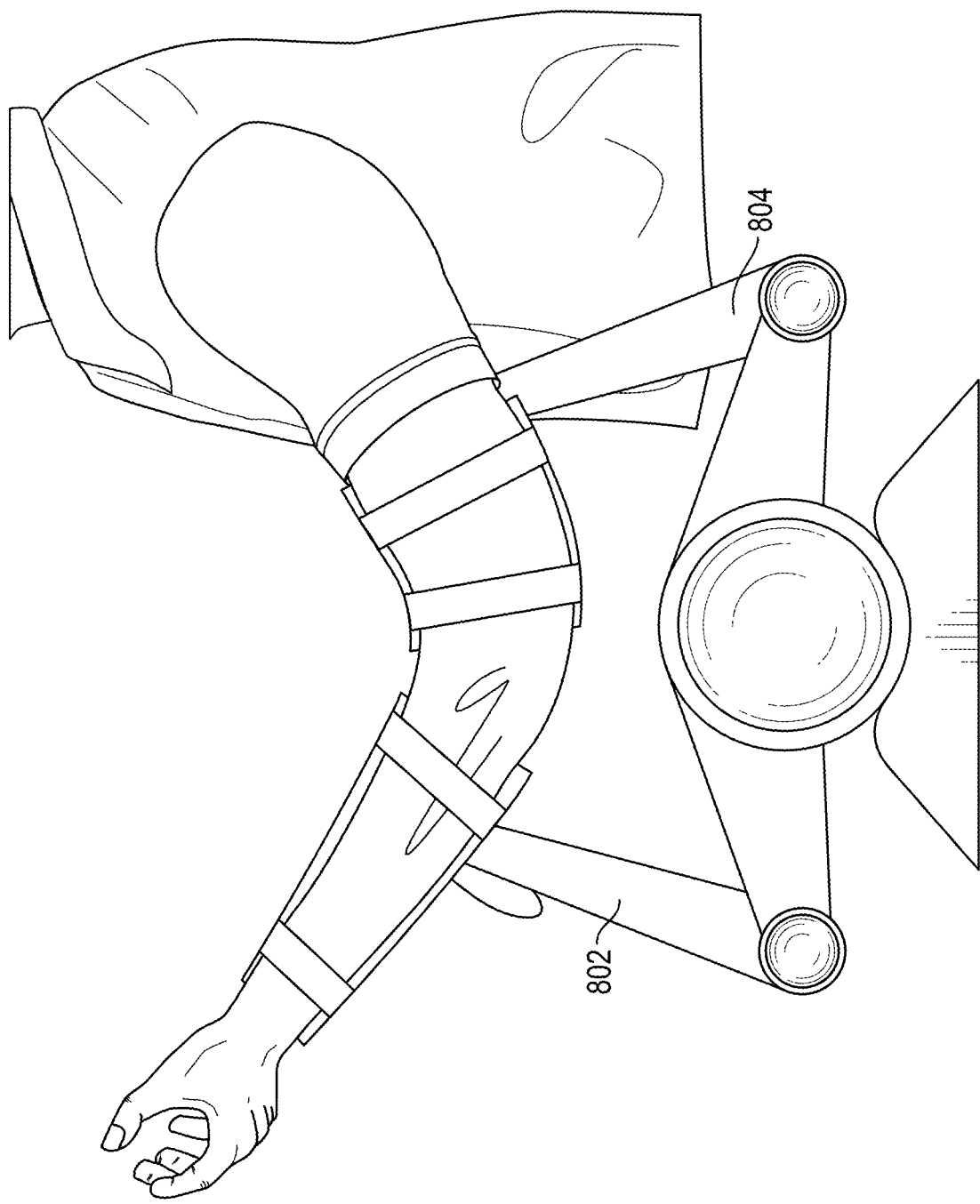

In an embodiment, the device is a multi-axis controller attached to the area being treated, as illustrated in FIG. 8. For example, multiple manipulators 802, 804 may be attached to the same joint. The degree of freedom would be based on the joint being manipulated, for example. In an embodiment, arm (e.g., manipulators 802, 804) movement is linked. In another embodiment, arm movement is independent.

Figure 9:
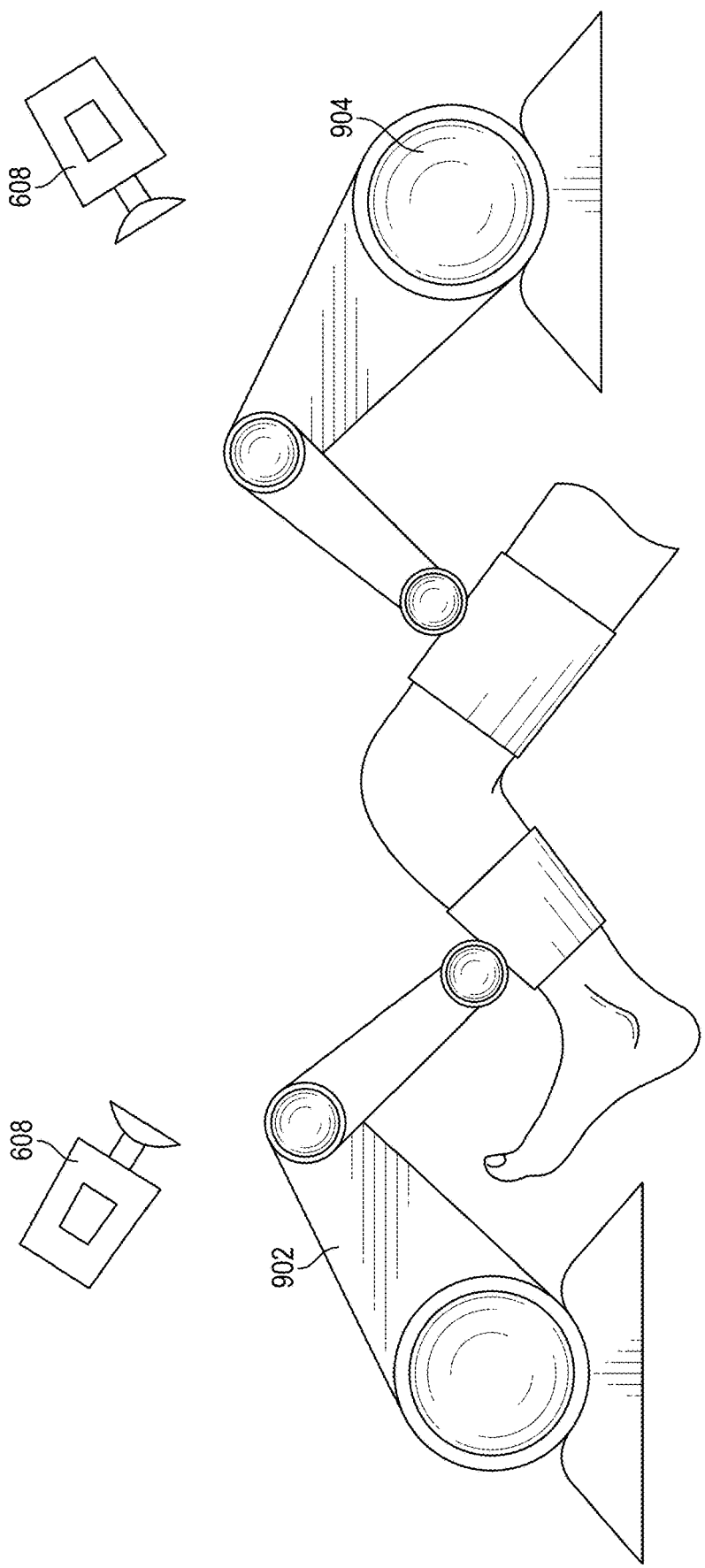

FIG. 9 illustrates an embodiment of aspects of the VR system in which a plurality of controllers 902, 904 are used in combination. As illustrated, one controller 902 is coupled to a lower leg portion of the patient and another controller 904 is coupled to an upper leg portion of the patient. In an embodiment, sensors (e.g., position sensors, patient monitor sensors 102, etc.) are embedded in one or more of the controllers. In another embodiment, position is obtained from external sensors 608 (e.g., cameras, patient monitor sensors 102, etc.).

Figure 10:
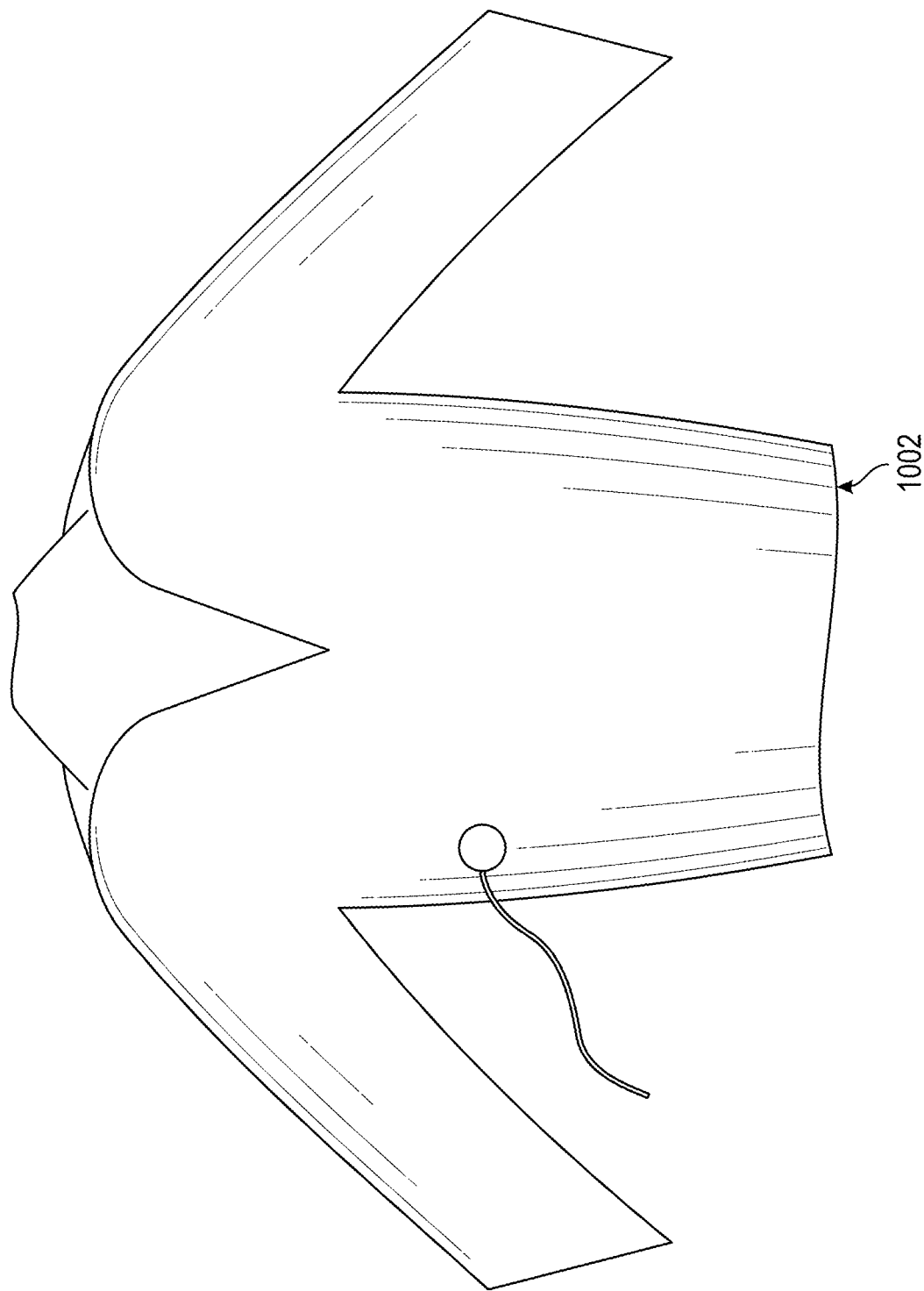

FIG. 10 illustrates an embodiment of aspects of the VR system in which shape memory, alloy, polymers, electroactive polymers (EAP), piezoelectric elements and the like are embedded into one or more articles of clothing 1002 and used with the VR system to provide resistance and/or manipulate joints. In an embodiment, the patient wears clothing articles with memory fiber and the like that coach and/or force the patient through the correct posture. In another embodiment, the controller is moved in a pattern that forces the patient through a series of stretches while the visuals of the virtual reality (e.g., HMD 604) shown to the patient are designed to calm the patient, promote stretching and/or compliance, and the like.

Figure 11:
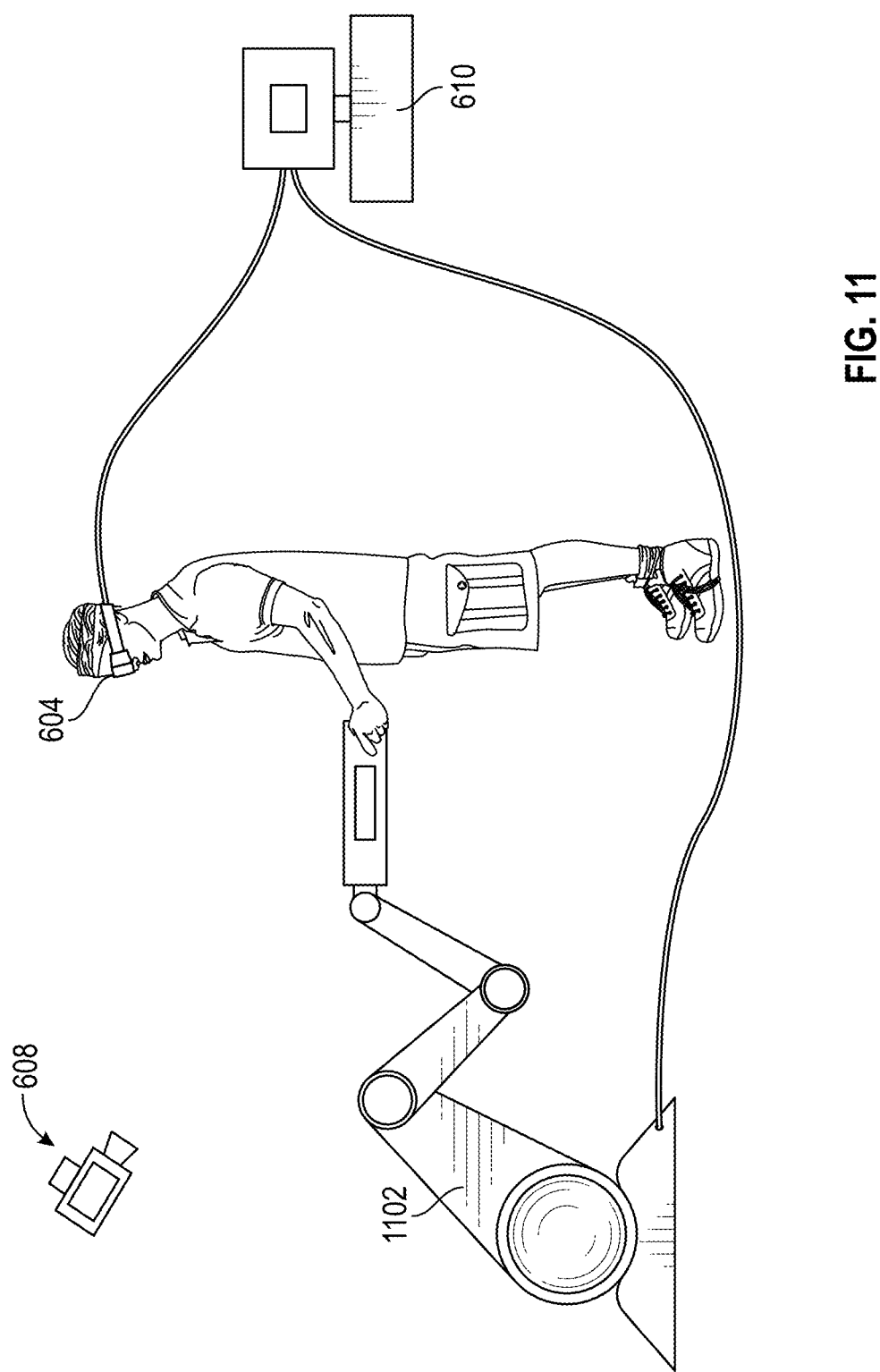

FIG. 11 illustrates an embodiment of VR system including a controller 1102 that allows the patient to manipulate a device with the patient's hands. Depending on the sensors, the controller 1102 can simulate different items. If the therapy was for occupational therapy, for example, the VR system may operate to enable the patient to think they are lifting a box. In an embodiment, different weights are simulated by using the resistance of the motors in the controller 1102. In another embodiment, the device includes a series of electrical windings that can be enabled at various strengths. When therapy and/or occupational medicine is performed on a metal plate, the windings are energized at various levels, creating a simulation of lifting varying size and/or weight objects. The VR system adjusts the perceived weight of the object by varying the magnetic field, in an embodiment. In an embodiment, the windings are placed in the floor on the plate in which the therapy takes place. The VR system can also monitor the position of the user's body, using one or more external sensors 608, to ensure the occupational therapy is being performed properly by the user. The VR system may then be able to instruct the user to correct the position of their body accordingly.

Figure 12:
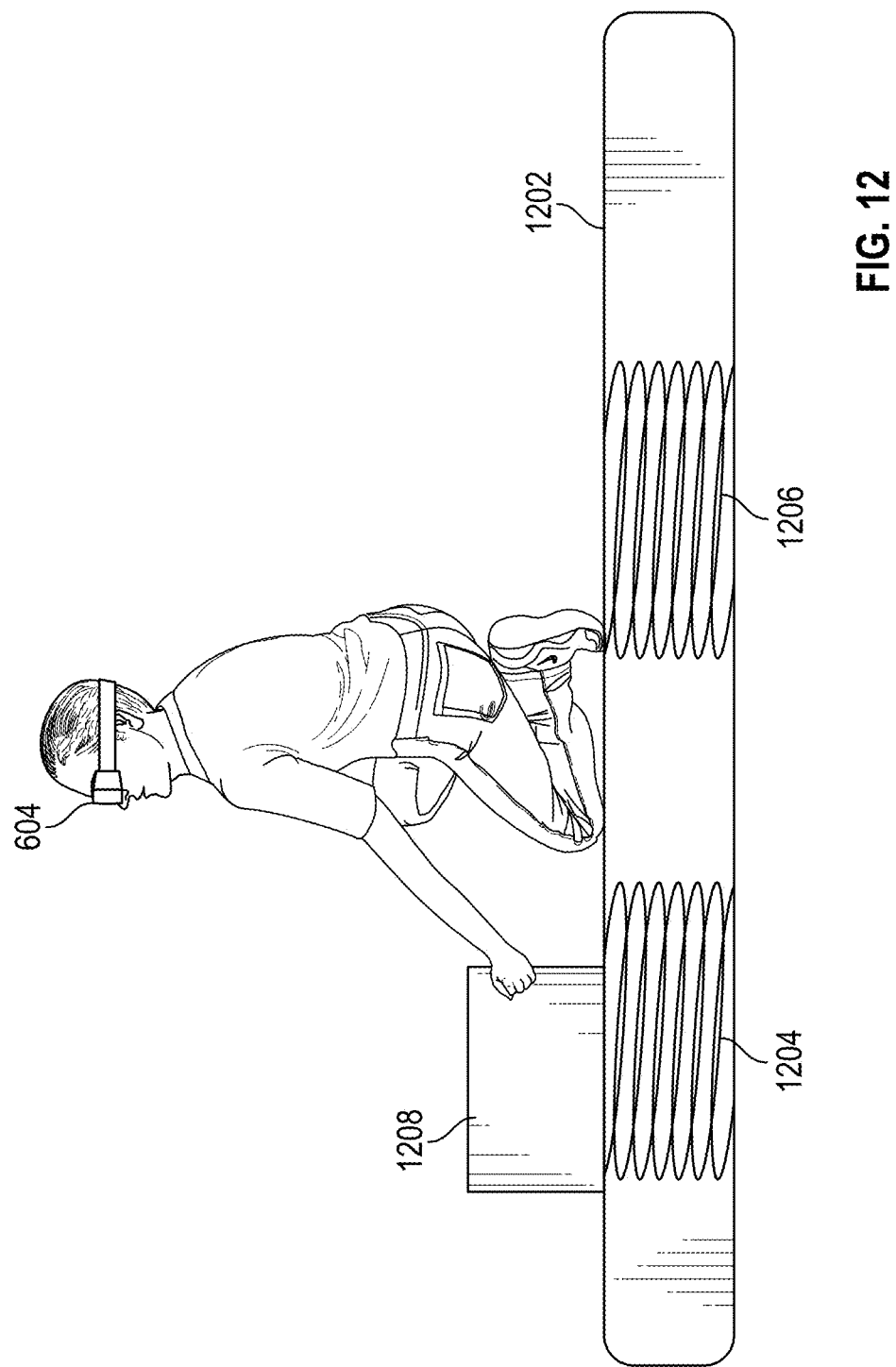

FIG. 12 illustrates an embodiment of the VR system in which a platform 1202 is made with windings 1204, 1206 (e.g., wire coils) in the floor for stretches and/or exercises involving lifting. In an embodiment, the amount of electrical current flowing through the windings is varied with the virtual content displayed to the patient via HMD 604. In an embodiment, the controller varies the current in time with the displayed content to ensure the patient/user perceives body ownership. In an embodiment, the object 1208 (e.g., box, etc.) to be lifted, which may be the controller in one or more embodiments, is made of a material that is affected by the magnetic field generated by the windings 1204, 1206. In another embodiment, the magnetic field is reversed to repel the object 1208. In yet another embodiment, shoes and/or articles of clothing worn by the patient are comprised of materials that can be manipulated/affected by the magnetic field. In an embodiment, the VR system utilizes object 1208 and/or the magnetic field generated by windings 1204, 1206 to simulate different weights, textures, positions, forces by a therapist, and the like.

In addition to monitoring the user's heart rate and blood pressure through traditional methods, the user's retinas are monitored using a camera mounted in the HMD 604, in an embodiment. In this embodiment, changes in blood flow and dilation of the retinas are used to determine blood pressure. In addition to blood pressure, the system is capable of monitoring excitement, sadness, other emotions, response to pain, and the like. Monitoring these reactions could be used to pace conversations and augment interactions with virtual constructs in an AI environment (e.g., AI system 104). A user's negative response to a construct would be a trigger for the construct to change pace, pitch, tone of the conversation, and the like. This would allow the user to have a more relaxed interaction with aspects of the system. Sensors, as further described herein, are integrated into the eye surrounds and the head strap of the HMD, in accordance with one or more embodiments. The blood pressure readings could be an absolute measurement or a differential measurement. These measurements could be taken in real time and changes in blood pressure and/or heart rate could be used by the AI system 104 to monitor and diagnose conditions. In addition to the using the direct measurements, changes in blood pressure and/or pulse in response to certain questions and/or other stimuli could indicate a false answer (e.g., prescription drug abuse, etc.).

In addition to the use of systems and methods described herein in medical applications, the described systems and methods may also be used for direct marketing purposes and the like. By monitoring the user's response to video, virtual reality, augmented reality being watched, and the like, AI system 104 creates a profile for the user. Positive responses to stimuli would be recorded and content and/or commercials are created based off the user's profile. For example, if a user had a positive reaction to cars in general, then content or storylines for cars could be used. This could work on a more specific level, such as if the user had a positive reaction to a certain brand of car then the video content could be modified to use more of that brand, or commercial for local dealers of that brand could be displayed to the user. This information may also be used to recommend new content for the user to watch. In addition, a response to a commercial advertisement may trigger more information to be sent to the user via phone, email, traditional mail, and the like. The information may also be used to create a database of user interests.

In an embodiment, differential blood pressure is measured using an ultrasound device placed on a user's finger and/or a stationary device similar to a fingerprint reader, for example. In addition to the pressure, other attributes of the blood flow are monitored, such as turbidity rate using Doppler, and the like. These sensors may be integrated into a watch or ring, as further described herein, for constant monitoring and the information may be stored and/or transmitted for further analysis (e.g., by AI system 104) or the information may be analyzed (e.g., by AI system 104) in real time.

Other aspects of the disclosure provide a home therapy device to patients struggling with vision related diseases (e.g., Age-Related Macular Degeneration, Histoplasmosis, Cataracts, Diabetic, etc.). This device will track progress and adapt the test to best fit each patient's disability. In an embodiment, this device includes HMD 604 and/or other aspects of the VR system in communication with AI system 104 and/or other aspects of system 100. The eye monitoring and vision enhancement systems and methods described below are exemplary and non-limiting.

In an embodiment, this device is a home-use device that will fit over the user's face to do routine eye exams and/or provide crucial and/or regular monitoring of the eyes. The device uses software that adapts to the patient's need and will provide regular reports to the user via a portable display, PC, and/or cell phone app. The device may also provide direct feedback to the healthcare provider (e.g., ophthalmologist, etc.). This feedback allows the healthcare provider to monitor the progress of a treatment and/or to inform the provider of negative setback that could require immediate attention.

The device, in an embodiment, is comprised of a goggle-like device that is placed over the eyes, a display, and a mouse/pad. The goggle device displays information to the patient in the central and peripheral regions. Software would run through a series of tests (e.g., Amsler Grid, Automated Static Perimetry, Non-Contact Tonometry test, Eye Vision Exam, Optical coherence tomography (OCT), etc.) based on the patient's diagnosis to monitor and track the patient's progress. During certain tests, the user gives feedback. The feedback will be generated through the mouse/pad and/or other input device and sent to the goggles via wire and/or wireless communication channels. One example would be during the Amsler Grid test the user would be required to indicate which areas of the grid are distorted and which parts of the grid are actually missing by drawing a line with the mouse/pad. Another example would be during the Automated Static Perimetry exam the user would be required to press or tap the mouse/pad to indicate when a light can be seen. The test results are compiled into a report that is displayed to the user and/or sent to the healthcare provider.

This device enables regular monitoring of eye related diseases. Eye related diseases are often complex and difficult to know when treatments are not working as expected. This device enables users to keep records of progress in terms of days and weeks instead of months. Doctor appointments are pricey and specialists (e.g., ophthalmologists) are often difficult to get immediate appointments. Patients struggling with AMD are often provided with an Amsler grid to monitor progress of the disease but many times it is difficult to track progress from day to day using a paper sheet and there is variability of results due to distance from the sheet and room lighting. Many times the patient doesn't realize a change in vision until the next appointment and by then the bleed or scaring in the back of the eye could be pretty significant.

Regular monitoring of the eyes. In an aspect, this device allows the user to track progress of their vision on a regular basis. Many times users meet with the healthcare provider on a monthly basis or even worse only several times a year. Between these appointments, the device would monitor and track the progress of vision and inform the patient and/or health provider when a more immediate appointment is required.

Integration of multiple tests. In an aspect, this device integrates multiple tests into the goggle software (e.g., Amsler Grid, Automated Static Perimetry, Non-Contact Tonometry test, Eye Vision Exam, Optical coherence tomography (OCT), etc.). Conventional cellular phone applications allow users to test and track their Asmler Grid test and Eye Vision Exam, but these applications lack constancy (e.g., distance of phone from patient, etc.) and don't adjust to each patient's needs (e.g., based on eye disease and progression, etc.).

Figure 13:
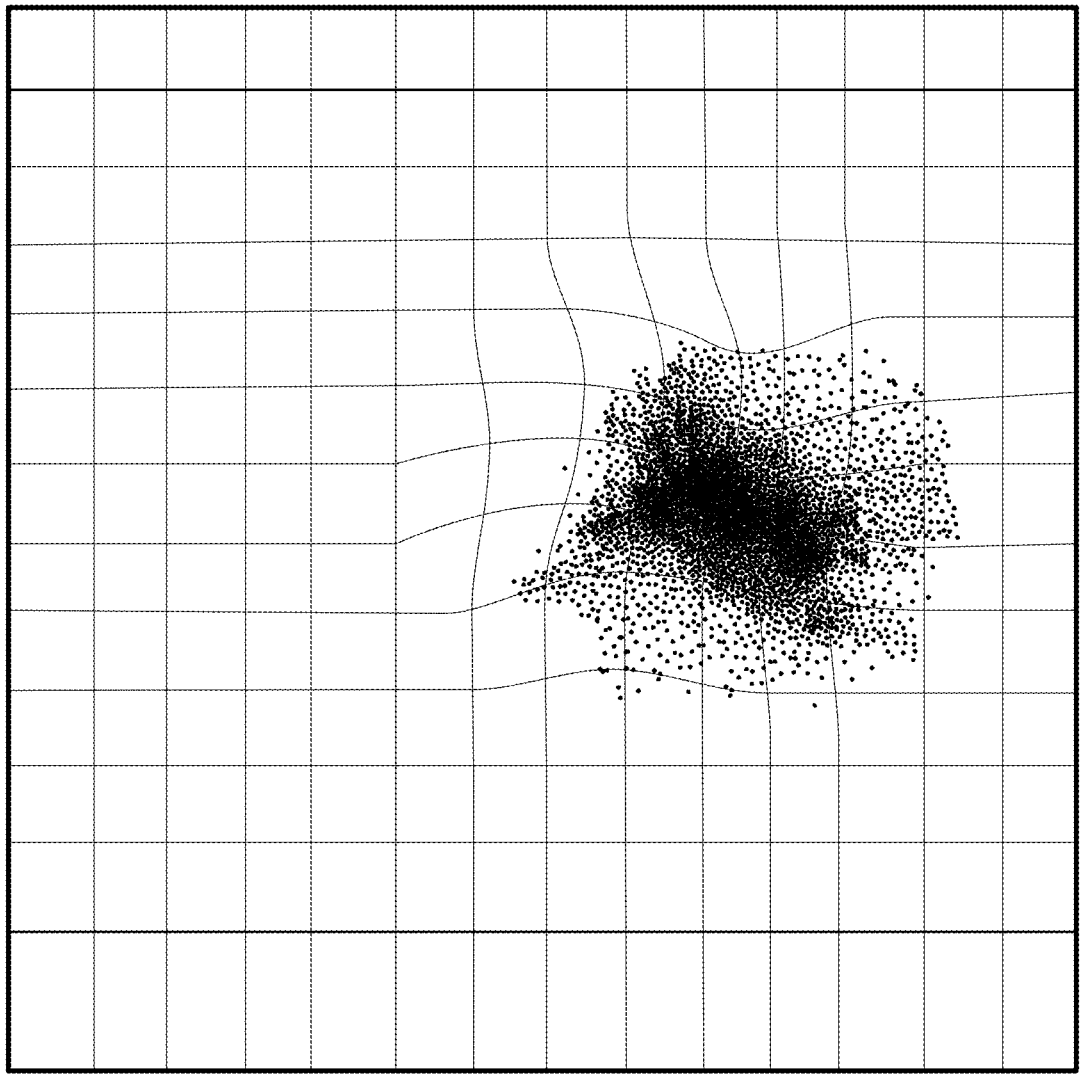
FIG. 13 is an image of an Amsler Grid showing a large scotoma encroaching on the central fixation.
Figure 14:
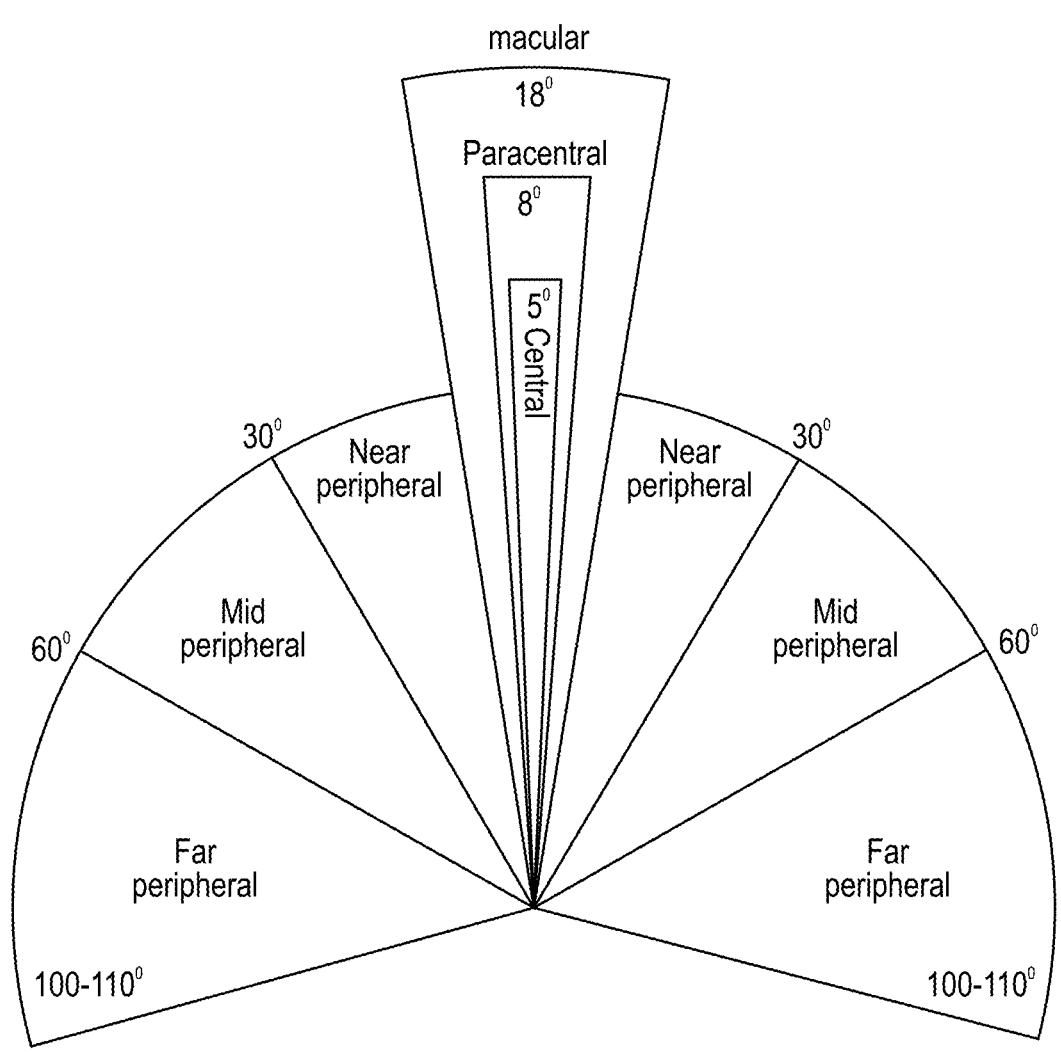
FIG. 14 is an image of the peripheral vision of the human eye.
Figure 15:
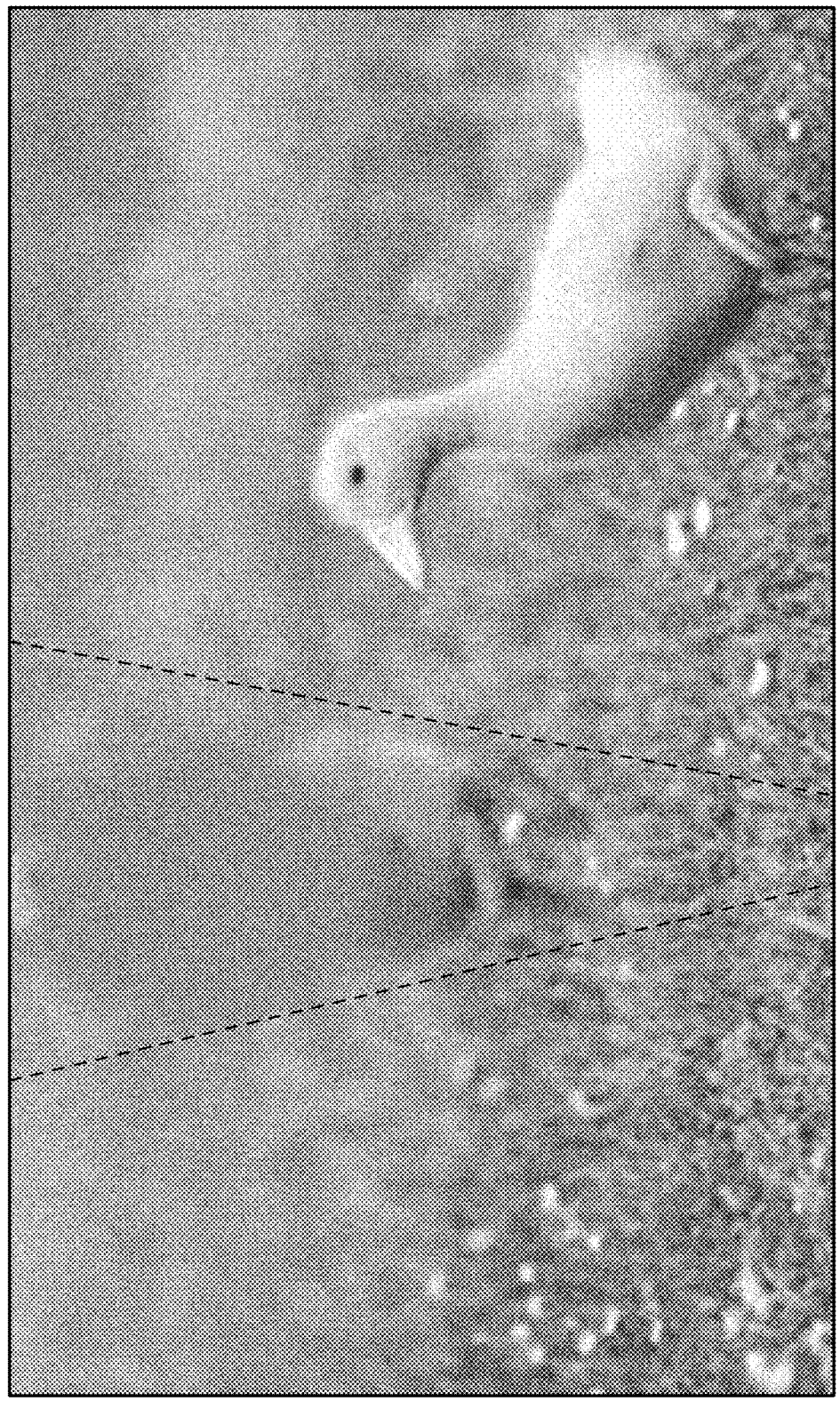
FIG. 15 is an image of scotoma affecting vision.
Figure 16:
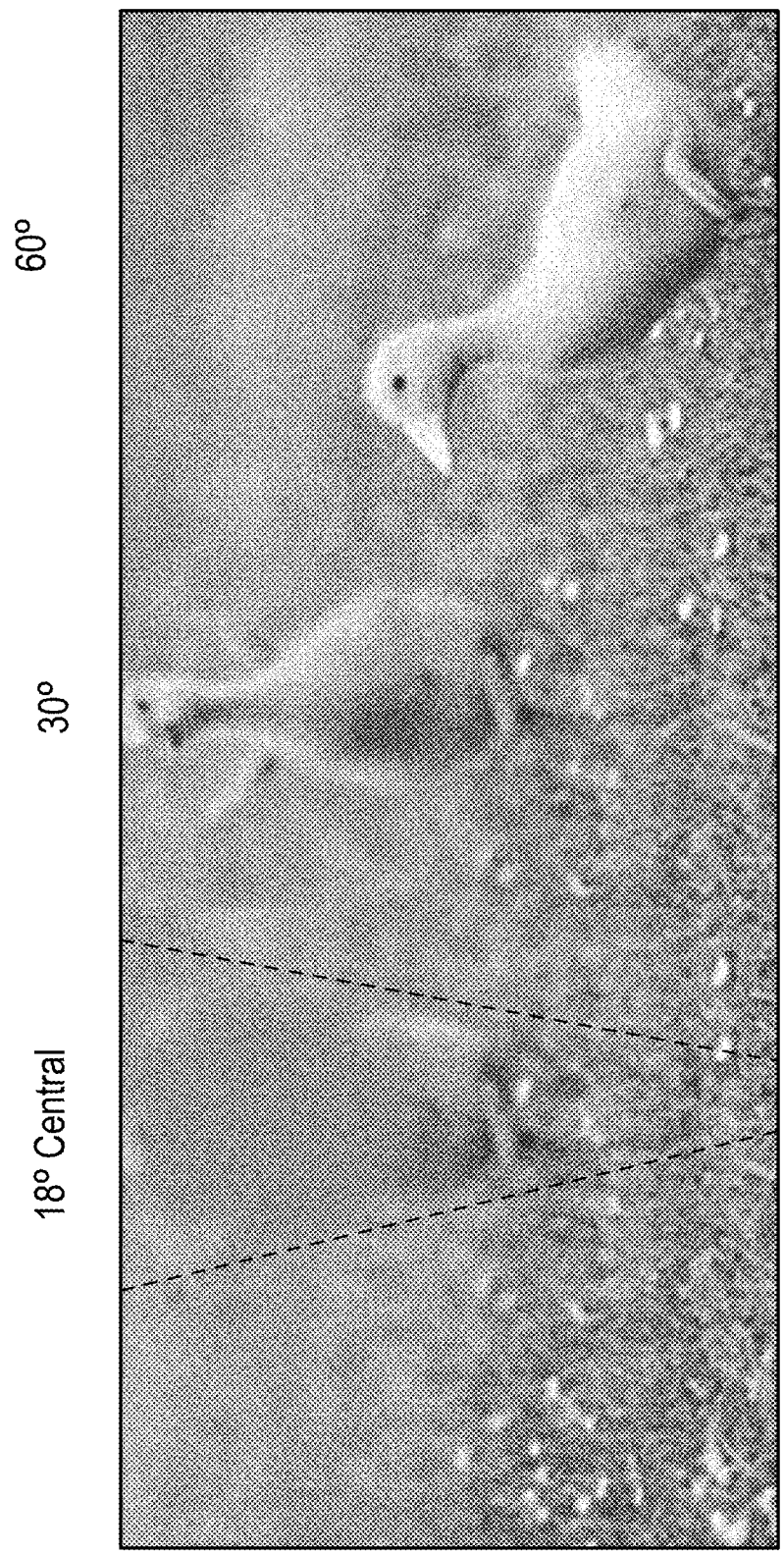
FIG. 16 is a modified image to correct for scotoma according to an embodiment.

Additional Enhancements. The goggles may also be used to enhance vision. Magnify. In an aspect, the user uses the goggles to magnify objects they are looking at by using a camera lens and displaying the object larger on the display. Blurry Vision. Some diseases cause blurry vision due to protein buildup that clouds the eye lens. In an aspect, this device enables the patient to adjust the image on the goggle display to include outlines that define objects in the room. Though in these cases vision cannot be restored, this device would help patients function in their household. Scotoma (defect within a field of vision—blind spot). In the case of the patient suffering from AMD, the patient may suffer from scotoma (FIG. 13), a partial loss of vision, or a blind spot in an otherwise normal visual field. FIG. 13 is an image of an Amsler Grid showing a large scotoma encroaching on the central fixation with some distortion. In an aspect, this device would require the user to indicate the scotoma area. Once the area is determined, the camera data is adapted to allow that area of data to be moved into the peripheral field to allow the user calibrate based off the eye test report and display the image to best suit the patient's needs. In a case where the central vision is missing, the image in the central vision may be displayed in the peripheral location (FIG. 14). FIG. 15 is an image of ducks with a scotoma affecting the vision of the duck on the left side. FIG. 16 is a modified image after visual data is manipulated in accordance with systems and methods described herein with the patient's scotoma data.

Figure 17:
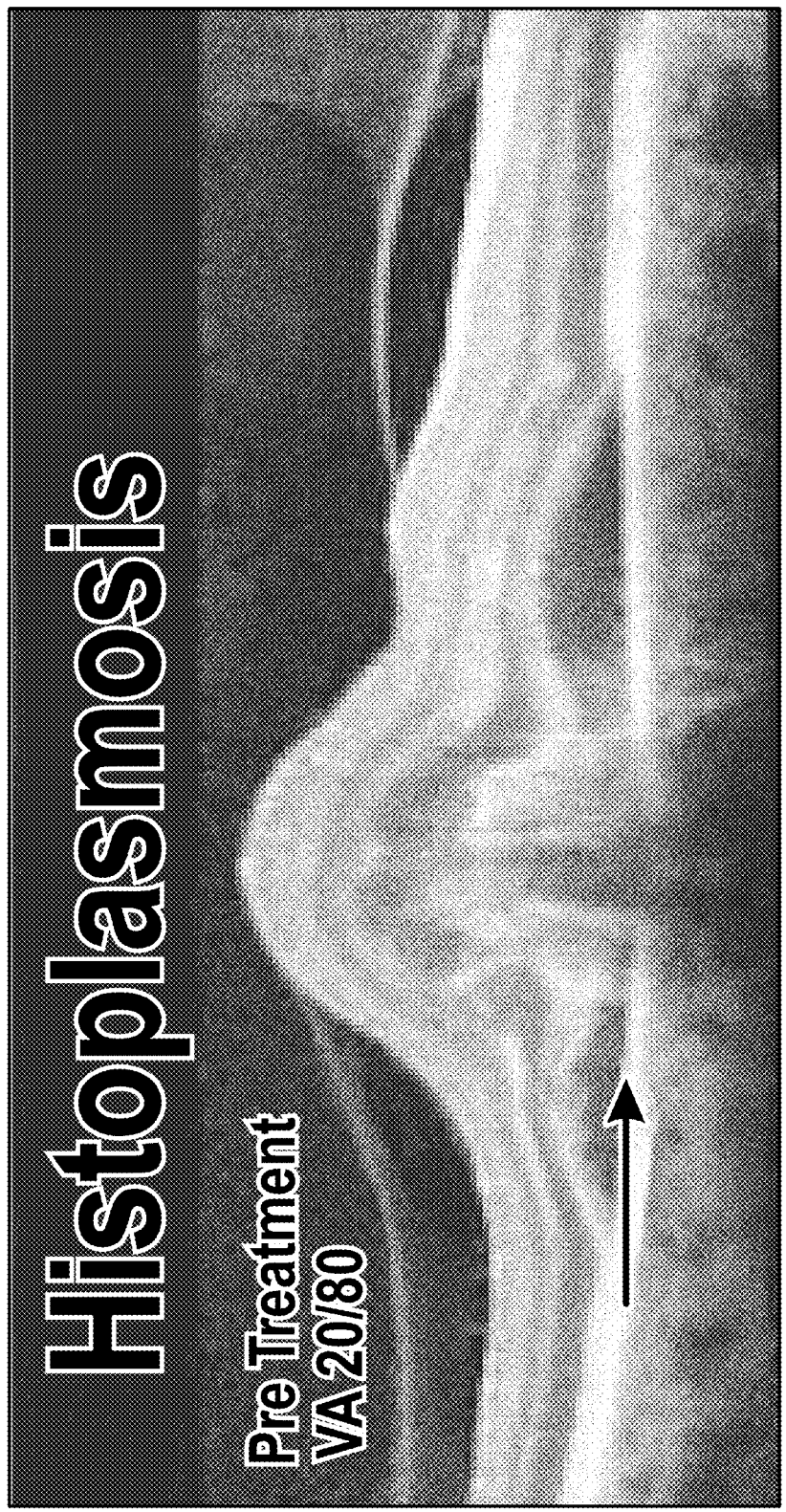
FIG. 17 is an image of a histoplasmosis scar.
Figure 18:
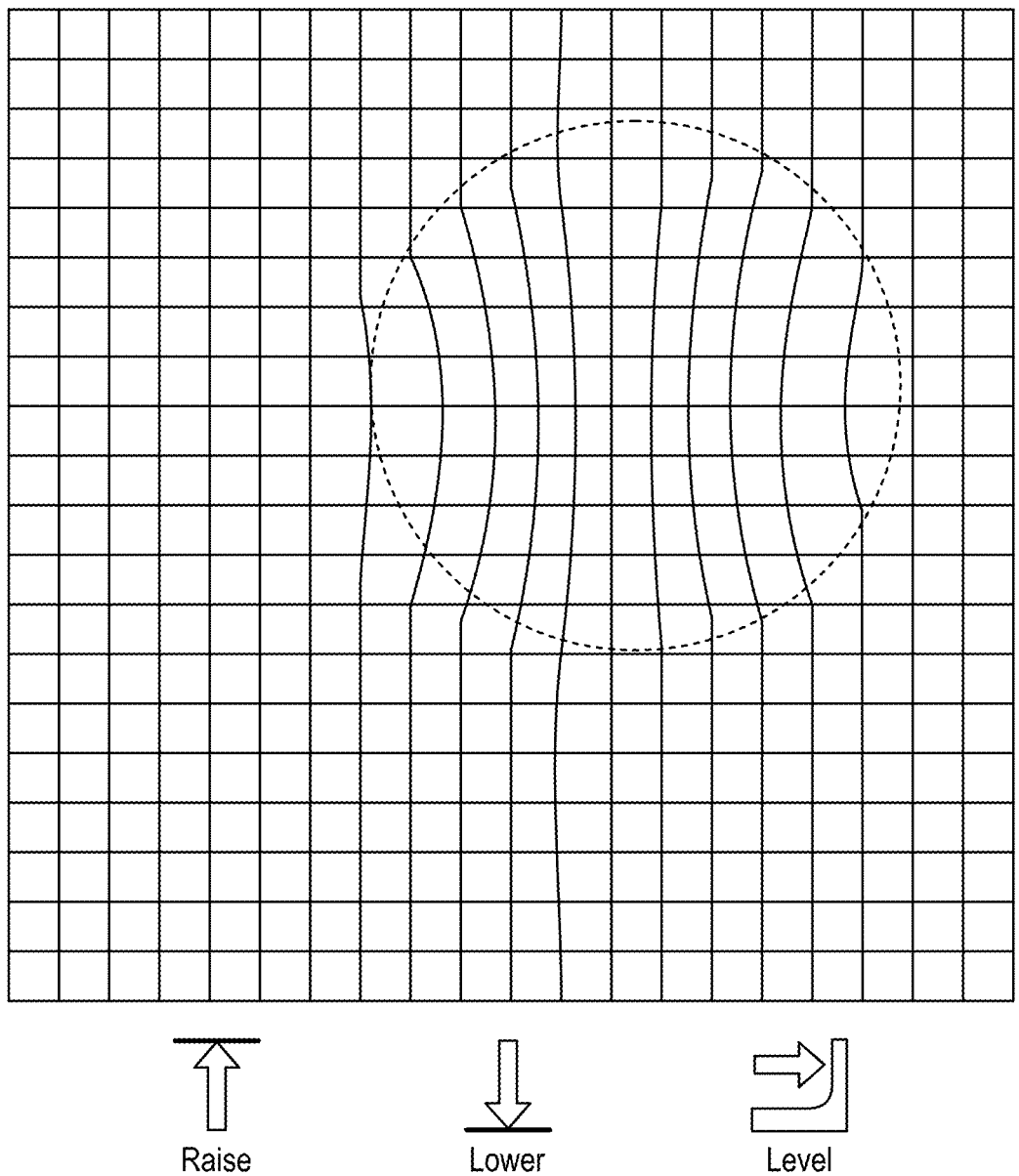
FIG. 18 is an image of vision distortion caused by the scar of FIG. 17.
Figure 19:
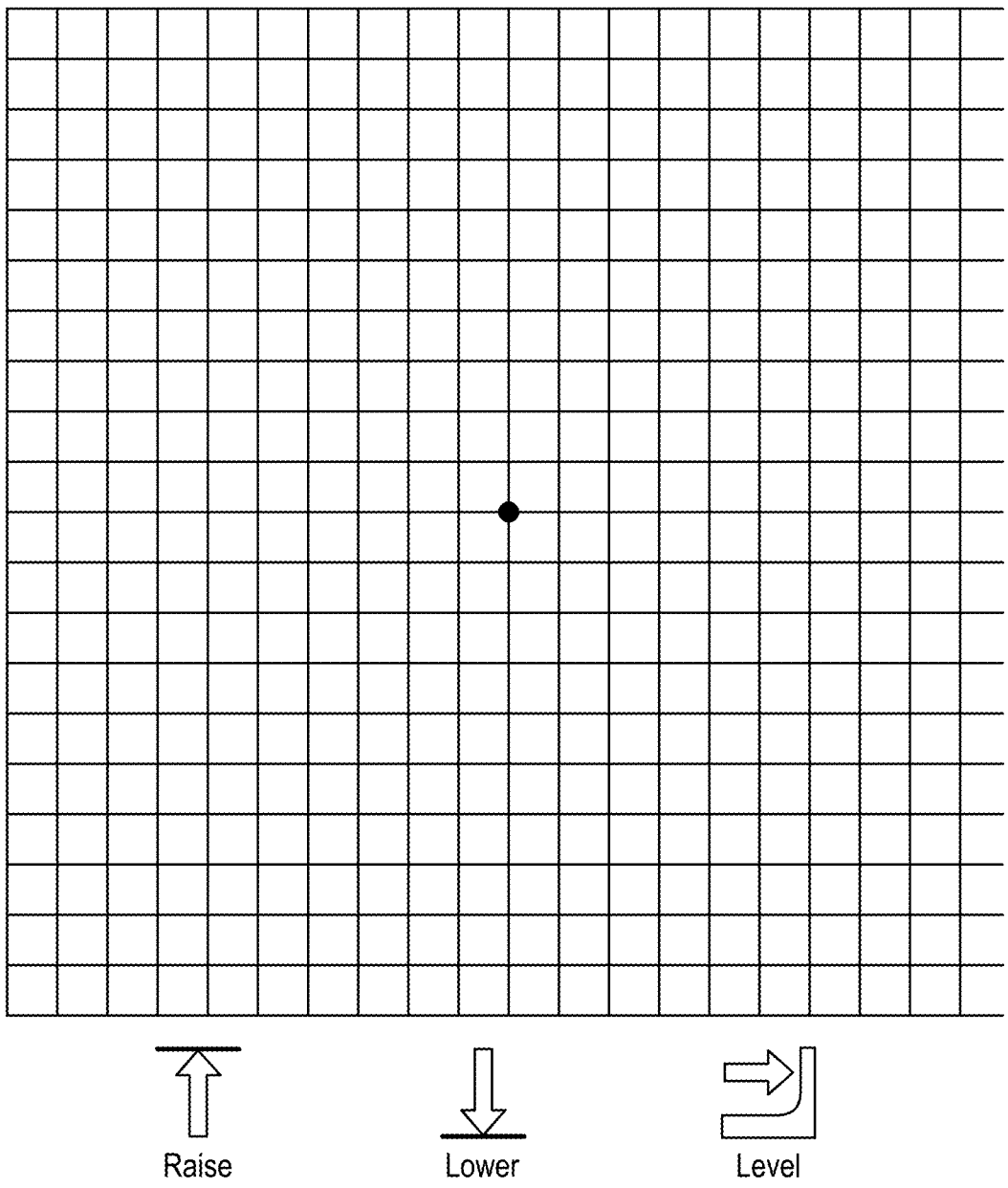
FIG. 19 is an image of adjusted vision distortion with a filter according to an embodiment.
Figure 20:
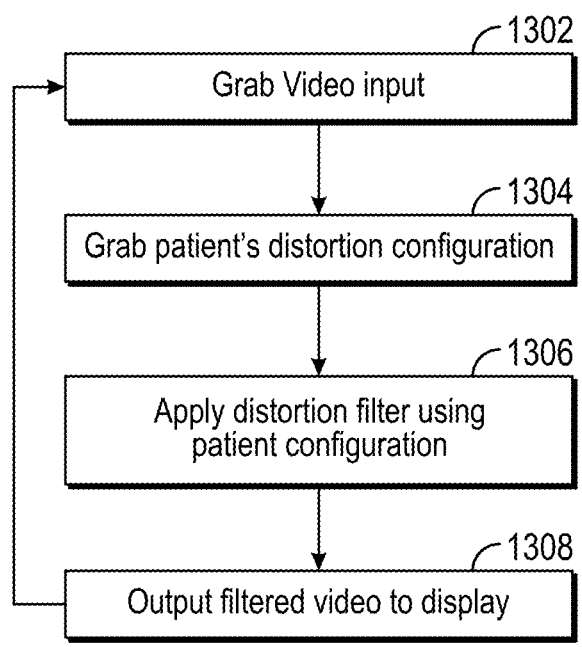
FIG. 20 is a flowchart of an exemplary algorithm for filtering camera data according to an embodiment.

Distortion Filter. In the case of histoplasmosis scaring, the vision can be distorted as seen in FIG. 18. The distortion is caused from the height of the scar (FIG. 17). In an embodiment, the user adjusts the Asmler grid lines until the lines are straight so that the algorithm of the display distorts the camera data in such a way that the user sees clearly. For example, the patient may select a gradient tool and focus the mouse/pad over the distorted area and make adjustments to distort the image back to the straight line grid (FIG. 19). In this manner, the camera data is filtered to adjust the image to counter the distortion caused by the scar. Additionally or alternatively, results from the distortion test in accordance with an aspect of the disclosure are used to generate lenses for corrective glasses that compensate for distortion. FIG. 20 is a flowchart of an exemplary algorithm for filtering camera data to adjust the image to counter the distortion caused by the scar. At 1302, the computing device executing the algorithm grabs the video input. At 1304, the computing device grabs the patient's distortion configuration. At 1306, the computing device executing the algorithm applies a distortion filter using the patient's configuration. At 1308, the computing device outputs the filtered video to a display device for viewing by the patient.

Figure 22:
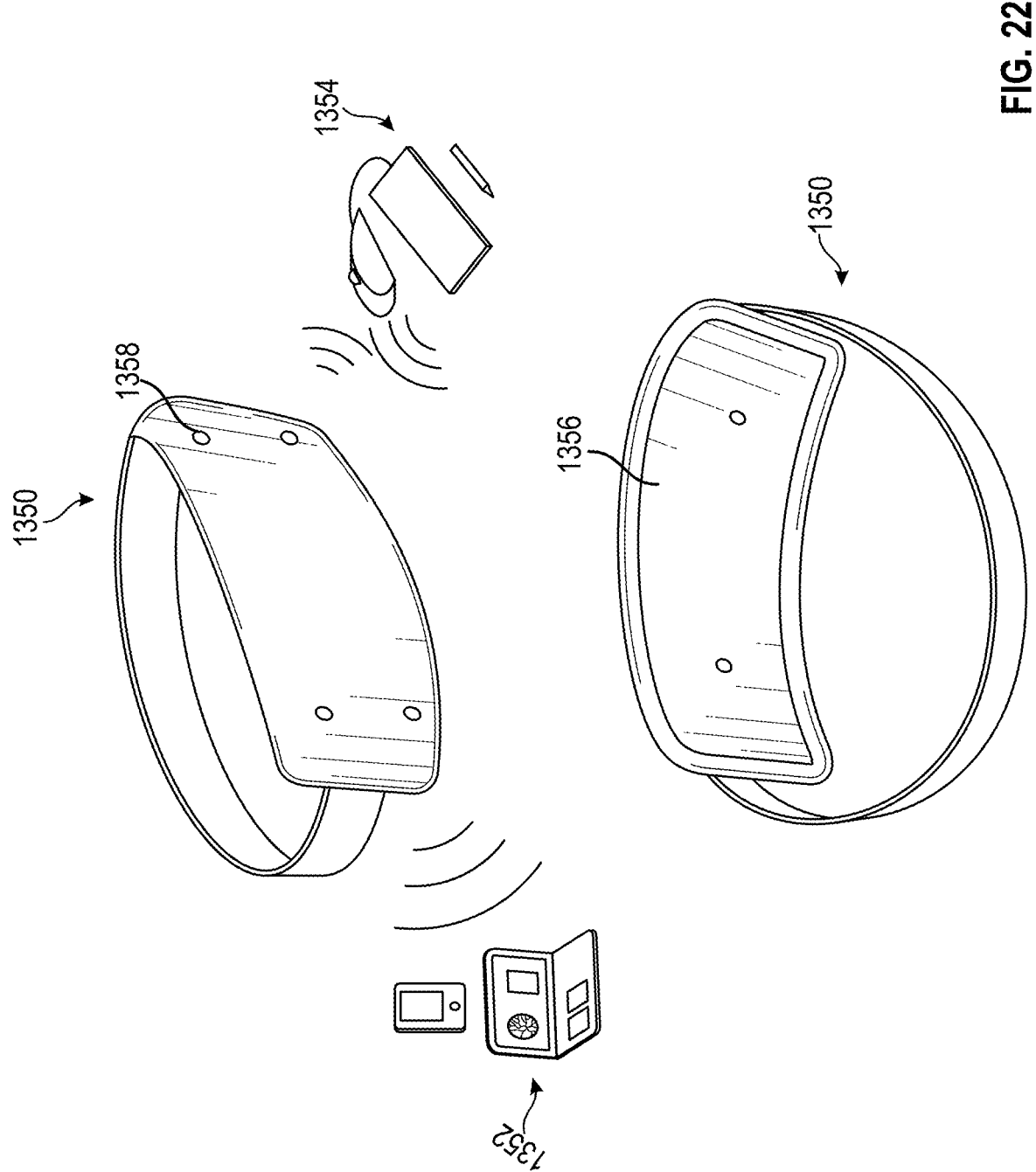
FIG. 22 is an image of an exemplary goggle device (front and rear view), display, and mouse/pad according to an embodiment.
Figure 23:
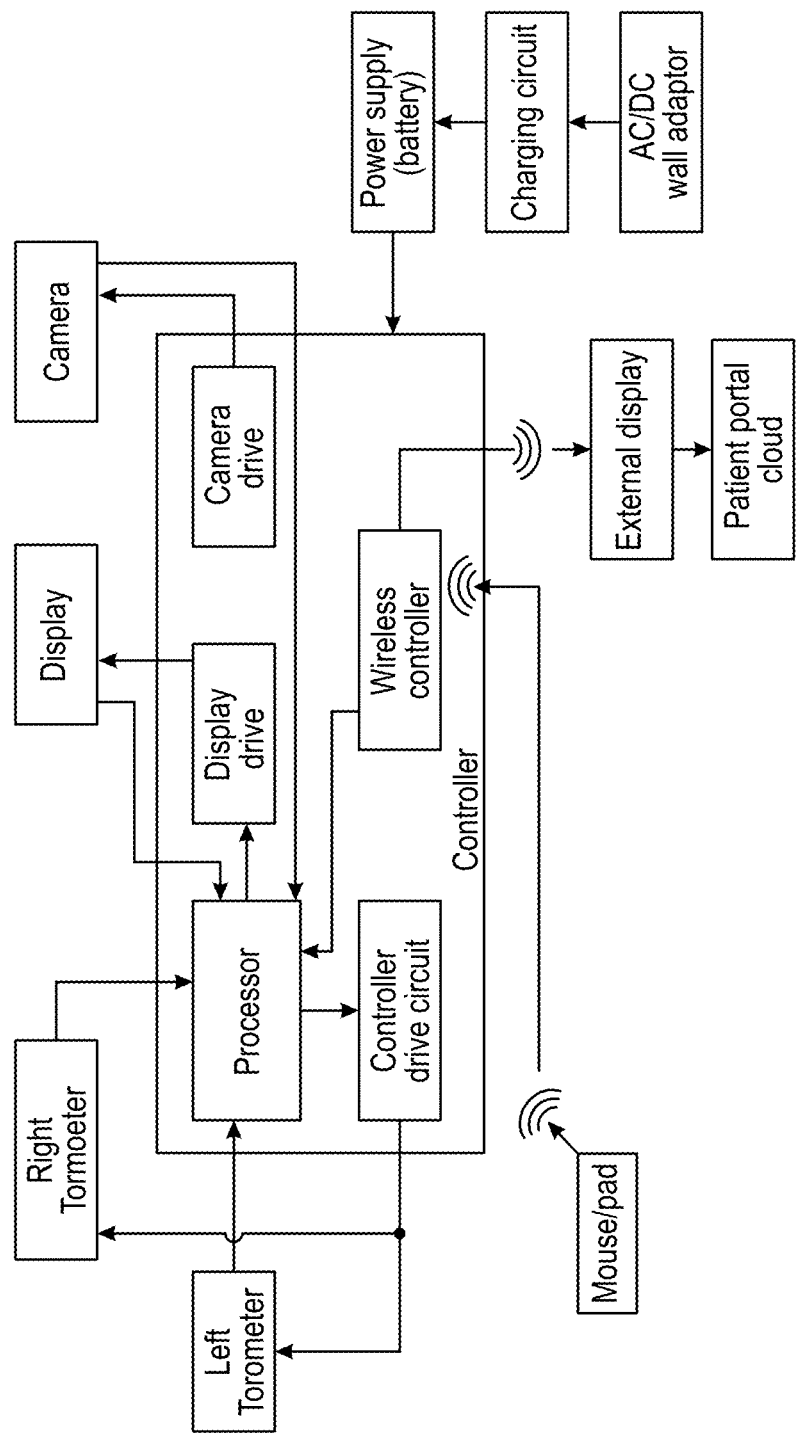
FIG. 23 is a block diagram of an exemplary goggle device controller method and system according to an embodiment.

In an embodiment, the eye monitoring and vision enhancement device includes a goggle device 1350, an external display 1352, and a mouse/pad 1354 for user feedback, as illustrated in FIGS. 22 and 23. In an aspect, the goggle device 1350 includes a display 1356 that fully covers the wearer's (e.g., patient's) eyes to provide an image to the patient in the central and peripheral vision of the patient. The goggles 1350 use software that is configured to perform one or more tests based on the patient's diagnosis. Each test will follow the patient's individual progression of the eye disease and adjust (e.g., optimize, personalize, etc.) the test to best fit the patient's needs. The goggles 1350 also include camera lenses 1358 that provide visual data to the controller (e.g., processor) in the goggle device where the visual data will be manipulated based on the needs of the patient (e.g., improve image, magnify image, etc.). In one embodiment, the device 1350 may also include one or more thermal sensors configured to detect the possible onset of infection.

Display 1356: In an embodiment, the display comprises a tablet computing device, a laptop computing device, a cellular phone, a smartphone, a display monitor, or the like. In another embodiment, the display monitor 1356 is integrated into the goggle display. The goggle device 1350 sends the patient data to be displayed to the display device via a wired and/or wireless communications connection.

External Display 1352: In an embodiment, the goggle controller sends patient data to the external display (e.g., tablet computing device, personal computer, cellular phone, etc.) via a wired and/or wireless communications connection. This data is compiled into one or more reports to help the patient understand the progression of the disease. The data may also be sent to an external patient portal cloud for the healthcare provider to remotely monitor the patient's progress.

Mouse/Pad 1354: In an embodiment, the mouse/pad includes a pad with a stylus pen, a plain mouse, or the like. This device 1354 is used to allow the user to provide feedback to the goggle device 1350. The mouse/pad 1354 is connected to the goggle device 1350 via a wired and/or wireless communications connection. The mouse/pad 1354 may be any input device, such as a touchscreen and/or any input devices described herein, for example.

Additionally or alternatively, the eye monitoring and vision enhancement device 1350 is used after eye surgery to help restore vision faster and also to help sharpen images for patients that are partially blind and/or have clouded vision.

Figure 21:
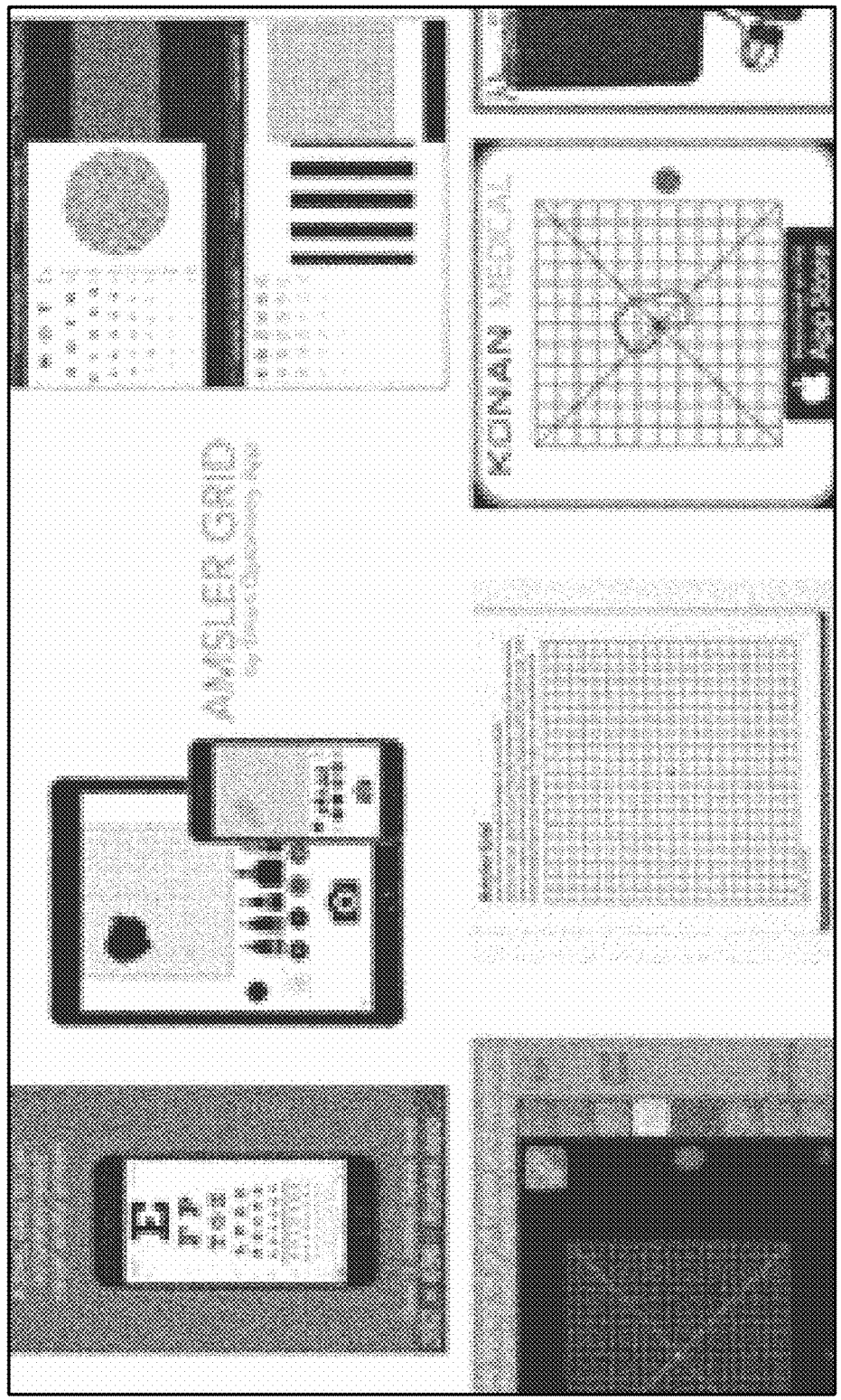
FIG. 21 is an example of conventional cellular phone apps that provide vision testing and/or Amsler grid progression testing.

Conventional cellular phone apps that provide vision testing and/or Amsler grid progression testing (FIG. 21) lack the consistency of distance from the patients eye and are difficult to use. For example, users report difficulty focusing their eyes on the dot when their finger is trying to draw a line to the distortion in conventional Amsler Grid testing apps. Moreover, reports indicate that about 11 million Americans have AMD and that injections can cost between $50 and $2,000. For example, reports claim that Medicare paid $1 billion for 143,000 patients using Lucentis. Conventional techniques do not provide means of tracking how often patients really need injections. Conventional techniques require patients to visit the healthcare provider on a regular schedule (e.g., every 1-2 months) but there is no way of tracking progress other than what the doctor reports.

Another embodiment in accordance with aspects of the disclosure includes monitoring a user's voice for audio irregularities that indicate, for example, awareness, deception, intoxication (e.g., slurred speech, etc.), or the like. The speech is monitored by a smart phone, a tablet computing device, or a dedicated computing device as further described herein. In an embodiment, a microphone input is operatively coupled (e.g., electrically, communicatively, etc.) to a digital-to-analog converter (DAC). The internal microcontroller (e.g., graphics processing unit (GPU), central processing unit (CPU), digital signal processor (DSP), etc.) then performs a Fourier Transform or Fast Fourier Transform (FFT) of the incoming (e.g., real-time) or prerecorded audio sample. The sample is analyzed for shifts in frequency over time and these shifts are recorded to establish patterns and/or baselines. Time domain analysis of the audio input is used to establish changes in tempo or attack based on the envelope of the signal. In addition to monitoring the audio input, aspects of a system in accordance with an embodiment of the disclosure monitor video and/or other sources simultaneously or asynchronously to enhance the ability for detecting changes. When monitoring video input, the entire video frame may be monitored, or alternatively, specific locations in the frame may be monitored using machine vision and image recognition algorithms, for example. In an embodiment, the software executing on the microcontroller uses existing application programming interfaces (APIs) to isolate and capture the user's eyes by monitoring the frames and tracking the change in pixels. The filters used to isolate the user's eyes monitor the areas around the user's eye, eyebrows, mouth, entire face, and/or entire body, for example, for shifts and/or movement. The microcontroller may keep the collected information (or electronic data representations thereof) locally (e.g., on a memory storage device electrically coupled thereto, etc.) or may upload it to a centralized server (e.g., communicatively coupled to the microcontroller, etc.). The collected information may be used to compile an expert system that could be used by other users. In another embodiment, crowdsourced information could be used as input for a deep learning and/or machine learning system. The system is configured to solve for (e.g., determine) various conditions including, but not limited to, optimal drug dosing, optimal time to take/administer drugs, optimal time for certain activities (e.g., study, sleep, exercise, etc.), or the like.

Some embodiments, such ones dealing with the delivery of drugs, utilize a closed-loop system to ensure that the selected AI algorithm can produce a correct solution. For example, a system that is monitoring beta blockers could use blood pressure measurements to create a closed-loop system. An alternative embodiment might make indirect measurements through monitoring blood pressure and skin sweat, for example. Other embodiments may require blood or urine analysis to create a closed-loop system. In systems in which the drug amounts and/or delivery times are configured to be modified by an algorithm, systems and methods in accordance with the present disclosure place restraints on the system to restrict the timing and/or dosing within clinically safe levels.

In yet another embodiment, virtual reality is used to implement a post-operative care for a total knee arthroplasty (TKA). The care could be started in the hospital or after the patient has been discharged. For example, a typical post-operative protocol for a TKA focuses on lower extremity exercises, which may include ankle dorsiflexion/plantar flexion, quad sets, hamstring sets, gluteal sets, short arc quad, hip abduction, heel slides, long arc quad, active knee extension/flexion, straight leg raise, and the like. Patients are encouraged to perform these exercised every 2-3 hours while awake. By creating a series game in a virtual reality environment, the patient is guided through a series of actions which will require the patients to perform the required movements to complete the level. The virtual reality environment may require the user to specifically perform each stretch, or it may be implemented in a way in which the patient follows a narrative and the required activities cause the patient to stretch the required muscles. In an embodiment, the motions/stretches of the patient (e.g., leg motions, etc.) are tracked with cameras and/or position sensors, as further described herein. The protocol may be customized by a doctor and the progress of the patient may be tracked (e.g., remotely via a communications network and computing devices as described herein). If a patient does not make sufficient progress during the post-operative stretching, this could be a trigger for an alert (e.g., text message, email, report, smartphone notification, etc.) to be sent to the doctor, physical therapist, insurance agency, or the like. Although this embodiment focused on a post-op TKA, one of ordinary skill in the art will understand that other embodiments and exercise protocols can be implemented for other procedures.

For example, aspects of the systems and methods described herein can provide visual proof, such as via intraoperative pictures or videos or post-operative imaging, to confirm that operative procedures were performed. For instance, an insurance carrier can use the visual proof to validate that the operative procedure was performed and performed to predefined standards, such as by analyzing the pixels of pictures, videos, and/or images. In an embodiment, the systems and methods described herein validate appropriate alignments, tissue removal, and/or tissue repair. Machine learning aspects described herein can analyze pictures, videos, and/or images to confirm. In one embodiment, the machine learning aspects automatically approve or deny operative procedures based on pictures, videos, and/or images that conform to or deviate from a baseline standard. In another embodiment, the machine learning aspects present the automatic determination to a human user to override or confirm the machine learning determination.

One embodiment would use pattern recognition. Another embodiment could implement a Deep Learning algorithm implemented with a Convolutional Neural Network (CNN). This type of AI requires a large number of images to train the system, but can be more accurate than other algorithms. A neural network is created from a network of artificial neurons with discrete layers, connections and data flow. The neurons are trained to perform a task such as automatic image recognition. This can be done using labeled pictures of an object as an input and the output of the neuron being the label. For example during the training of the neuron, the input of an X-Ray of a "left knee" would be label as a "left knee". The more labeled images the neurons are exposed to the more accurate the system becomes. In some embodiments, the system is trained with over 10 million images. Each neuron gives a weighted output which is totaled to give a confidence level of the image recognition. In this example, the system might be 95% confident that the image is a right knee, 10% confident it is an ankle, and 1% confident it is a cat. With increased neurons and layers and large amounts of training, the system gets better at identifying objects. In addition to anatomy, the neurons could be trained to detect surgical implants such as total knee, unicompartmental knee implants, intramedullary rods, dental implants. In an insurance verification system embodiment, when an insurance claim is submitted, a DICOM image can be transmitted to the system for verification. The image is then passed through the automatic image detection algorithm, which first slices the DICOM image into "tiles" which are then passed to the first layer of the neural network, the output would be passed to the second layer and repeated for each layer until the image recognition is complete. The output of the system is an interpretation of what the DICOM image was of, for example "Left knee, human, total knee implant, and bone cement." If the output of the image recognition matches the billing code the claim would be processed automatically. If the confidence level was for the submitted billing codes was below a predetermined threshold, the claim would be flagged for further inspection. If during manual inspection it is determined the submitted codes match the image, the claim would be processed and the image could be used for additional training for the neurons. If the image did not match the billing codes the after manual inspection the claim could be denied.

In some embodiments, both a pre-op and a post-op image are required. In addition to image recognition, a reverse image search of the database can be performed to ensure that the image submitted with the claim is not being reused. Intra-operative pictures could be required for some procedures instead of or in addition to X-rays.

In some embodiments, the AI techniques described herein are used for navigation. For example, motorized wheelchairs could be converted from normal operation to autonomous or semi-autonomous operation. This could be very useful for people who have limited use of their hands of arms to navigate the wheelchair, for instance. In one embodiment, a semi-autonomous wheelchair is equipped with sensors to look for potential hazards or obstacles in the direction of travel. If there was a small obstacle in the path that could be avoided, the chair could automatically drive around the object, then return to the original path. If the object could not be avoided, the wheelchair could be programmed to stop before hitting the object. A fully autonomous wheelchair would also reroute its path to avoid obstacles. In another embodiment, it may be desirable to have a remote transponder that is used to determine the direction in travel. In this embodiment a small transponder is attached to the belt or a person and the wheelchair would automatically determine a path that would follow the transponder at a predetermined distance while avoiding any obstacles. The chair could also avoid by stopping, or going around changes in the height such as stairs, curbs, or potholes. This could be done when fully autonomous or semi-autonomous. The chair could also automate portions of navigation, such as positioning the wheelchair on a chair lift.

In addition to traditional sensors, autonomous drones could be used to provide an additional input. For example, this could be useful in crowded areas to help determine the best path for traveling to a certain point. The drone can include traditional cameras and thermal cameras. The drone can communicate with the chair via Wi-Fi or other short- to medium-range radio wave protocol. In some embodiments it might be desirable to have more than one collaborative drone. It is also considered that a single drone could provide camera feed, or mapping information to more than one chair.

In one embodiment, a universal protocol could be written and used with collaborative drones such that when a drone is available in an area, any equipped chair would automatically connect and use drone information as an additional input. Although described herein in terms of a wheelchair, one of ordinary skill in the art will understand that these aspects may be embodied in bicycles, tricycles, hoverboards, Segways, boats, jet skis, any type of jet drive vehicle that can be controlled, and the like. For instance, these techniques can be linked to GPS, sonar, camera systems, light air, robotic self-taught autonomous robotic systems, and the like.

In addition, the techniques could also be embodied in an autonomous robotic system such as a nurse, which could perform a nurse's physical responsibility (e.g., taking vitals, drawing blood, etc.) and/or offer nursing technical support (e.g., explaining procedure, addressing questions, obtaining consent, etc.) to the patient directly or in a virtual manner. The autonomous robotic nursing system integrated with the AI system 104 can determine the physical and mental health of the patient. The AI system 104 can analyze the patient information (e.g., test results, systematic questioning, etc.) obtained from the patient and/or robotic nursing system. Once enough information is available to target a diagnosis the AI system 104 can send the patient information to the physician for review and/or generate a diagnosis or list of possible diagnoses for the physician's review. If the diagnosis generated by the AI system results in a medical procedure (e.g., a procedure to treat the diagnosis), the AI system 104 may direct the autonomous robotic nursing system to prepare the patient by explaining the procedure, additional options and the reason to provide the procedure. The AI system 104 may also be equipped to detect the patient's understanding of the procedure by using patient monitoring (e.g., eye movement, rate of breathing, shaking, etc.) via the robotic nursing system. In the occurrence that AI system 104 detects the patient is unsure of the procedure or still lacks complete understanding the autonomous robotic nursing system would provide additional information and reassurance, at the direction of the AI system.

Moreover, the concepts disclosed herein can be embodied in a self-driving or self-directed exoskeleton. A person who may have a disability weakness or wants to amply force (e.g., soldier, etc.) the exoskeleton would amplify the strength or force of an individual through servomotors, robotic controls, hydraulic pistons, and the like. It could be rigidly attached to the person's frame (e.g., through pins into the bone, etc.) or it could be externally attached with form fitting cuffs, inflatable bladder type cuffs or supports, or structural supports. It can be built to the trunk, specific arm, leg, foot, toe, and the like. It could also be used for patients with cerebral palsy, neuromuscular weakness, strokes, CVA, and the like. This could be used for rehabilitation but also used to drive a motor, move or direct patients to certain locations to result in essentially a self-driving exoskeleton for those patients who have disabilities or those patients who want to amplify their forces in specific areas. This would not only increase the force or improve range of motion, function, strength, work against some of the spasticity or rehabilitation recovery for range of motion. It could also be used if these are used for external to take exoskeleton to its specific location or to drive them to direct them to do a specific activity at a specific location including lifting, moving, or exoskeleton plus self-driving autonomous vehicle controlling fine motor, specific motor, or gross motor. It could be single motor, such as servomotor. It could be a fine wheel electromagnetic motor, hydraulic piston, or a combination thereof. It would also have superficial sensors that would allow tactile feedback in at the periphery or at the central joint which is mechanically, electrically, or electromagnetically for example drive. Furthermore, these embodiments can be recharged. For example, they can be recharged via photoelectric systems, sunlight, heat, fluid motion, electromagnetics, and the like. In an embodiment, they are recharged remotely.

In yet another aspect, the artificial intelligence and/or virtual reality techniques are used for self-driving diagnostics. The general concept is that patients might have individual testing. They may have x-ray, ultrasound, MRI, PET scan, bloodwork, and/or echocardiogram, for example. However, these are all individual treatments done on individual machines at individual locations. This would also add electronic diagnostics such as EKG, EEG, sleep labs, and the like.

When the patient comes in and has some concerns about pain, the systems and methods can be used to initially do a scan of ultrasound, EKG, or EEG to examine if there is an abnormality identified. The system would then direction the patient to the next step by using automation, artificial intelligence, and/or a possible link to a radiologist, physician, nurse, or healthcare provider who can automatically approve the next appropriate test. For example, if a patient has pain, the system would direct the patient to undergo a quick scan with an ultrasound. The system analyzes the data from the ultrasound to detect if there is any irregularity, such as an irregularity on a bone. The system would then direction the patient to immediately have x-ray or CT to determine if there is a fracture in the bone. If the system detects that there is a questionable fracture, the system then automatically identifies the fracture type and/or location and automatically generate a treatment program to be recommended or instituted either directly to a patient or a physician. Other irregularities that may be detected by the system from the ultrasound include if there is a mass or tumor or if there is a question of irregularity of other types of tissues. Accordingly, the system would then direct the patient to go the appropriate medical device based on the irregularity detected, such as a MRI. All of these diagnostics could be in one room or one location or potentially within one device.

Next, if there is a question and one notices increased body temperature or sweating or increased in fluid osmolarity, a urine analysis could be performed. The system could automatically draw blood either through robotic system or have a blood technician draw it, sequentially these tests are automated and driven by this automated self-driving diagnostic system. If the blood is then drawn and there is a question about diabetes as blood sugar might be elevated, one would scan the stomach to see if the patient ate recently if this is a false-positive or false-negative and then it would go to the next system on this. If there is question, they would do an ultrasound to scan whether the patient might have other associated issues such as increased risks for cardiac problems as diabetics have a small vessel disease or retinal disease. Retinal scan would go on looking at all of the diabetic potential issues down the algorithm. One would then look at associated diseases with diabetes. One might check pancreas function or liver function. These would go down the diagnostic list and these would all be performed before the physician would actually see the patients so this would be automated diagnostics. This could also be done through a bed or other surface so patient could lay down, especially if they are in the hospital. If they sweat excessively or move excessively, one might have sensors in the surface, EEG and EKG in the surface. If the patient moves excessively during nighttime, while they are active, if they sweat, or if they have sensors that show body chemistry changes, automated bloodwork would either be ordered or could be done at the bedside. EEG, EKG, or ultrasounds could also be automated either they are in a single unit or multiple units, but they would be potentially driven straight to the patient or a series of tests would be automatically ordered so the physician does not have to actively get involved, but these would automatically line up so that the physician would have all the tests in and already in place before they actually talk to and examine the patient. This automated system could include a single or series of tests. It could be linked from urinalysis and bloodwork to MIll, CT, EKG, EEG, gait analysis, video monitoring so one could see specific motion patterns.

Once the diagnosis is delivered, a treatment protocol can be given, followed by a follow-up protocol. This could be done through video, holograms, activity patterns, robotic simulation. In addition, the follow up protocol could also be done through sequential follow-up bloodwork and follow-up testing. It is coordinated and organized at appropriate interval so the patient has expedited throughput. In one embodiment, there could be automated testing at home so that per patient's mobile devices and artificial intelligence the right diagnostics could be at someone's doorstep or someone's home either permanently or temporarily, the appropriate sensors either implantable or monitored on the surface, the appropriate diagnostics such as home ultrasound diagnostics or diagnostically come to localized facility. These would all be setup in advance and multiple tests would be done including ultrasound, bloodwork, and urinalysis. All reasonable and appropriate tests would be done all at either the patient's home or specific location. It would all be automated through this mobile and/or autonomous diagnostic, autonomous therapy/treatment. Again, this would be for example if someone is recovering from knee replacements automated x-rays would be setup. These could be done at home or through a mobile device or with automated ultrasound, bloodwork, therapy patterns, motion patterns, accelerometer on phone so visual aspects from the phone goniometer, apps, or through rented or permanent diagnostics which could be delivered, mailed, or shipped back. These could all be linked into specific patterns. The sensors would be linked to each other so the appropriate diagnostics could be done and then they would be returned. These would be mobile or wirelessly delivered to a central computer through AI. It could constantly monitor, upgrade, and also look at behavioral modifications and behavioral treatment patterns that are known through AR to change peoples' behavioral patterns such as if one is a diabetic, which foods they should ignore, which activities they should do or which time these activities should be performed. When is the best time to study, when is the best time to sleep, when is the best time to perform work related activities. This could automate not just with therapy but actual day-to-day lifting and give you best advice, best case examples, and possibly through noxious stimulants or positive reinforcements to teach you what the right activities would be. If you are a diabetic and you are eating sugars, it might give you a noxious not to do this or suggest alternative diet treatment. Finally, these could be autonomously linked to food delivery service or activity delivered to your home so you have the appropriate nutrition, appropriate activity, or appropriate advisors. There is an entire system and pattern for autonomous diagnostics, therapy, and/or follow-up treatment with positive reinforcements and/or negative reinforcements. This will be acquired into one solid system.

Another embodiment could use machine vision and deep learning to create an autonomous diagnostic unit. A system could contain multiple diagnosis modalities (ultrasound, MIll, X-Ray, CT, PET, etc.) which monitors the output of the imaging modality using artificial intelligence to look for indicators of specific conditions or disease states, if one of these conditions are identified during the procedure an alert could be sent to the operator and a physician if additional imaging is required. If the physician had previously approved the scans, or responds via a computing device, phone, messaging system while the patient is still in the scanning system additional diagnostic modes could be performed at the same time. This would prevent the patient from being transported to a different area and requiring a second visit. In addition to imaging, other diagnostic tools could be automated as well including blood draws. Some embodiments would use robotics to perform blood draws, or they could be done with by a phlebotomist. The phlebotomist and physician could receive an alert while the initial scan was occurring.

In addition to monitoring the output of diagnostic imaging system, the patient's vitals and other sensors could be monitored. This could include but not be limited to blood pressure, skin conductivity, heart rate, EKG, blood oxygen level, temperature, and results from previous lab work. These could be monitored during procedures or any time the patient is being monitored. If the system recognizes a condition which could require additional blood work, an alert could be sent out to suggest additional tests. In scenarios where a physician or insurance carrier is required to authorize the system could trigger a notification to the required party, then order the required test. For example, when a patient has an unexpected fever the system could notify the phlebotomist and the lab to perform a count of leukocytes.

In yet another aspect, the artificial intelligence techniques described herein are used to remind a user to perform an activity such as when to take or apply a medication. For example, in one embodiment the AI techniques remind a parent and/or optimize when to give a medication to a baby. The AI techniques disclosed herein can incorporate a baby monitor (sensor and/or visual) and relay the information to a mobile computing device such as an application on a cell phone. The parent can use the mobile computing device to input the medication prescription into the application such as by scanning the prescription with the mobile device. Such information inputted can include the medication type, dosage, and how often the medication should be administered. The application then monitors the child's sleep patterns (via the baby monitor) and determines the best time to administer the medication. For example, if the child is sleeping, the application would not active the reminder until the child wakes up during the night—instead of waking the child up while the child is sleeping. In particular, if the medication is supposed to be administered every 4 to 6 hours, the application would wait to send a reminder to the parent to administer the medication until the child is awake during the interval when the medication is to be administered—in this case between hours 4 and 6. If the child says asleep during the entire interval, the application waits to send the reminder until the time limit is reached—in this case at 6 hours.

In another embodiment the AI techniques remind a patient and/or optimize when to take a medication. Biosensors that record biometric data from the patient are incorporated into the techniques described herein and rely that data to the application on the mobile computing device. The application can then reminds and/or warns a person to take or not to take the medication based on the information from the biosensors. For example, if a person is trying to maximize weight loss and taking a medication to increase metabolism, the application can indicate when the person should take the medication for maximum effect. The person can input the medication information into the application and then the application would use an algorithm, the information from the biosensors and the recommended dosage to indicate the best time of the day to take the medication. In this case, the application may also indicate to the person when they should or shouldn't consume certain foods based on the information from the biosensors and the medication information in the application. In one example, the medication may include caffeine, which affects hear rate. Some people are more sensitive to caffeine than others and medications that include caffeine can cause a sensitive person to feel light headed and dizzy. Alternatively, some people are less sensitive to caffeine and may feel zero effect from the medication. Either instance can cause the person to be less consistent in taking the weight loss medication or quit all together. The application, via the biosensors (such as a hear rate sensor) can monitor the heart rate of the person immediately after taking the medication to determine sensitivity. Based on initial baseline levels, continued monitoring of the biometric data and/or the medications recommended dosage, the application can indicate how often the medication should be taken and when to increase the dosage.

In yet another aspect, the artificial intelligence techniques described herein (e.g., AI system 104) can be incorporated or in communication with the control system of a surgical robot, such as the da Vinci surgical robotic system by Intuitive Surgical. In this embodiment, the AI system 104 can collect the data, such as surgical information or patterns, from surgical robot and/or surgeon during medical procedures. The AI system could gather and analyze this data on a personal level (surgeon), a local level (surgical group or hospital), and/or a national or international level (medical procedure or type of surgical robot). The AI system 104 can use this data as an input to create a model to train new users how to operate the surgical robot. Moreover, this data can be combined with patient records and outcomes to generate the best techniques/procedures regarding the surgical robot for optimal patient outcomes and train surgeons accordingly. Similarly, the AI system 104 can use the data collected to generate surgical guidance where the surgeon would receive feedback, using the surgical robot's display, virtual reality and/or augmented reality, on the best procedure or steps forward based on the model and/or the steps already taken by the surgeon. In another embodiment, the AI system 104 may instruct the surgical robot to carry out the preferred procedure, autonomously, based on the surgical guidance model using machine vision.

For example, the AI system 104 can be used with a surgical robot to remove and/or facilitate the removal of tumor cells. Through repetitive use, the AI system 104 can learn which cells are tumor cells and which cells are normal cells, allowing the AI system to operate the surgical robot to remove the tumor cells while leaving the healthy cells in position, for example by neovascularization. For example, areas with hyupervascular supply often are related to fast growing tumors. The AI system 104 can learn and/or identify which areas are more vascular and direct the surgical robot to remove the areas that are more hypervascular and leave the areas that are less vascular or have normal vascular flow through normal vascular anatomy. Similarly, this concept can also apply to normal scaffold anatomy or normal cellular anatomy. By connecting the surgical robot to the AI system 104, the AI system can progressively learn, as described herein, surgical robotic functions and/or cellular functions to treat a specific area while looking for abnormalities or irregularities in function. This can be done on a general to a more granular basis. Moreover, the AI system's 104 learning process could be altered based on any sudden changes. For example, if one removes one data point from the AI system 104, it would alter the entire stream. The data point could be removed at the end of the learning process or the beginning of the learning process. This could be revisited potentially for the next patient or next subgroup of patients. It is understood that the AI system can be used with any surgical robot and/or surgical robot operation/technique. For example, the Ai system 104 can be used with the systems and methods describe in U.S. Pat. No. 9,155,544 and U.S. Patent Application No. 2017/0112577, the entire disclosures of which are hereby incorporated by reference. The Ai system 104 can also be used with other surgical techniques and devices such as those disclosed in more detail in U.S. Pat. No. 7,104,996 and U.S. Patent Application No. 2016/0144113, the entire disclosures of which are hereby incorporated by reference.

In yet another aspect, the artificial intelligence techniques described herein (e.g., AI system 104) can be incorporated or in communication with a graft such as grafted blood vessel in an eye, although other grafts are within the scope of the present disclosure. The graft may be created from a combination of a shape memory polymers and a biologic. The shape memory polymer could be constructed from a electroactive polymers (EAP) which contracts and dilates with a change in electrical current. The AI system 104 would monitor the neural impulses of the sympathetic nervous system via other patient monitors 102. These neurons connect with the muscle cells in the blood vessels. When these neurons secrete norepinephrine it causes the muscles to contract. By monitoring these impulses, the AI system 104 can correlate these impulses to other stimuli such as stress, physical activity such as running, or other biological responses. The AI system 104 could also respond directly to the neural impulses. The AI system 104 would then activate the EAP in the graft to closely mimic the original vessels—dilating or contracting the blood vessel. Another embodiment could use diagnostic scans (ultrasound, MRI, etc.) from multiple patients to create an AI model for the vessel behavior. The Ai model could be preloaded and into the controller for the graft. This output of this model could also be used to 3D print a graft with varying density and patterns of the EAP such that the behavior of the vessel behavior. These grafts could be create from thermally activated polymers or alloys, electrically activated alloys, or a combination of both. The graft could also be created without the biologic so that it is totally synthetic or could totally biologic. This would not be limited to blood vessels but could be used in any lumen including but not limited to pancreatic duct, the gastrointestinal tract, the bronchi, renal tubules, colon, etc. These contractible lumens could also be in non-biologic applications such as, but not limited to, fluid flow, oil flow, gas flow, robotics, and industrial equipment. The information gathered from the AI model could also be used in conjunction with diagnostic imagine to create a filter that could compensate for the movement of the blood vessels during observation by predicting the movement. This could be used in endoscopy, ultrasound, MRI, and other diagnostic imaging techniques known in the art.

In one embodiment, the data shared with the AI system 104 can be mined on an individual or group basis for specific information. Moreover, in one embodiment, the AI system 104 may ask the patient to share data and/or ask specific questions to the patient. An incentive may be given if the patient responds. Moreover, an incentive can be given other professional for information. For example, data including but not limited to robotic surgical techniques, sleep patterns, etc. could be exchanged for data access to the input data, the output data, or could be a monetary benefit such as company stock or coupons. The more data that is provided the more stock or coupons the user could earn. The stock could be kept and the value would grow as the value of the data grows, or they could be traded in for cash but lose out in growth. Recruiting more data miners, or recruiting more users could allow for a bonus.

For example, the AI system 104 could incentivize users (e.g., patients, physicians, professionals) in order to gather information on medical costs. Users could fill out questionnaires and those that answer or provide most data on a topic get bonuses or prizes or more stock. The questioners could be paper, electronic, or in a game format with prizes or TV show type excitement like Wheel of Fortune or Jeopardy. The data miners go out and ask others and submit data (would need to cross check accuracy) but would determine what true medical costs are and collate and share. To add revenue obviously advertising but with a twist as backed up by data ie who has best price on MRI. They then would want to advertise as the firm would have data to back up. Also, the AI system 104 may incorporate a payment system, like Apple Pay, but where people are rewarded for their data sharing and mining. Confidentiality must be set up with encryption which protects and constantly changes but pays people for real data rather that do it in the sly and provide a nominal value. Daily or hourly questions or problems sent out and those that provide are gaining value and can choose their return. This would make the data mining more transparent instead of hiding the fact it is happening. The AI system 104 would allow the information from Bluetooth enabled biometric data from wearables to be submitted to a third party, such as hospitals, surgery centers, insurance carriers, etc for various purposes, such as evaluation. The users could be compensated for this information. Also data from smart homes, sensors, or security cameras could be collected. Individuals could approve and share some or all of the data. The AI system may identify and/or omit confidential data and/or encrypt the data so that it is not shared for mining.

In another embodiment, the AI system 104 may be communication with phone or other wearable device that is configured to actively transmit all data or selectively transmit the data to the AI system. The user may control the transmission of data thru voice activated or an on/off system. The AI system 104 may also "scramble" or encrypt the collected data to keep the data anonymous but accessible for use in data pools. This could have advantage that unlike Facebook or Amazon where the third party knows where data comes from one could actively submit anonymous data which is still valuable especially for medicine applications or design applications. In another embodiment, the phone or other wearable device "scrambles" or encrypts the data before sending the data to the AI system 104 to create anonymity while still allowing the data to be mined.

Various patient monitors (e.g., patient monitors 102), and uses thereof, for use with the AI system 104 and the AI techniques described herein will now be described. Generally speaking, the following patient monitors and methods of use thereof are for collecting biometric data to determine a condition of a patient. Such a condition can include, but is not limited to, health information, emotional reactions, physiological reactions, pain, etc. Further, the patient monitors and methods of use described below are generally described as standalone systems. However, it is understood the patient monitors and methods of use described below can be used with the AI system 104 described above. It is also understood, that the AI system 104 can be in communication with the standalone patient monitors described below and/or take the place of some of the components of the standalone patient monitors.

One example of biometric data that a patient monitor sensor 102 can detect is blood pressure. Typically, blood pressure is measured using a sphygmomanometer. Biometrics, such as blood pressure, can provide information about a patient's response to stimuli such as physical activity and consumption of various media. In addition, various kinds of injuries and ailments can be associated with changes in blood pressure and blood vessels, which if detected, can be used to diagnose a patient and/or evaluate the effects of treatment. Retinal imaging and evaluation can be used to determine a patient's blood pressure and, through various methods, can allow physicians to diagnose diseases and health problems including diabetes, hypertension, and concussions. For example, ophthalmologists look into patients' retinas for diseases and other problems such as diabetes, easy bleeding, and edema on the brain. Generally, a patient's pupil is dilated during the imaging. Retinal scanning is one way to image a retina in which a small infrared light traces a path across the retina when the pupil is dilated. The difference in reflectivity of the blood vessels and the surrounding tissue allows for mapping of the retina by sensing the levels of reflected infrared light at different points.

Referring to FIG. 24, a retinal evaluation system (e.g., patient monitor) for medical diagnosis is generally indicated at 1410. The retinal evaluation system 1410 includes an imaging system 1412 configured to capture highly magnified images of a subject's retina. The imaging system 1412 is configured to transmit the images to a memory 1414 for temporary or permanent storage on the memory. An image processor 1416 is operatively connected to the memory 1414 to access the image data stored on the memory. The image processor 1416 is configured (e.g., by executing processor-executable instructions stored on memory 14, etc.) to process the image data and generate one or more outputs based on the image data. For example, in one or more embodiments, the image processor 1416 is configured to generate an enhanced rendering ER of the image for being displayed on a display 1418. As explained below, the illustrated image processor 1416 is also configured to evaluate the image data to perform a medical diagnostic of the subject. The processor 1416 can, for example, display a diagnostic output DO on the display 1418. As explained further below, in certain embodiments, the image processor 1416 is also configured (e.g., by executing processor-executable instructions stored on memory 1414, etc.) to evaluate the image data to evaluate a subject's physiological response to a stimulus, for example, to evaluate the qualitative effect of media, to provide an input used to generate active feedback in a user experience (e.g., a virtual reality simulation), or to perform other types of medical evaluations.

In the illustrated embodiment, the memory 1414, the image processor 1416, and the display 1418 are all components of a laptop computer 1419 (broadly, an image evaluation device) that is connected to the imaging system 1412 by a wireless connection (e.g., Wi-Fi, Bluetooth, etc.). It is understood that other computing resources may be used in other embodiments. For example, it is contemplated that a mobile device (e.g., a smartphone or tablet computer) may be used instead of the laptop. In addition, images can be stored on more than one memory and/or processed by more than one processor in certain embodiments. It is understood that the image evaluation device (e.g., memory 1414, image processor 1416, and the display 1418) may be in communication with the AI system 104 if the retinal evaluation system 1410 is connected to the AI system or the AI system may take the place and perform the function of the image evaluation device (or one or more of the components thereof).

In the illustrated embodiment, the imaging system 1412 includes a support frame 1420 configured to be supported on the head of the subject. An image capture device 1422 is mounted on the support frame 1420 to be operatively aligned with one of the subject's retinas when the support frame is supported on the head of the subject. In the illustrated embodiment, the support frame 1420 is generally configured as an eyeglasses frame. The illustrated frame 1420 includes eyepieces 1424 joined by a bridge 1426 that supports the frame on the subject's nose, along with temples 1428 that extend rearward from the eyepieces to support the frame on the subject's ears. Although the illustrated embodiment uses an eyeglasses frame 1420 to support the image capture device 1422 in operative alignment with the retina of the subject, other embodiments use other support structures to support an image capture device in alignment with the retina. For example, other types of headwear, such as goggles, a headset, a helmet, etc., may be used in certain embodiments. In other embodiments, the image capture device 1422 may be mounted on a stand supported on a floor, a table, etc.

Unlike those of conventional eyeglasses, the illustrated eyepieces 1424 are configured to promote dilation of the pupils blocking at least some ambient light from entering the eye through the cornea. Thus, in the illustrated embodiment, the eyepieces 1424 are substantially opaque light blocking elements positioned in front of the eyes of the subject to block light from entering the eyes. By blocking light from eyes, the eyepieces 1424 cause the pupils to dilate. The dilated pupils provide an improved view of the retinas and thereby enhance the conditions for capturing images of the retinas using the imaging capture device 1422. It will be understood that light blocking elements can have other configurations in other embodiments. For example, in some embodiments, the imaging system can include an optical gasket that extends around the eyes and is pressed against the face of the subject to provide an optical seal about the eyes that substantially inhibits even peripheral light from entering the eyes. Alternatively, instead of dilating the pupils, in one embodiment, the imaging system 1412 may include contact lenses that are specifically designed to allow for imaging through a small pupil opening without dilation of the pupil. The contact lens includes prism and magnification elements to allow for imaging of the backside of the eye without the full dilation of the pupil. The prism element could be temporarily engaged using electromagnetic of RF technology during the imaging. In this embodiment, once the imagining is complete, the contact lens can adjust to allow for normal vision. In another embodiment, contact lenses could be used to shield the eye from visible light to cause or facilitate the dilation of the pupils. In one embodiment, if the eye contains a grafted blood vessel, as described above, the imaging system 1412 and/or AI system 104 can control the dilation and contraction of the grafted blood vessel.

In the illustrated embodiment, the image capture device 1422 comprises a light source 1430 which is configured to shine onto the eye, at which point an image sensor 1432 captures an image of the retina R. Some embodiments include a digital camera as an image sensor 1432, but it will be understood that other types of image capture devices (e.g., including more specialized light sensors, etc.) can be used in other embodiments. The image sensor 1432 is mounted on an eyepiece 1424 to capture an image of the retina R as the light is transmitted to and reflects from the retina R. Detecting the quantity of light reflected from different points on the retina R is sufficient to map the retina. For example, a point on a blood vessel will reflect less light than other points on the retina. In certain embodiments, the image sensor 1432 is also configured to capture images of other portions of the eye, for example the iris. The image sensor 1432 stores the captured images to the memory 1414 where it is accessed by the image processor 1416 for retinal evaluation as described in greater detail below.

In a preferred embodiment, the image sensor 1432 is a digital infrared camera and the light source 1430 is an infrared light within the spectrum detected by the digital infrared camera. Because the human is eye is not sensitive to infrared light, the light source 1430 can provide infrared light for the image sensor 1432 without constricting the pupil. In another embodiment, the light source 1430 creates visible light and the light level is controlled so that the pupil stays dilated but there is sufficient light for the image sensor 1432 to capture an image of the retina. In still another embodiment, the image sensor 1432 and the light source 1430 operate in the visible spectrum and the image sensor 1432 captures an image while the light source 1430 provides light but before the pupil constricts significantly. In other embodiments, the light source 1430 could be a source of near infrared light, ultraviolet light, or multispectral light, with a corresponding appropriate image sensor 1432. In one embodiment, the lights source 1430 and image sensor 1432 may be part of the LiDAR system.

In one or more embodiments the imaging system 1412 comprises a controller 1434 that is configured to automatically control the image capture device 1422 for capturing images of the subject's retina. In FIG. 25, arrows connecting blocks in the diagram shown in phantom illustrate control connections between the respective components and arrows shown in solid line show the light from the light source 1430. In the illustrated embodiment, the controller 1434 is a dedicated component of the imaging system 1412; in other embodiments, the controller 1434 runs on a processor 1416 of the computer 1419 or another device. In some embodiments, the controller 1434 is able to modify the focal point, energy, wavelength, activation frequency, and intensity of the light or any subset of those attributes by communicating with the light source 1430. The controller 1434 is operatively connected to the light source 1430, and in one embodiment can control the focal point, wavelength, energy, intensity, activation frequency, etc., of the light from the light source 1430. This permits the imaging system 1412 to be able to look at different parts of the eye. To capture an image, the controller 1434 communicates to the light source 1430 to illuminate the eye E. The eye E reflects some of the light, and the image sensor 1432 detects the light and generates and sends an image to the controller 1434. The controller 1434 then sends the images to the memory 1414.

In some embodiments, the controller 1434 is operatively connected to an eye position sensor 1436. Preferably, the eye position sensor 1436 gathers images of the eye continuously and relays the images through the controller 1434 to the processor 1416, which is configured (e.g., by executing processor-executable instructions stored on memory 1414, etc.) to determine the position of the eye and which direction the eye is facing. The eye position sensor 1436 relays the position of the eye E back to the controller 1434. In some embodiments, the controller 1434 uses this position to evaluate how to control the direction of the light from the light source. Alternatively, multiple light sources can be used, the controller at any time selecting the light source or sources that will properly illuminate the eye. In at least one embodiment, the controller can use the position data to physically move the image sensor 1432. In a preferred embodiment, the position data is not gathered from a separate sensor, but the image processor 1416 or the controller 1434 determines the position based on the images from the image sensor 1432. In an alternate embodiment, multiple light sources 1430 and multiple image sensors 1432 eliminate the need for an eye position sensor 1436.

In some embodiments, an auxiliary device 1438 also sends data to the controller, which is sent back to the computer 1419 to be stored in the memory 1414. The auxiliary device 1438 can be a device for collecting any data that a processor can be configured to use in conjunction with images of the eye to make medical diagnoses. In some embodiments, more than one auxiliary device 1438 is used. Examples of auxiliary devices are Fitbit and similar devices, blood sugar measurement devices such as those used by many people with diabetes, a device to estimate sweating or hydration, and other devices to monitor blood pressure, pulse and/or irregularities in the heartbeat such as the wrist-wearable blood pressure monitor or earpiece monitor, both presented below. Another exemplary auxiliary device 1438 includes an ultrasound system for an eye and orbit ultrasound or laser imaging system for a similar evaluation is used to measure blood vessel dilatation and blood flow rate; detect foreign substances, retinal detachment, and tumors; and help diagnose and monitor glaucoma, cataracts, and lens implants, among other uses. Other examples of auxiliary devices include thermal probes; vibratory sensors; sensors to detect electro-chemical makeup, temperature, electrical current, or color of the skin; devices to detect blood, microvascular blood, urine, or other fluid composition; sensors to detect sweating and sweat quantity, its composition, or both; devices to measure electrophysiological data; an ultrasound to estimate hydration or measure other medical data; a device to measure intraocular pressure; and a thermometer. Measurements can generally be done in real time or at one or more discrete times. Other auxiliary devices are possible without departing from the scope of the disclosure.

Figure 25A:
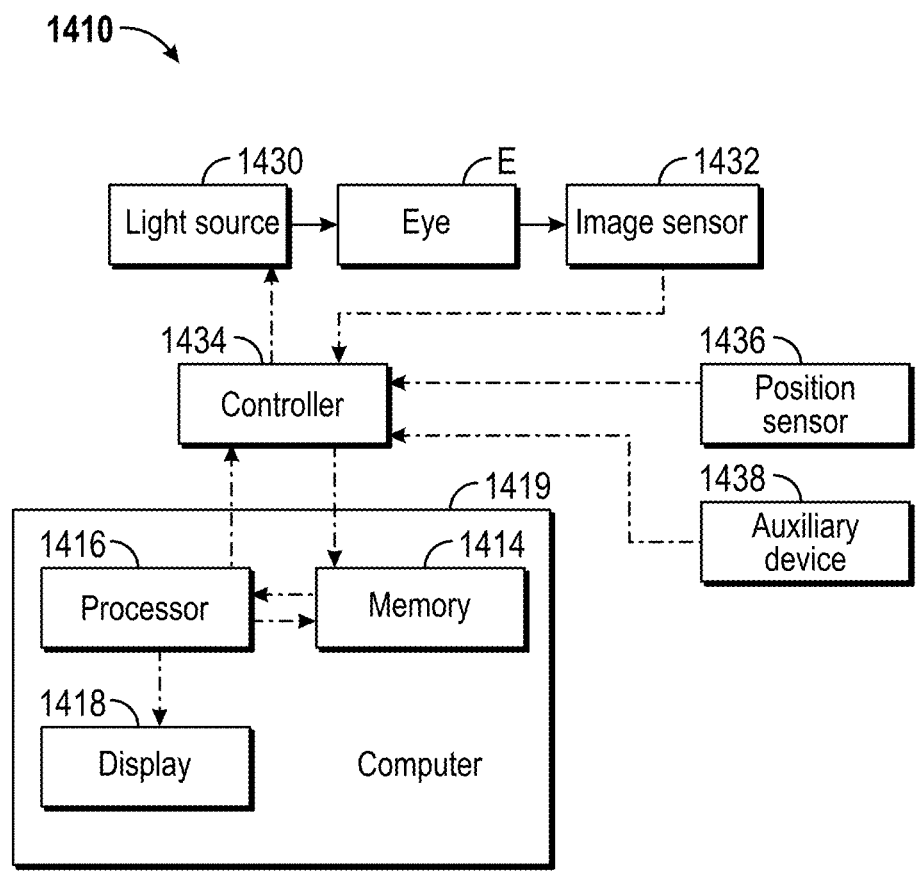
FIG. 25A is a schematic block diagram of an exemplary embodiment of the retinal evaluation system of FIG. 24.
Figure 25B:
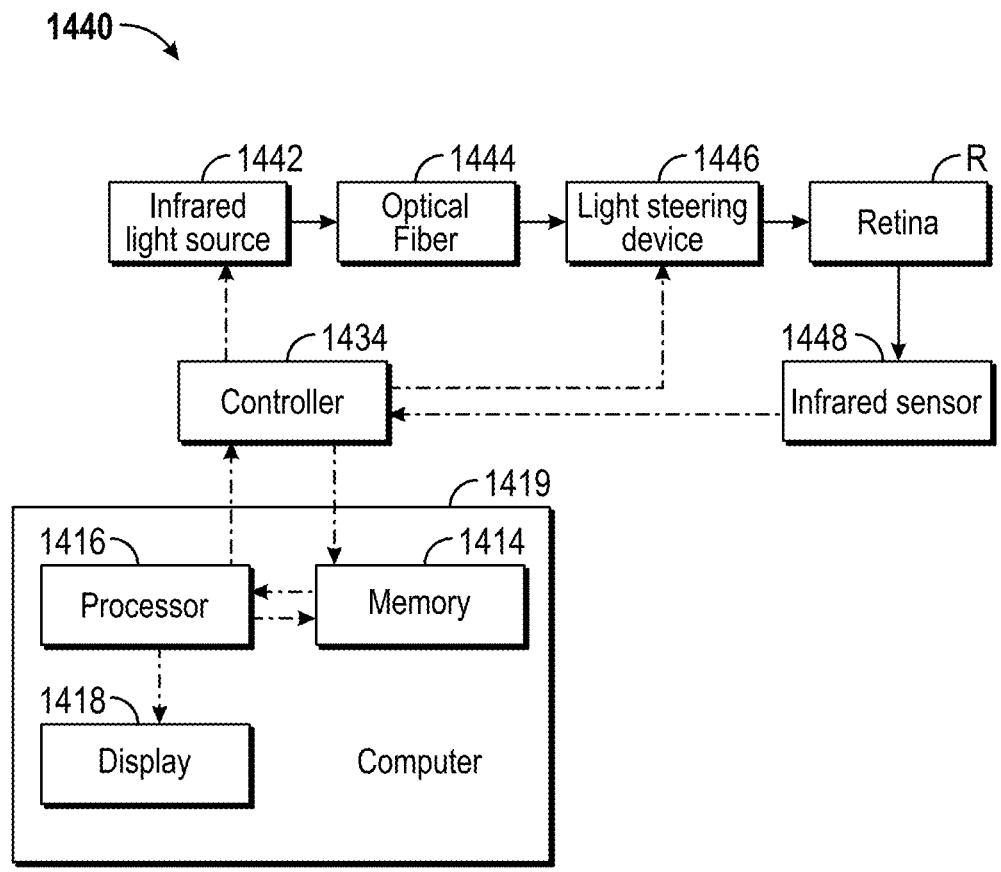
FIG. 25B is a schematic block diagram of a retinal scanning system included in an alternative exemplary embodiment of the retinal evaluation system of FIG. 24.

Referring to FIG. 25A, in some embodiments a retinal scanner 1440 is used for imaging instead of the imaging system 1412. The laptop computer 1419 is also shown in FIG. 25A for convenience and clarity. The retinal scanner 1440 utilizes the same controller 1434 as the imaging system 1412. It includes an infrared light source 1442 that sends a low energy, narrow beam of light through an optical fiber 1444 to a light steering device 1446. In an alternative embodiment, the infrared light source 1442 and the light steering device 1446 are adjacent or precisely aligned such that no optical fiber is needed between them. The controller 1434 controls the light steering device 1446 so that the light scans in a predetermined path over the retina R. An infrared sensor 1448 detects the light reflected by the retina R. The infrared sensor 1448 is preferably configured to sense a narrow range of wavelengths and determine the intensity of the reflected infrared light at each of many small time intervals. Preferably, these time intervals are coordinated with changes in where the light hits the retina R. This information is sent back to the controller 1434 and stored in the memory 1414. The processor 1416 determines for each time interval whether the light hit a blood vessel (e.g., when most of the light was absorbed) or another part of the retina (e.g., when most of the light was reflected). The processor 1416 then correlates the data and generates a retinal image. Stored information about the path will tell what location the light hit at each time interval and, as previously stated, at this point the processor 1416 has already evaluated whether the light hit a blood vessel or not for each time interval, therefore, every point hit by the light can be mapped as a blood vessel point or a nonblood vessel point. In other embodiments, the processor 1416 is configured (e.g., by executing processor-executable instructions stored on memory 1414, etc.) to recognize when the light hit the border of a blood vessel as well, among other variations that can be made without departing form the scope of the disclosure. In some embodiments, the controller 1434 is able to modify the focal point, energy, wavelength, activation frequency, and intensity of the light or any subset of those attributes by communicating with the light steering system 1556, the light source 1530, or both.

Referring again to FIG. 24, in one or more embodiments, the image processor is configured (e.g., by executing processor-executable instructions stored on memory 1414, etc.) to use the images of the eye that are stored on the memory 1414 to perform a medical evaluation. The image processor 1416 is configured to retrieve the captured images stored on the memory 1414 and to generate a map of the subject's retina (and, in some embodiments, other portions of the eye) based on the captured images. In certain embodiments, the memory 1414 stores one or more baseline retina maps, such as maps of a healthy retina, maps of the subject's retina at an earlier point in time, maps illustrative of how certain diseases manifest in the retina, etc., which are used by the image processor 1416 for comparative evaluation. For example, the image processor 1416 can compare the retinal map based on the captured image to the baseline to identify irregularities or changes in the retina. Suitably, when the image processor 16 detects a problem with the retina, it displays an indicative diagnostic output DO on the display 1418 or provides another type of indication to the subject or the subject's medical provider. In the illustrated embodiment, the image processor 1416 also displays an enhanced rendering ER of the image on the display 1418 so that the doctor or other medical provider can verify the diagnostic output DO based on the image. In some embodiments a baseline is displayed, such as a previous map of the subject's retina.

In some embodiments, the image processor is configured (e.g., by executing processor-executable instructions stored on memory 1414, etc.) to monitor blood pressure. When an image is stored in the memory, a processor can determine the radius of one identifiable point on a blood vessel of the eye. Preferably, an image from a diastolic event and an image from a systolic event from about the same time are used to determine a diastolic and a systolic pressure. In one embodiment, the processor 1416 refers to calibration data and interpolates between calibration data points, extrapolates beyond calibration points, or uses a trend line or curve based on calibration points. In some embodiments, multiple identifiable points on blood vessels are used together to determine blood pressure. For example, the blood pressure is calculated using each point and the processor 1416 records the average of the results from the different identifiable points. Other methods of using a retinal image or image of the eye to take blood pressure are possible without departing from the scope of the disclosure. For example, blood pressure may be calculated using a blood vessel radius and the elasticity of the blood vessel.

To calibrate in a preferred embodiment, multiple images, at least an image during a systolic event and an image during a diastolic event, are input into the memory 1414 with corresponding blood pressures. The blood pressures are measured in another way at the times the images are taken. If multiple identifiable points are selected measure, then this process is repeated for each point and they are calibrated separately. For the selected identifiable point on a blood vessel of the retina, an ordered pair consisting of a radius and the corresponding blood pressure is saved in the memory 1414 for each image. The ordered pairs are then compiled into a table or array. When the radius is measured at the identifiable point to take blood pressure, the processor 1416 references the table from the memory 1414 and interpolates between ordered pairs, extrapolates beyond them, or uses a trend line or trend curve to estimate the blood pressure. The blood pressure is then recorded in the memory 1414.

In an embodiment, post-concussion trauma and the presence or absence of a concussion can be monitored. If images of the eye are generated continuously, then the processor 1416 can be configured (e.g., by executing processor-executable instructions stored in memory 1414, etc.) to monitor swelling, focus, and ability to visually follow an image or an item. Preferably, each eye will be monitored with an eye position sensor 1436. The processor 1416 can further be configured (e.g., by executing processor-executable instructions stored in memory 1414, etc.) to use the images and data from the eye position sensor 1436 to determine the eye's movements and focus. Preferably, the subject is given stimuli to test his ability to focus and follow with his eyes, and data on those stimuli is provided to the processor 16. In some embodiments, a sensor is configured to sense the location of an item that the subject is trying to follow with his eyes. The processor 1416 can then generate a model of what the reactions should have been and give an indication of concussion trauma or lack thereof based on comparing the results of the test to the model Data on swelling may, in some embodiments, increase the accuracy and detail of a concussion diagnosis. The eye position sensor 1436 or a similar device can be configured to measure the position of the outer surface of the eye. In some embodiments, an ultrasound or a digital camera will be able to detect swelling by changes in the position of the surface of the eye. Other methods of diagnosing concussion trauma are possible without departing from the scope of the disclosure. Swelling data can also be used for other purposes besides evaluating a concussion.

In another aspect, a visual analog scale for pain measurement is replaced by objective measurements. Instead of a subject simply choosing a number or using a similarly subjective alternative for pain measurement, objective measurements such as corneal dilation can be used to determine pain levels. This would make it easier for healthcare providers to make decisions based on pain levels, such as dosing painkillers, and would avoid the need to remind people of their pain when assessing their pain level. Other measurements may be used in conjunction with corneal dilation measurements or without corneal dilation measurements without departing from the scope of the disclosure.

Several other diseases and problems can be diagnosed in other embodiments. The memory 1414 can be configured to store retinal images and other data relating to recognizing disease by evaluating the eye E. The processor is configured (e.g., by executing processor-executable instructions stored on memory 1414, etc.) to run tests on the images taken of the subject's retina to determine if any of the documented problems might be present in the subject. Images are then compared and a healthcare provider and/or the subject are informed of possible problems. Examples of diseases and problems that can be diagnosed in this manner include diabetes, edema on the brain, easy bleeding, swelling, hypertension, vasculitis, macular degeneration, Alzheimer's, hypertension, and others. In some embodiments, a library of correlations between eye evaluation data and other measured data that indicate problems can be stored in the memory 1414. The processor is then configured (e.g., by executing processor-executable instructions stored on memory 1414, etc.) to check through all potentially relevant correlations to find suggestions of possible problems the subject might have. Some diseases, such as Alzheimer's and macular degeneration, can be detected early using an embodiment similar to one described in this paragraph. Patterns on the retina are also thought to correlate with the level of activity in the subject's brain. Readings that are too high or too low could suggest potential problems to a healthcare provider whether or not the device is configured to recognize the problems. Many other diseases and health problems can be diagnosed without departing from the scope of the disclosure.

Figure 26:
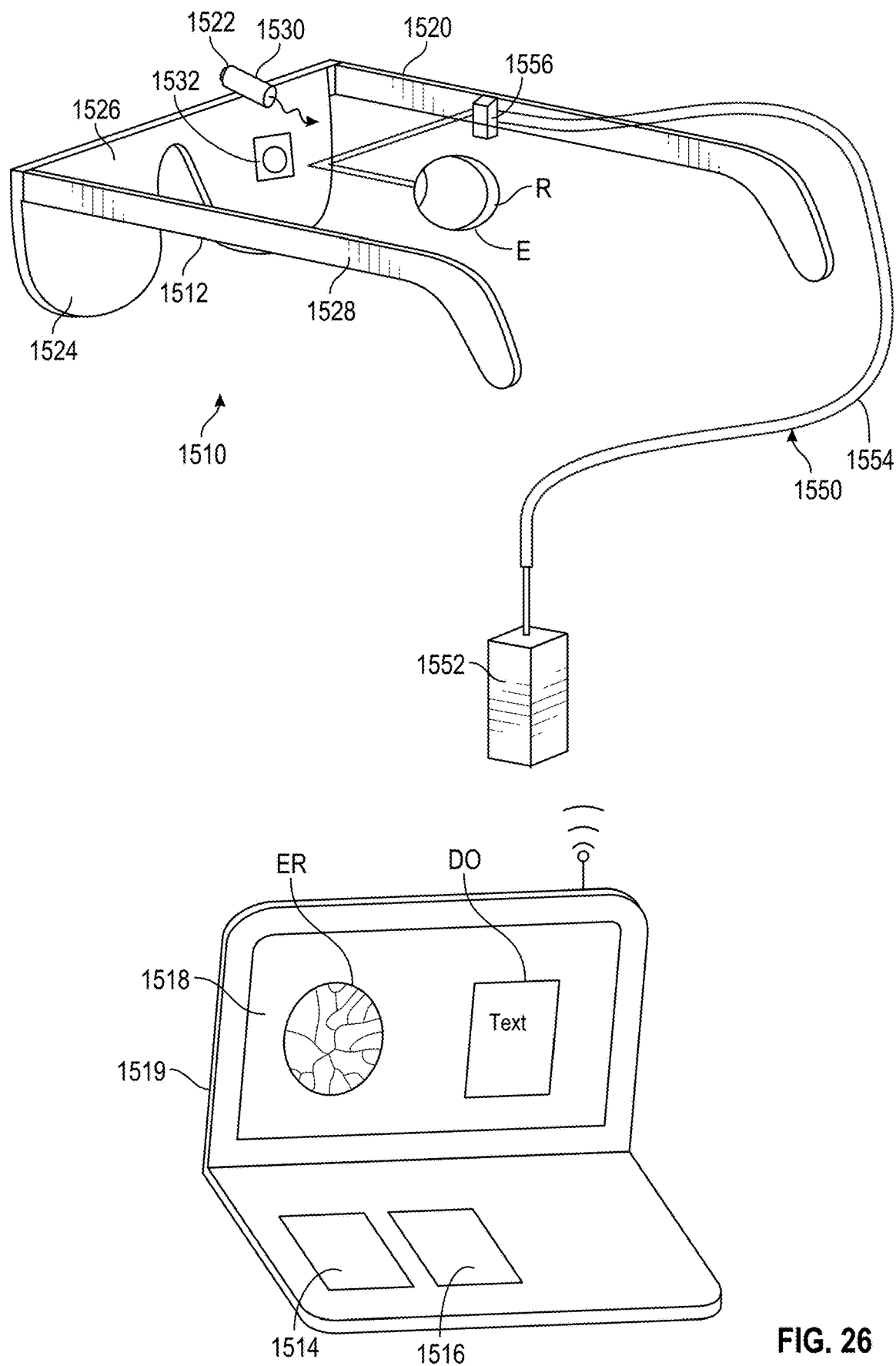
FIG. 26 is a schematic illustration of a stimulus response measurement system according to an embodiment.

Referring to FIG. 26, a stimulus response measurement system (e.g., patient monitor) is generally indicated at 1510. The stimulus response measurement system 1510 comprises an image creation system 1550 and an imaging system 1512 for evaluating responses to stimuli including responses to the images created from the image creation system 1550. Except for the image creation system 1550, this embodiment is substantially similar to the retinal evaluation system 1410, and similar parts are given similar reference numbers plus 100. A framework 1520, the imaging system 1512, and their possible variants are substantially similar to corresponding parts in FIG. 24, except that further details and variants of the imaging system 1512 are disclosed to account for the image creation system 1550 sending light to the eye E. The image creation system 1550 does not have a corresponding part in FIG. 24, and is configured to generate images to present content such as video to the user. To control the content, a processor 1516 sends content from a memory 1514 to a controller 1534 (shown in FIG. 27A). The processor 1516 can be configured (e.g., by executing processor-executable instructions stored on memory 1514, etc.) to request or control content including sound or other stimuli in addition to video or still images. The processor 1516 evaluates images generated and stored by the imaging system 1512 in conjunction with information about the content and determines reactions to the content. As explained further below, in some embodiments the processor 1516 is configured (e.g., by executing processor-executable instructions stored on memory 1514, etc.) to use results from processing images as an input to generate active, real-time feedback to adjust stimuli to the user; this real-time adjustment could, for example, make a VR/AR game more enjoyable.

In the illustrated embodiment, the memory 1514, the processor 1516, and the display 1518 are all components of a smartphone 1519 (broadly, a response processing device) that is connected to the imaging system 1512 by a wireless connection (e.g., Wi-Fi, Bluetooth, etc.). It is understood that other computing resources could be used in other embodiments. For example, it is contemplated that a laptop computing device, desktop computing device, server computing device, or another mobile computing device (e.g., a tablet computer) could be used instead of the smartphone.

Other embodiments have an onboard computer. Some embodiments do not have a display, or have information stored on a server that can be displayed by any of various computer displays. In addition, images can be stored on more than one memory and/or processed by more than one processor in certain embodiments. It is understood that the response processing device (e.g., memory 1514, image processor 1516, and the display 1518) may be in communication with the AI system 104 if the stimulus response measurement system 1510 is connected to the AI system or the AI system may take the place and perform the function of the response processing device (or one or more of the components thereof).

Figure 27A:
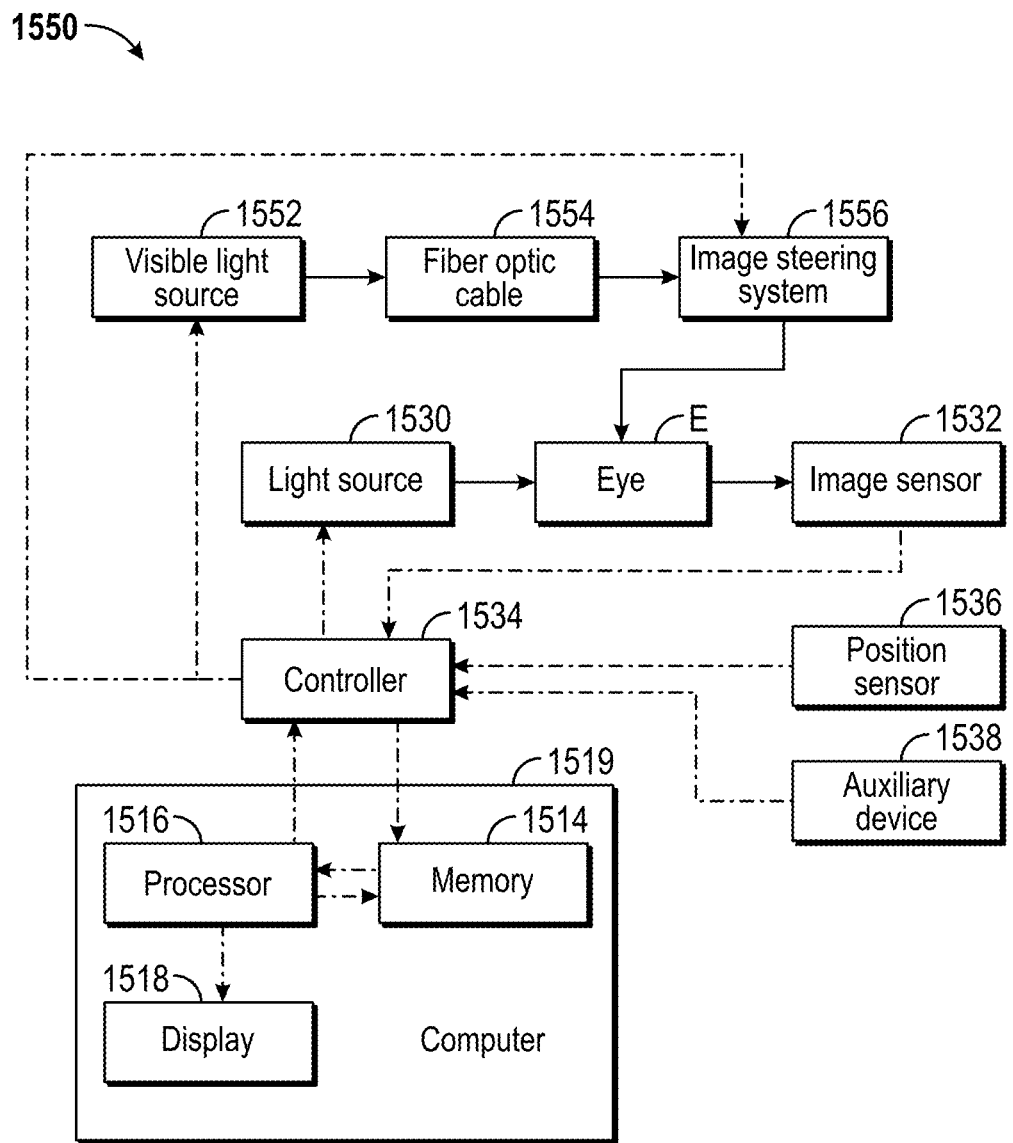
FIG. 27A is a schematic block diagram of the stimulus response measurement system of FIG. 26.
Figure 27B:
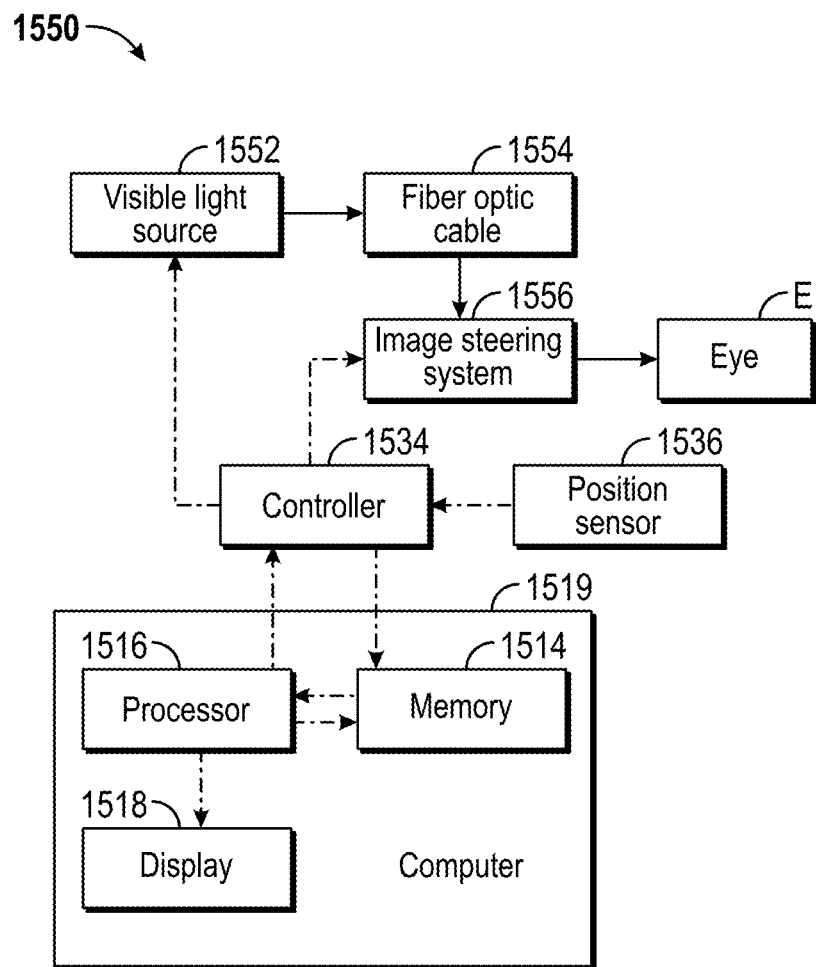
FIG. 27B is a schematic block diagram of an image creation system included in the embodiment of FIGS. 26 and 27A.

Referring to FIG. 27A, a block diagram of the stimulus response measurement system 1510 is shown. It includes elements corresponding to every element in FIG. 25A and performing approximately the same function, as well as an image creation system 1550. The imaging system 1512 and the image creation system 1550 are depicted as sharing a controller 1534, a computer 1519, and an eye position sensor 1536, but in other embodiments they are completely independent. Referring now also to FIG. 27B as well as FIG. 27A, a block diagram of the image creation system 1550, the phantom lines represent electrical signals while the solid lines represent where the device transmits light, as in FIG. 25A.

Referring to FIGS. 26 through 27B, the image creation system 1550 comprises a computer 1519 that sends direction to a controller 1534. The controller 1534 controls a visible light source 1552 which sends light through at least one optical fiber 1554 or similar device to a light steering system 1556, which is directed by the controller 1534 to redirect the light to form a virtual image directly on the retina. In some embodiments, the controller 1534 is able to modify the focal point, energy, wavelength, activation frequency, and intensity of the light or any subset of those attributes by communicating with the light steering system 1556, the light source 1530, or both. A similar system for creating a virtual image on the retina is disclosed in more detail in U.S. Pat. No. 5,659,327 to Furness, III, the entire disclosure of which is incorporated herein by reference. Optionally, the controller 1534 can communicate to the computer 1519 even if it is not sending information as part of the imaging system 1512. This could be helpful for troubleshooting, among other possible uses. For example, if communications from the controller 1534 are ongoing, then the user will know that the problem is not that the controller 1534 is out of battery or completely broken. In some embodiments, there is no optical fiber. For example, the visible light source 1552 and the steering system 1556 could be adjacent or they could be precisely aligned and have their relative positions rigidly fixed.

The light steering system 1556 relies on the eye position sensor 1536 to detect the position of the eye. The eye position sensor 1536 is depicted also as being shared with the imaging system 1512, but, as noted above, can also be separate, and is still generally used in embodiments where other data collection takes the place of the imaging system. In at least one embodiment, the eye position sensor 1536 detects the position of the eye E and stores the position in the memory 1514, and the controller 1534 is able to direct the light steering system 1556 appropriately to move or to adjust the direction of the light based on the position of the eye. In other embodiments, the light steering system 156 is configured to receive commands from the controller 1534 that tell where on the retina R to put each beam of light and receive the position directly from the eye position sensor 1536. As in the retinal evaluation system 10, in some embodiments the need for the eye position sensor 1536 can be eliminated by configuring the processor 1516 to calculate the position of the eye based on data from the imaging system 1512.

While the imaging system 1512 is configured similarly to the imaging system 1412, the image creation system 1550 sends light to the retina R which can stop pupil from dilating. Because the image creation system 1550 shines visible light at R the retina, the pupils will naturally contract, which may stop the imaging system 1512 from being able to acquire images of the retina R of sufficient quality. There are many possible solutions to this problem. In some embodiments, the light is consistently kept low enough to allow the pupils to dilate sufficiently for retinal imaging. In other embodiments, the retinal images are taken intermittently when the light is off or sufficiently low. In still other embodiments, the imaging system 1512 is configured to acquire images of the pupil, cornea, and iris, and may also be configured to collect images from the retina if possible. In at least one embodiment, the imaging system 1512 collects images from the retina of a dilated eye while the image creation system 1550 generates images for the other eye of the same subject. In this embodiment, the dilated eye may require dilating eye drops or other means of forcing dilation. Other ways of collecting retinal data while light is provided to at least one eye can be employed without departing from the scope of the disclosure. In some embodiments, the light source 1530 is unnecessary because the visible light source 1552 provides sufficient light. In other embodiments, the retinal scanning system 1440 disclosed in FIG. 25B and the accompanying description is included in place of the imaging system 1512. In embodiments including the retinal scanning system 1440, the means described in this paragraph to sufficiently dilate the pupil are also within the scope of the present disclosure.

In many embodiments, at least one auxiliary device 1538 provides additional data beyond retinal images for the processor 1516 to evaluate. In other embodiments, the at least one auxiliary device 1538 replaces the imaging system 1512. The above listing of examples of possible auxiliary devices in the description of FIG. 25A generally applies here as well. Data gathered from auxiliary devices is also stored in the memory 1514 and the processor 1516 correlates it with the stimuli that were presented most immediately before the reaction happened. Examples of properties to measure with an auxiliary device 1538 that are particularly relevant for many embodiments include sweating, indicators of relaxing and tension of muscles, changes in posture, etc. In some embodiments, auxiliary devices 1538 that are non-invasive are desirable, and in some, auxiliary devices 1538 that are mobile are desirable.

The processor 1516 is configured not only to generate data by evaluating the images collected and measurements taken, but also to correlate (e.g., by executing processor-executable instructions stored in memory 1514, etc.) that data to the content provided by the image creation system 1560 and to evaluate responses. Consistent signs across almost all people indicate different reactions, and many of those signs are reflected in the retina. Excitement, sadness, other emotions, fear, pain, and other physiological responses can be determined by examining images of the retina. The memory 1514 preferably includes a database of different profiles of what retinas look like based on different physiological and emotional reactions, and the processor is configured to navigate the database and determine reactions, preferably classifying and quantifying each response found. Brain activity can also be estimated via retinal evaluation which could help to gauge interest, for example. Other measurements taken by an auxiliary device 1538 may also be able to assist in objectively measuring reactions to different stimuli. The reactions are compared with information about the stimuli at the time so that what a user was reacting to can be determined. The processor 1516 then generates reports or information that people can understand or that the processor 1516 can use to change the stimuli or make recommendations to a user.

Figure 28:
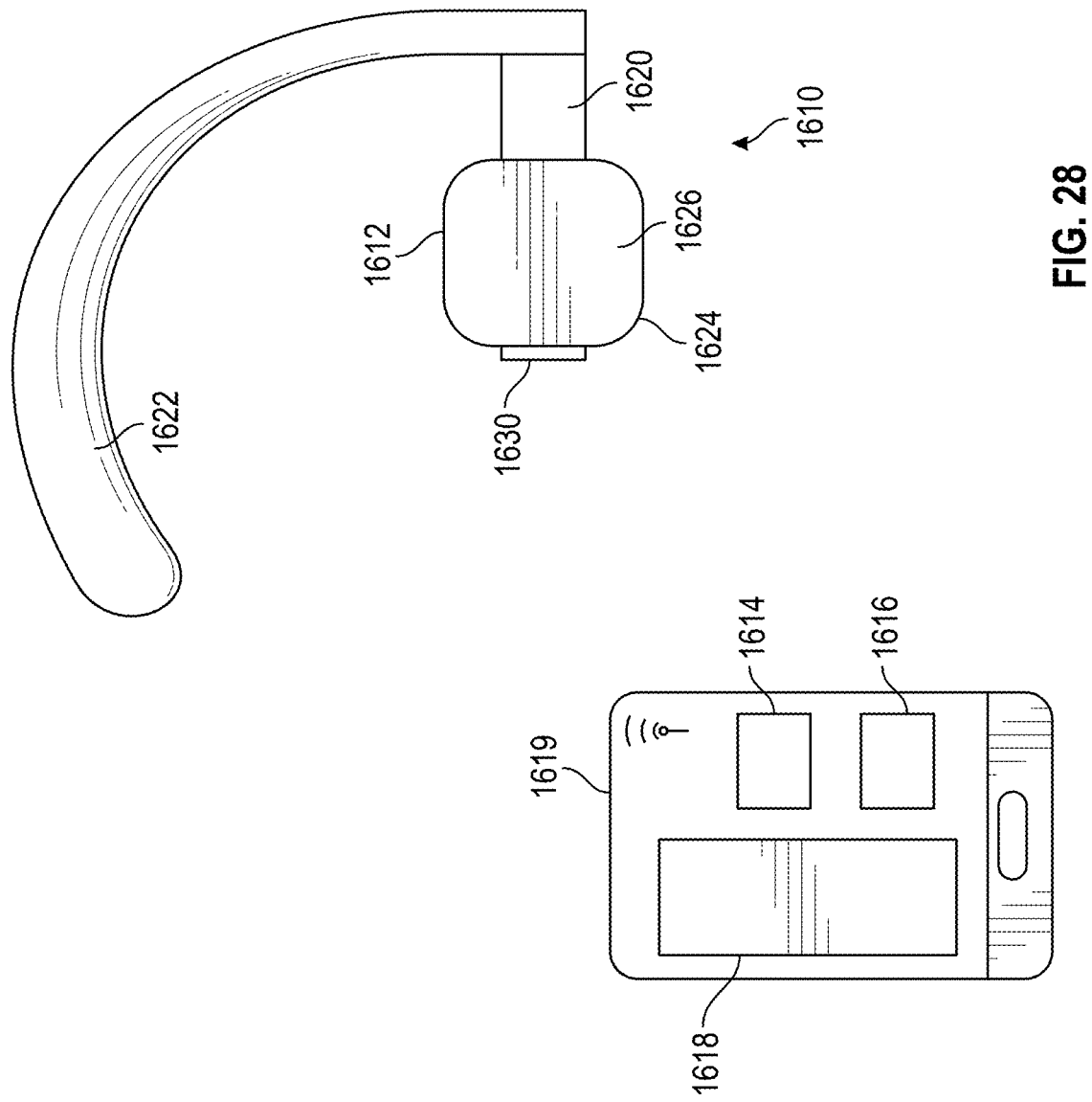
FIG. 28 is a schematic illustration of an earpiece and computer for real-time measurement of blood pressure according to an embodiment.

Referring to FIG. 28, an earpiece monitor (e.g., patient monitor) for measuring blood pressure is generally indicated at 1610. The earpiece monitor 1610 includes an earpiece 1612, and a smartphone 1619. The earpiece 1612 includes an electronics holder 1620, a support device 1622, and blood pressure sensing system 1624. The blood pressure sensing system 1624 may include parts that are positioned in the electronics holder 1620. The blood pressure sensing system 1624 works generally like a sphygmomanometer, inflating a bag 1626 in the ear and sensing the changes in sounds as the pressure in the bag 1626 matches first the systolic then the diastolic blood pressure. The blood pressure sensing system stores collected data on the memory 1614 of a smartphone 1619. A processor 1616 can manipulate (e.g., by executing processor-executable instructions stored in memory 1614, etc.) the data and send it to a display 1618. Measuring blood pressure often using the earpiece monitor 1610 allows real-time blood pressure measurements in a non-invasive way, and can be used for on-the-go, constant health monitoring.

In the illustrated embodiment, the memory 1614, the image processor 1616, and the display 1618 are all components of smartphone 1619 (broadly, a computer) that is connected to the earpiece 1612 by a wireless connection (e.g., Wi-Fi, Bluetooth, etc.). It is understood that other computing resources could be used in other embodiments. For example, it is contemplated that another computing device (e.g., a laptop or tablet computer) could be used instead of the smartphone. In addition, data can be stored on more than one memory and/or processed by more than one processor in certain embodiments. It is understood that the computer (e.g., memory 1614, image processor 1616, and the display 1618) may be in communication with the AI system 104 if the earpiece monitor 1610 is connected to the AI system or the AI system may take the place and perform the function of the computer (or one or more of the components thereof).

The earpiece 1612 is adapted to hold onto the ear and inflate a bag 1626 inside the ear to take blood pressure. The illustrated support device 1622 is configured to wrap partially around the user's ear, but could also, for example, be another type of support device such as glasses. Alternatively, the support device can be omitted and the earpiece 1612 can be configured to hold itself in by friction against surfaces inside the ear. The electronics holder 1620 is connected to the support device 1622. A pump 1628 in the electronics holder 1620 is configured to inflate the bag 1626. The bag 1626 is configured to push against blood vessels in the ear when inflated. A sound sensor 1630 is attached to the bag 1626 and is preferably pushed against the skin near a blood vessel when the bag inflates. Other embodiments are possible, for example, the tail portion can be replaced by another type of support device 1622, such as glasses, or the support device 1622 can be omitted and the earpiece 1620 can be configured to hold itself in by friction against surfaces inside the ear.

The pressure sensing system 1624 works by the same principles as a sphygmomanometer, in an embodiment. The bag 1626 is inflated to a pressure above the blood pressure and slowly deflated. The bag 1626 has an internal pressure sensor 1632 that senses the pressure in the bag and communicates the pressure to the controller 1634. When the bag pressure is equal to the systolic pressure, turbulent blood flow generates a different sound. The sound sensor 1630 is sufficiently sensitive to pick up the change. When the bag pressure is lowered to the diastolic pressure, the blood flow becomes laminar and the noise returns to normal.

Figure 29:
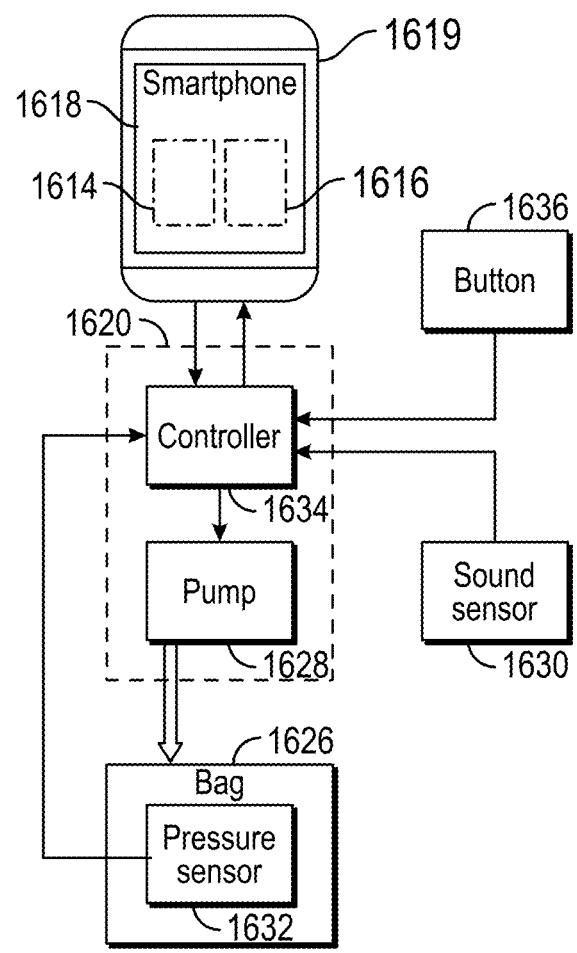
FIG. 29 is a schematic block diagram of the earpiece and computer of FIG. 28.

Referring to FIG. 29, a block diagram of the earpiece monitor 1610, the controller 1634 is directed by the smartphone 1619. When the controller receives a command to measure blood pressure, it tells the pump 1628 to inflate the bag 1626. As the bag inflates, the pressure sensor 1632 internal to the bag 1632 communicates its measurements back to the controller. Once a previously determined pressure is reached, the controller 1634 stops the pump 1628 and communicates to the pump 1628 to slowly deflate the bag 1626. As the bag 1626 deflates, the sound sensor 1630 detects changing sounds from the blood vessels for calculating heart rate and is configured to send the data to the controller 1634. The controller 1634 sends data collected to the smartphone 1619. In other embodiments, the data is sent to a server or another type of computer such as a tablet, laptop, server, or desktop. An optional button 1636 is included in some embodiments to turn the earpiece 1612 on and off. In the alternative, some embodiments have earpieces that are turned on and off remotely, for example by a signal from the smartphone 1619.

In other embodiments, instead of an inflatable bag 1626, the earpiece 1612 positions a Doppler ultrasound imaging system (FIG. 30B) or a laser imaging system (e.g., LiDar) at a point near blood vessels of the ear. The radius of at least one identifiable point on a blood vessel is measured, and compared to calibration data to determine the blood pressure. Preferably, the earpiece monitor 1610 is calibrated in such an embodiment. To calibrate the device, simply take blood pressure while the device is measuring the radius at the identifiable point and then correlate and store the collected pressures and radii as ordered pairs or as an array. While the accuracy will increase if calibration happens at multiple blood pressures, calibrating once gives a systolic and diastolic pressure. The processor 1616 can be configured to interpolate or extrapolate estimated blood pressures from calibration data.

In other embodiments using a Doppler ultrasound imaging system or a laser imaging system, the flow rate is tracked to determine change in blood pressure. The change in pressure can be determined using the following equation:

$$\text{Flow} = \frac{\Delta \text{pressure}}{R}$$

$$\text{Where: } R = \frac{8L\eta}{\pi r 4}$$

$r$ = radius inside the vessel $L$ = vessel length $\eta$ = blood viscosity

If the earpiece monitor 1610 is then calibrated to the wearer using another method of determining blood pressure, such as a sphygmomanometer integral to a system for calibrating the earpiece monitor 1610, then the blood pressure can be estimated from the calculated change in pressure. Preferably the device is calibrated at multiple pressures.

Figure 30A:
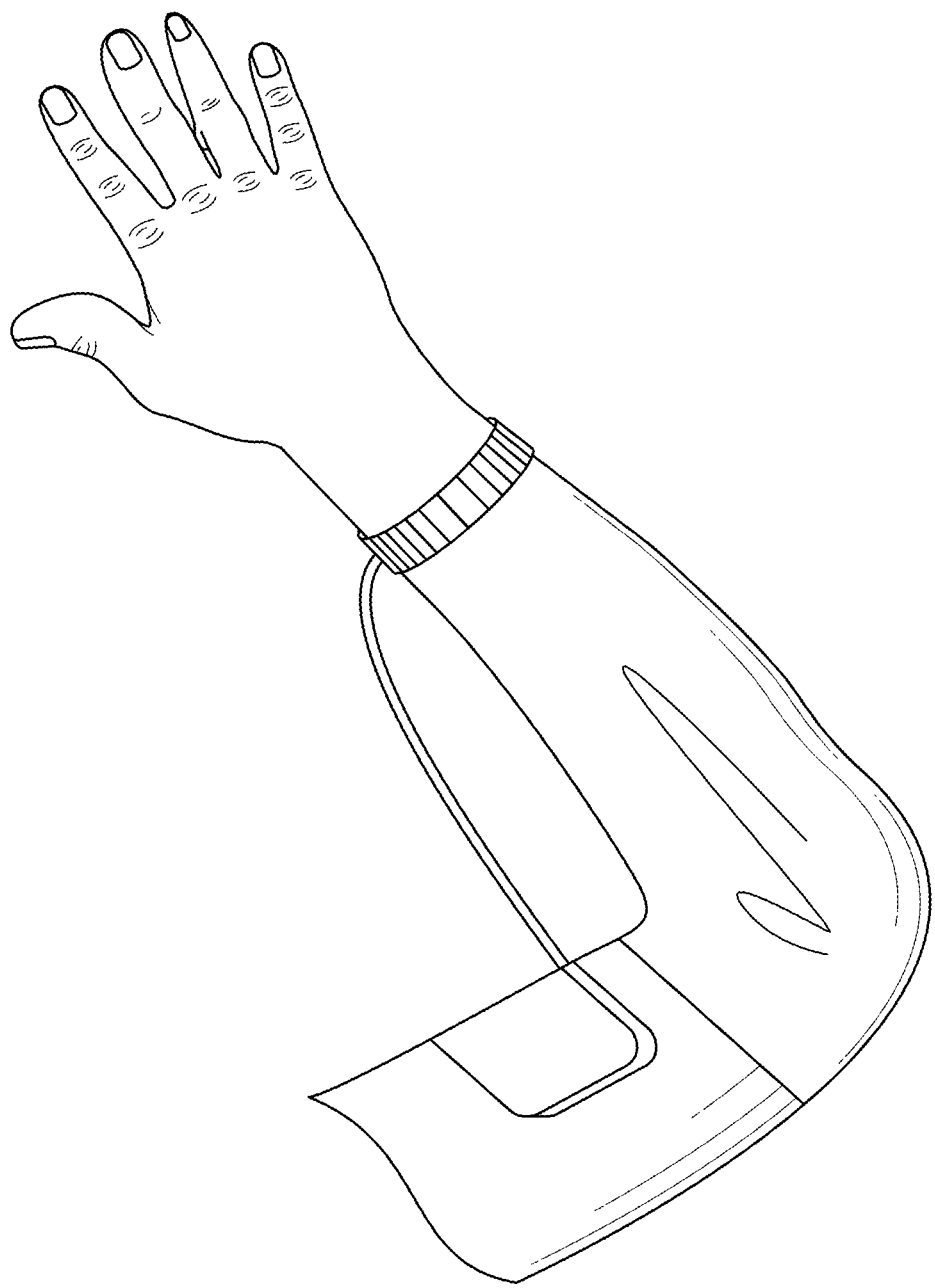
FIG. 30A is a schematic illustration of a wearable blood pressure monitor with a traditional cuff according to an embodiment.

Using the above relative pressure measurement, aspects of the present disclosure calibrate the readings with a traditional cuff to create a system that is enabled to track changes in blood pressure for remote monitoring. As illustrated in FIG. 30A, an exemplary system includes a traditional cuff that includes a controller, a disconnecting wire, and a wrist monitor that includes a transducer. In one embodiment, the system is wireless and does not include the disconnecting wire. When the wrist monitor is an ultrasound monitoring system, the system is placed over the user's wrist and the relative pressure is measured using the above equations. To calibrate the system, the cuff with integrated pump circuitry is attached to the system. The controller of the cuff then calculates the conventional systolic and diastolic pressures. These measures are used as a baseline measurement and increases and/or decreases from the baseline measurements are calculated based off ranges in blood flow.

Figure 30B:
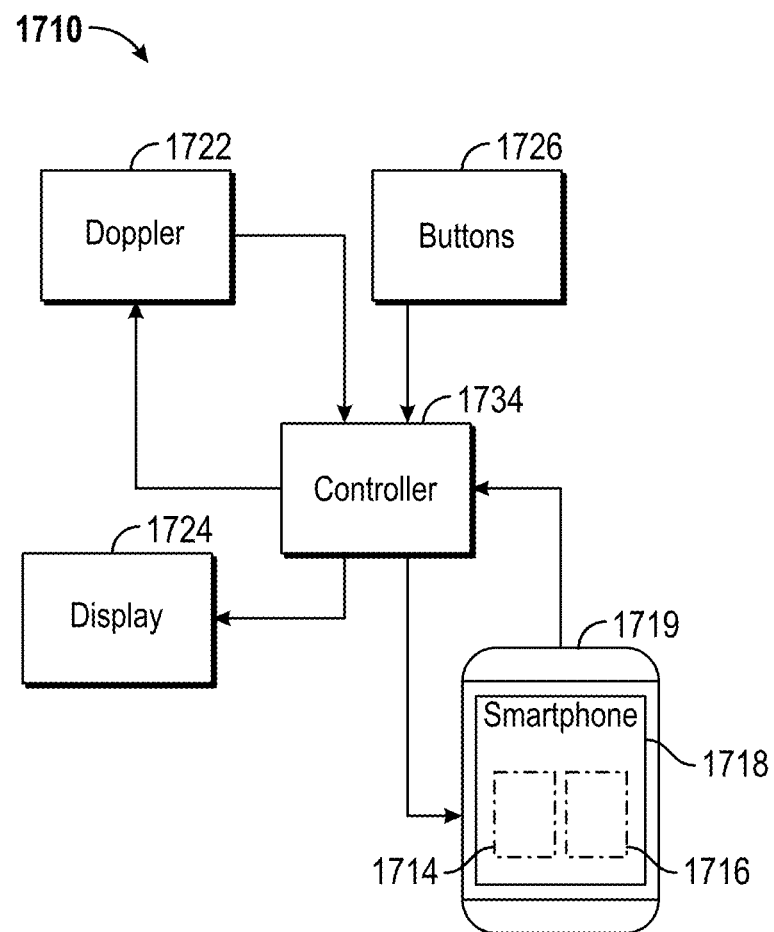
FIG. 30B is a schematic block diagram of a wearable blood pressure monitor according to an embodiment.

Referring to FIG. 30B, a wrist-wearable monitor (e.g., patient monitor) for blood pressure is generally indicated at 1710. The wrist-wearable monitor 1710 comprises a smartphone 1719 and a wristpiece 1720. The embodiment shown uses a Doppler ultrasound imaging system 1722 to measure the radius of at least one known blood vessel. The radius is stored in a memory 1714 and a processor 1716 can use the radius to estimate blood pressure. By timing the changes in radius of the blood vessel, heart rate can be measured as well. A display 1724 is configured to optionally display blood pressure and heartbeat, and a controller controls the device and communicates with a smartphone 1719.

In the illustrated embodiment, the memory 1714, the processor 1716, and a display screen 1718 are all components of the smartphone 1719 that is connected to the wristpiece 1720 by a wireless connection (e.g., Wi-Fi, Bluetooth, etc.). It is understood that other computing resources could be used in other embodiments. For example, it is contemplated that another computer (e.g., a laptop, sever, desktop, or tablet computer) could be used instead of the smartphone. In addition, images can be stored on more than one memory and/or processed by more than one processor in certain embodiments. It is understood that the smartphone 1719 (e.g., memory 1714, image processor 1716, and the display 1718) may be in communication with the AI system 104 if the wrist-wearable monitor 1710 is connected to the AI system or the AI system may take the place and perform the function of the smartphone (or one or more of the components thereof).

Figure 31:
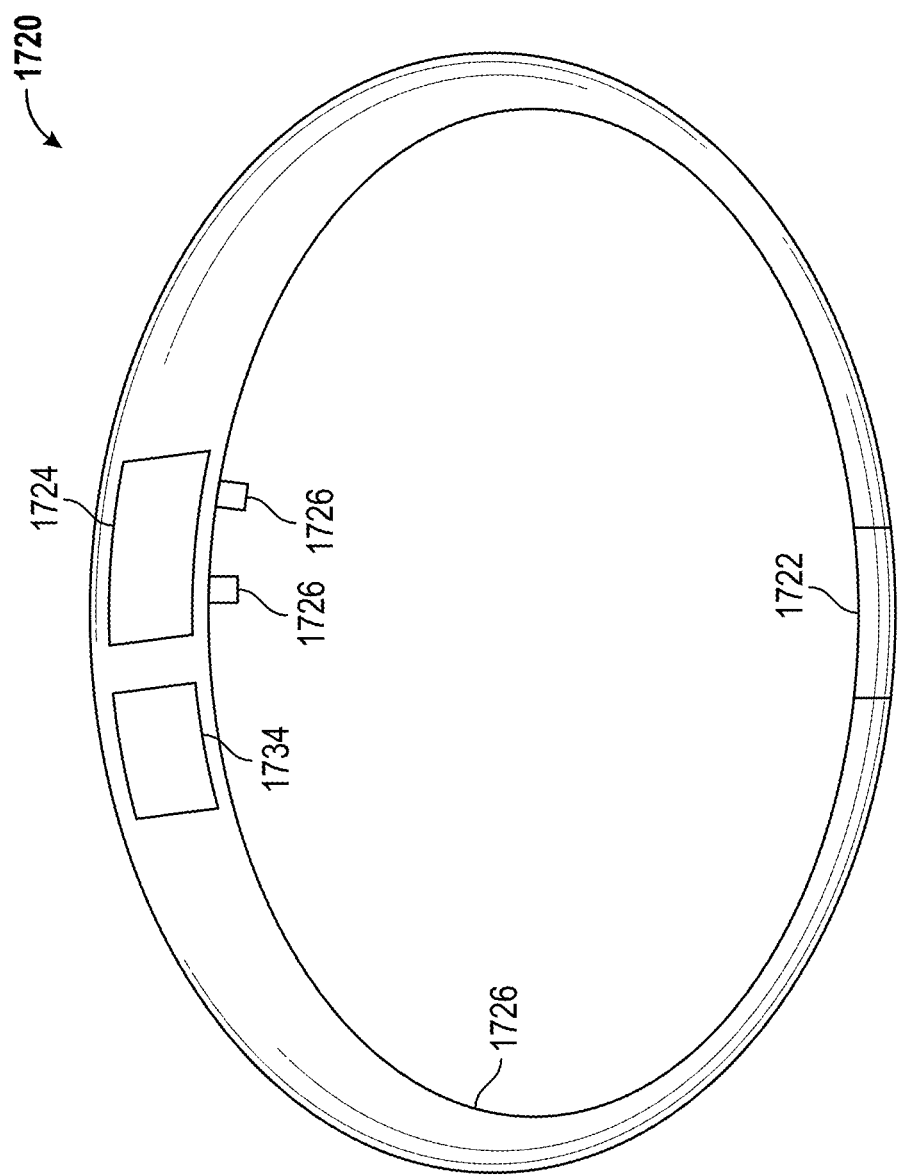
FIG. 31 is a schematic illustration of a wrist-wearable embodiment of the wearable blood pressure monitor of FIG. 30B.

Referring to FIG. 31, the body 1726 of the wristpiece 1720 comprises a flexible wristband that is preferably worn slightly tight in order to get the best reading from the Doppler ultrasound imaging system 1722. The body 1726 partially encloses a Doppler ultrasound imaging system 1722, and holds a controller 1734, the display 1724, and buttons 1726 in place. In alternate embodiments, the wristband 1712 is configured like a watch with a clasp or buckle.

A wristpiece 1720 is preferably configured to position the Doppler ultrasound imaging system 1722 over the soft underside of a forearm of a user, near the user's wrist. The Doppler ultrasound imaging system 1722 measures the radius of a known blood vessel and sends that data to the controller 1734. The controller 1734 sends data to the display 1724 and to memory 1714 the smartphone 1719. In some embodiments, no display is used in the wrist-wearable monitor, and in some other embodiments, the data is not transmitted and the data is accessed through the display 1724. Buttons 1726 are near the display 1724 and allow the display 1724 to be turned on and off for privacy and allow the device to be turned off to conserve battery. In some embodiments, the wristpiece 1720 might have minimal internal circuitry and transmit the raw measured data to the memory 1714, while in other embodiments the controller can calculate blood pressure, average blood pressure, etc. The wristpiece 1720 preferably has internal memory as well. In some embodiments, the data collected it could be transmitted to a server and made available to the user's physician, via a smartphone application, via a website, or both. The data could also be sent to an insurance carrier or other interested third party. Some embodiments include a laser imaging system (not shown in the drawing) instead of a Doppler ultrasound imaging system 1722. A laser imaging system can collect the same information in a similar manner and relay the information in the same way as the Doppler ultrasound imaging system described herein.

In a preferred embodiment, previous calibration allows the processor to accurately estimate blood pressure based on radius measurements stored in the memory 1714. Calibration can be done according to the method described above in the description of FIGS. 28-30A. After the device is calibrated, the processor can interpolate between recorded points or extrapolate beyond them. If blood pressure is measured several times for calibration, then a trend line or a trend curve could be generated to account for noise.

In another embodiment, a Doppler ultrasound imaging system 1722 or a laser imaging system is used to track change in blood pressure over a distance in a blood vessel and estimate blood pressure. The flow rate and the radius can be measured, and the change in pressure can be determined using the equations disclosed in relation to calculating blood pressure via ultrasound or laser imaging system in the earpiece monitor 1610 of FIGS. 28 and 29. In an embodiment, the wrist-wearable monitor 1710 is then calibrated to the wearer just as described above, except that changes in pressure rather than radii are correlated with pressures. As described above, the processor 1716 can then use interpolation, extrapolation, or a trend line or trend curve to calculate blood pressures. Other methods are also possible without departing from the scope of the disclosure.

A technical advantage of using a wrist-wearable monitor 1710 instead of an earpiece monitor 1610 is the availability of large blood vessels. A wrist-wearable monitor 1710 will generally lead to more precise estimates of blood pressure than an earpiece because a given measurement error of, for example, 0.1 millimeters, would be a much larger percentage error when measuring the diameter of a small blood vessel in the ear than when measuring the diameter of a comparatively large blood vessel in the wrist.

Other embodiments include a wristpiece 1720 similar to the one shown in FIG. 31 that precisely detects the radius of at least one blood vessel. Using the elasticity of a known blood vessel, a known radius of the same vessel, and a blood pressure corresponding to the known radius, the current blood pressure can easily be calculated. To estimate elasticity, the device can be calibrated to the user. Elasticity can be estimated using calibration data, where each point of calibration data preferably includes the radius of the known blood vessel and a corresponding blood pressure. Other methods of estimating elasticity are also possible Both the wrist-wearable monitor 1710 and the earpiece 1610 are not only standalone devices, but also, in some embodiments, part of a device that incorporates retinal imaging, imaging of other parts of the eye, or both. Performing retinal imaging in real time and using one of the disclosed devices to determine blood pressure in real time, with or without other measured input data, provides a wealth of information about physiological and emotional responses as well as health. A preferred embodiment includes the retinal evaluation system 1410 or the stimulus response measurement system 1510 in combination with either the earpiece 1612 of the earpiece monitor 1610, or the wristpiece 1720 of the wrist-wearable monitor 1710.

Any of the disclosed aspects can be configured so that medical data can be collected by insurance companies. This is especially useful for embodiments that are worn during everyday activities and that continuously monitor health, because it allows insurance companies to engage in price discrimination, encourage low-risk behavior, and suggest doctor's visits when the data shows that it will statistically save the insurance company money. Insurance companies can use the data to set rates or offer discounts. To encourage healthy behavior, discounts can be offered based on specific health outcomes that are more within the control of the insured than medical outcomes that directly impact the company's bottom line (i.e., the blood pressure of the insured is more within the control of the insured than whether the insured has a heart attack). Other forms of price discrimination are also enabled. The insurance company can also use the data if they question the need for different medical procedures and to suggest to customers at high risk for different problems that they see a doctor about those problems.

Having now described various physical aspects, in addition to some briefly described methods, more general methods of using devices similar to those presented above are disclosed. It is understood the methods disclosed below can be performed by the devices alone or with the AI system 104 or a combination of both.

Figure 32:
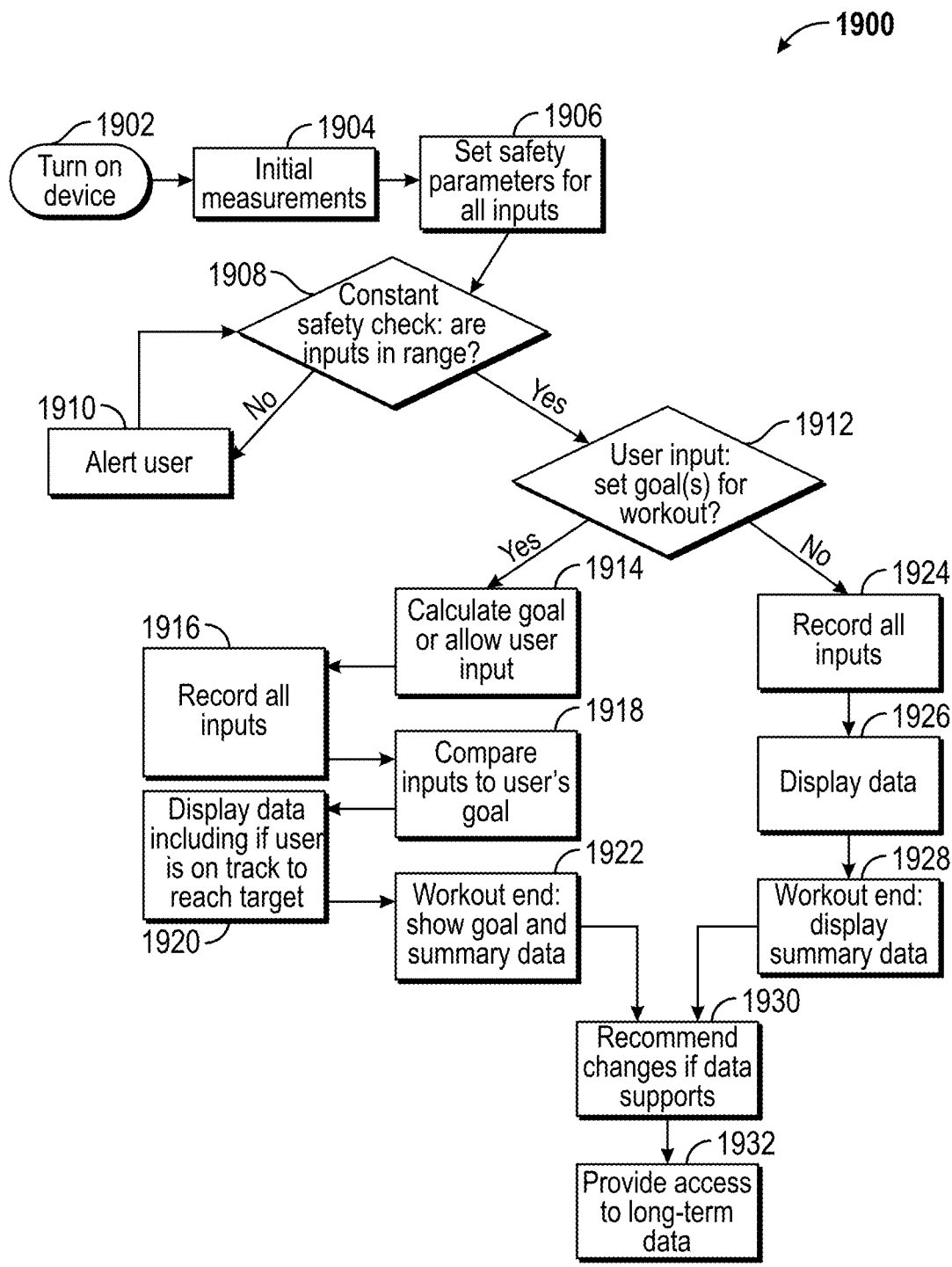
FIG. 32 is a flow chart of evaluating exercise through continuous measurements according to an embodiment.

Referring to FIG. 32, an exemplary method of workout tracking and measurement is generally indicated at 1900. In an aspect, method 1900 is an algorithm comprising processor-executable instructions embodied on a storage memory device of a computing device to provide workout tracking via a software environment. For example, the algorithm of method 1900 may be provided as processor-executable instructions that comprise a procedure, a function, a routine, a method, and/or a subprogram utilized independently or in conjunction with additional aspects of the methods, systems, and/or devices described herein according to exemplary embodiment of the disclosure. For example, method 1900 is executed by a computer, such as one or more of computer 1419, computer 1519, computer 1619, and computer 1719 in accordance with one or more embodiments of the disclosure and/or with the AI system 104.

First, the device is turned on in step 1902. Initial measurements are taken in step 1904 to use as a resting baseline for the day. Based on general guidelines and known information about the user, safety parameters are set for each input in step 1906. In addition to data from retinal imaging as further described herein, an auxiliary device 1438 can be used to collect data. Any of the listed auxiliary device possibilities that are mobile and non-invasive are helpful in some embodiments as auxiliary devices, as is a GPS, among other possibilities. For all medical inputs measured, a safe range is determined or referenced. At decision point 1908, if any input is out of range, the user is notified immediately in step 1910, and other steps may stop in some embodiments. This check is preferably made with every medical measurement. In some embodiments, a retinal evaluation determines if the person is in pain, and if the person is in enough pain to pose a danger, then in step 1910 the device will tell them to stop or decrease the intensity of their exercise. While inputs are within determined safe ranges at 1908, the process proceeds to 1912. At step 1912, the user decides if she wants a goal for the workout. In some embodiments, the device optionally calculates a goal based on the time the user plans to spend and the longer term goals of the user. If the user inputs a desire to have a goal at 1912, the goal or goals are calculated or input at step 1914 and the workout can begin. Steps 1916 to 1920 happen continuously during the workout. All input measurements are recorded in step 1916 and compared to the daily goal in step 1918. In step 1920, the visual display displays data to the user, including data indicative of whether she is on track to meet her goal or goals. When the workout is over, summary data and how it compares to the workout goal or goals is displayed on the visual display in step 1922. Examples of goals that some embodiments could track include distance biked, estimated calories burned, speed run, peak heart rate, and the like. In one embodiment, the summary data includes comparisons, such as percentile rankings, to other users of similar ages and physical makeup (e.g., weight) which may be compiled by the AI system 104.

If at step 1912 the user does not choose to use the device to track any goals, then the device records all inputs in step 1924. Data relating to the inputs is displayed in step 1926. In step 1924 and 1926 in some embodiments, a processor uses retinal evaluation to estimate energy levels and determine if the device should encourage the user to increase the intensity, or suggest that the current intensity level might not be sustainable for the time the user plans to exercise. In step 1928, summary data is displayed on the visual display when the workout ends. The data displayed during and after the workout can be customizable in some embodiments. Any input or calculated figure such as speed, averages, current numbers, or other statistically calculated numbers can be displayed, preferably according to the user's preference. Especially in the case where goals are not displayed, personal highs, personal averages, or other baselines can be displayed for comparison. Preferably the device would communicate in real-time through a smartphone application or a wearable display, but there are other possibilities including projecting an image onto the retina.

Regardless of whether the goal-tracking features were used, in step 1930 the device takes data from multiple workouts and recommends changes if it can support them by data collected, including any previously stored data. The data is stored in step 1932 to provide long-term access to the user. In some embodiments, this data is correlated with other health data which could include any of the data already mentioned in other parts of the specification.

Figure 33:
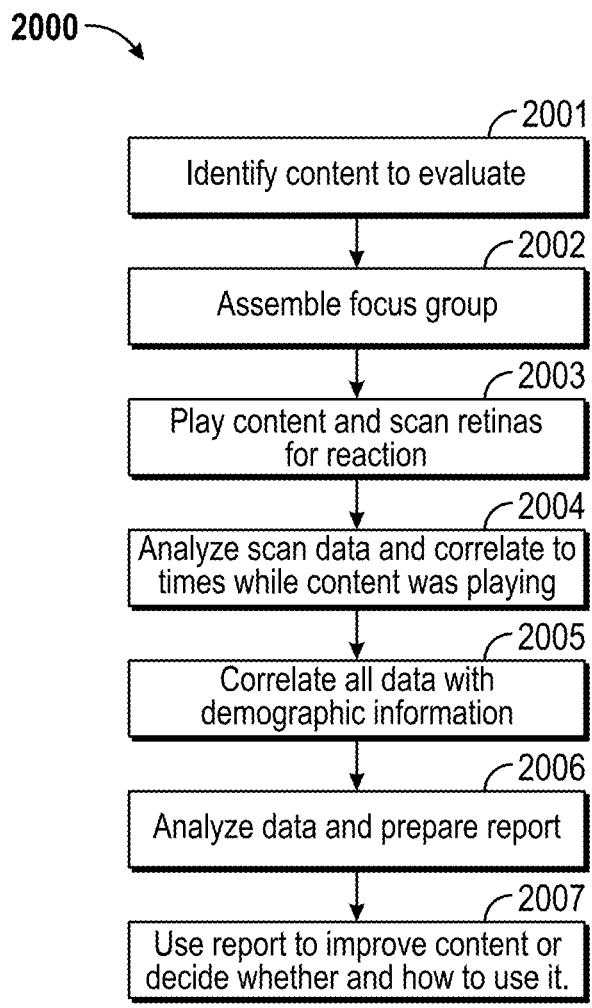
FIG. 33 is a flow chart of a method of performing research studies using real-time measurements of the subjects of the study to determine reactions according to an embodiment.

Referring to FIG. 33 a method of collecting data from a focus group, generally indicated at 2000, is disclosed. In an aspect, method 2000 is an algorithm comprising processor-executable instructions embodied on a storage memory device of a computing device to provide collection of data from a focus group via a software environment. For example, the algorithm of method 2000 may be provided as processor-executable instructions that comprise a procedure, a function, a routine, a method, and/or a subprogram utilized independently or in conjunction with additional aspects of the methods, systems, and/or devices described herein according to exemplary embodiment of the disclosure. For example, method 2000 is executed by a computer, such as one or more of computer 1419, computer 1519, computer 1619, and computer 1719 in accordance with one or more embodiments of the disclosure and/or with AI system 104.

In step 2001, content to evaluate is identified. Content could include trailers for movies, music, political or other ads, books, and entertainment content such as games or movies. It could also include other videos, sound recordings, or something live. In step 2002, a focus group is assembled. This can be done physically or virtually. For example, anyone with the right retinal imaging system can participate from anywhere. In some instances, people might be selected without their knowledge. Bases for selection in that case would most likely include a prior more general consent and choosing the content. In step 2003, the content is presented and data is gathered regarding reactions. The data could be retinal images, but could also include changes in blood pressure and heart rate; other data that indicates the reaction to the content such as sweating, coughing, fidgeting, or relaxing, for example; or a combination of multiple pieces of raw data. Preferably, the data is gathered automatically. As data is gathered or at a later point, it is analyzed in step 2004. Not only can the people running studies or focus groups get quantified reactions in general, but they can see what reactions were like at different times, and thereby understand more specifically what people were reacting to. Step 2005, which may be done concurrently with, before, or after step 2004, increases the precision of the results. In step 2005, all reactions are correlated with existing demographic information for each participant. In some cases other relevant information is asked of participants and is also correlated. For example, if a focus group is evaluating a trailer for a new Star Wars movie, then knowing who was already a Star Wars fan is important. Step 2005 is omitted in some embodiments. A report is prepared in step 2006 to help the study's sponsor understand things like what reactions the content evoked, what parts were most popular, how different demographic groups responded, etc. Finally in step 2007 the sponsor uses the information as she sees fit. For example, the content can be improved, targeted to the right audience, or discarded. It could also be made in different versions, to target different groups, for example.

Method 2000 has broad application to market, sociological, political, and psychological studies. Evaluating images of the retina and other parts of the eye can reveal excitement, sadness, other emotional responses, non-emotional responses such as pain, and physiological responses. This would be useful for getting an objective measure of the reactions of focus group members looking at new products or ads, allowing physicians or psychologists to gauge appropriateness of reactions to stimuli including pain, seeing what people think of political ads, determining whether people like something that they won't admit they like, etc. In some embodiments, a person or processor controlling the stimuli could receive reports of reactions in real time and adjust stimuli to select content for a subject or group based on reactions to the previous content.

Methods similar to method 2000 can be used to track individual responses for use by psychologists, doctors, or simply for curious users. For example, a psychologist can see whether someone's reactions are normal and what they tell about a person based on data that the person might never be able to communicate. A physician can do more than checking reflexes in a traditional way, and see if the retina or other measurements indicate that a patient has healthy internal reactions to different stimuli.

Some embodiments appropriate for method 2000 are mobile and a user could wear one or more devices implementing method 2000 all throughout a normal day, while others not wearable and in some cases require comparatively large machines to take the desired measurements. For example, in some embodiments, the retina scanner and/or monitor can be integrated into a smartphone, tablet and/or TV to monitor the user's response to the screen.

Figure 34:
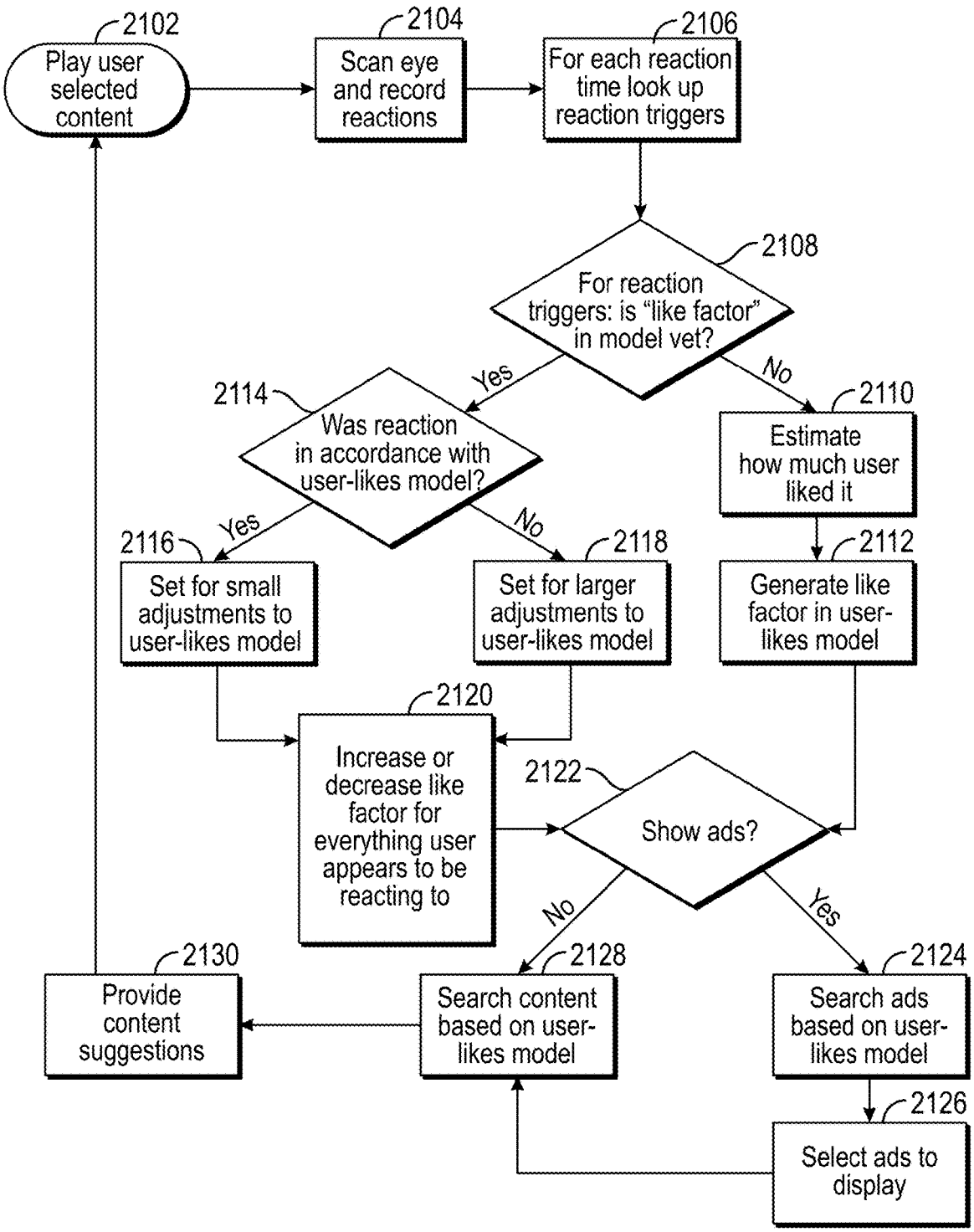
FIG. 34 is a flow chart of a method of using real-time measurements of a content viewer to recommend content and select relevant ads according to an embodiment.

Referring to FIG. 34, some embodiments could be used for recommending content and selecting ads to show. If an embodiment such as the embodiment illustrated in FIG. 3 is used for significant content consumption such as videos, then some embodiments could go even further through continual monitoring via retinal imaging and evaluation. The data could be used to determine whether a user wants to skip the intro of his favorite show, estimate how much content the user wants to have suggested, and estimate when ads can be shown for maximum attention or for minimum annoyance by tracking the user's reaction as he sees ads at different times. It would also aid in ad selection by watching his reaction as he sees the ads. For example, if he gets excited often by trucks, then he would see more trucks, and which trucks excited him would be tracked to allow more targeted advertising. Recording such reactions could also be used for advertising via other media including phone, email, or traditional mail.

FIG. 34 discloses a method, generally indicated at 2100, that can be used for recommending content and selecting advertisements. In an aspect, method 2100 is an algorithm comprising processor-executable instructions embodied on a storage memory device of a computing device to provide content recommendation and/or advertisement selection via a software environment. For example, the algorithm of method 2100 may be provided as processor-executable instructions that comprise a procedure, a function, a routine, a method, and/or a subprogram utilized independently or in conjunction with additional aspects of the methods, systems, and/or devices described herein according to exemplary embodiment of the disclosure. For example, method 2100 is executed by a computer, such as one or more of computer 1419, computer 1519, computer 1619, and computer 1719 in accordance with one or more embodiments of the disclosure and/or with AI system 104.

As the device (e.g., computer) performs step 2102, playing user selected content, it continuously or intermittently performs step 2104, imaging the eye and evaluating the images for reactions to content. Step 2104 also includes gathering images from any applicable auxiliary devices. The timing of step 2104 can be determined by analysis of the content. Things identified in the content that might trigger a reaction, or "Reaction Triggers," can be used to know when to acquire an image of the retina. In step 2106, for each reaction to the content that is captured, the time of the reaction is used to determine which Reaction Triggers the user might be reacting to. In this embodiment, a model called the user-likes model uses "Like Factors," which are assigned to Reaction Triggers to determine what a user is likely to enjoy. One thing can have several Reaction Triggers ranging from concrete to abstract (e.g., swordplay to violence) and from specific to general (e.g., from "red Maserati" to "car"). At decision point 2108, each Reaction Trigger is checked to determine if there is a Like Factor for it. If not, then in step 2110 a quick estimate is made of how much the user liked it and a Like Factor is generated in step 2112. If sufficient data is available and the program is able to use it, then a more specific classification of the reaction is recorded. For example, if the user finds it funny instead of thrilling, that information may help understand what users want. Understanding whether the user is laughing, on the edge of his seat, or fascinated can help sort through which Reaction Triggers are driving his reaction as well if several happen at about the same time. Additionally, preexisting Like Factors can be consulted in generating like factors. For example, if a user loves dogs, but no Like Factor exists for a collie, and a reaction trigger that has a negative Like Factor happens at the same time as the user sees a collie, then a good reaction might be attributed entirely to the collie.

If a Like Factor already exists for the Reaction Trigger, then the program assesses at decision point 2114 whether the reaction generally fit the expectations of the user-likes model. If it did, then the appropriate variable is recorded in step 2116 to indicate that only very minor adjustments to the user likes model need to be made. If the user-likes model was not close, then the variable mentioned is set to make a slightly larger adjustment to the model in step 2118. After the variable for how much to change the model is set, the Like Factor for each Reaction Trigger is increased or decreased appropriately in step 2120. At this point, the model is fully updated with the reaction information. At decision point 2122, the program determines if it should look for ads to show. In similar methods, the answer may always be yes or always be no. If yes, then in step 2124 ads are sought using information from the user-likes model. After finding potentially relevant ads, the program determines which ads to display in step 2126. This decision could optionally weigh information about which ads were found relevant in the past. After ads are selected or if ads are not sought, content that might be recommended is searched in step 2128 based on data from the user-likes model. Finally, in step 2130, content suggestions are selected and displayed. When the user chooses suggested or other content, the process begins again.

Steps 2124 and 2126, searching for and selecting ads, can also be performed separately and can be used to advertise in other ways. For example, more information could be sent by phone, email, or traditional mail. Once a user has spent enough time with the device, commercials are more relevant than software of similar sophistication to that used on the device has been able to make them in the past. Further, similarly relevant ads via other media can be presented to the user.

Figure 35:
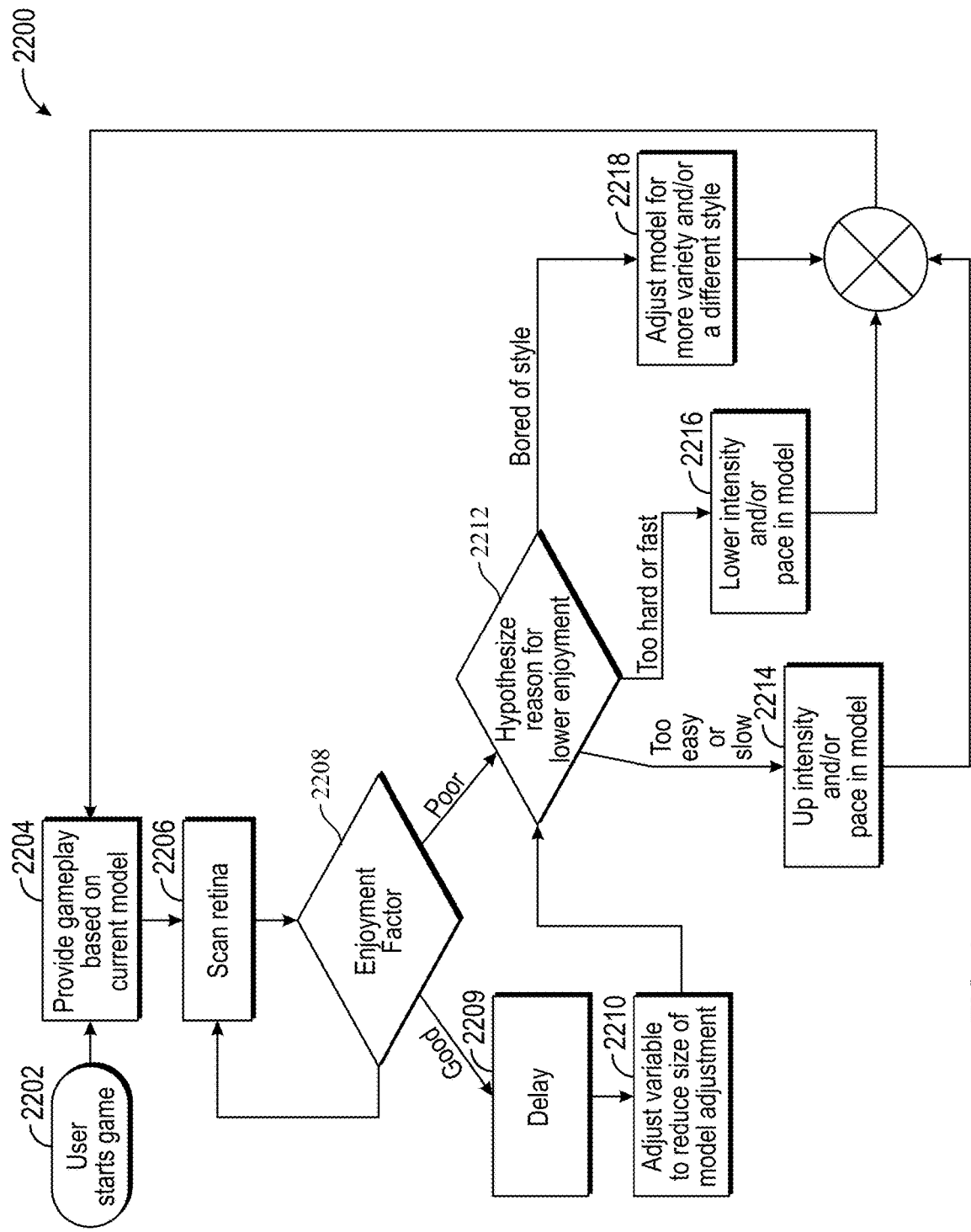
FIG. 35 is a flow chart of a method of adjusting a simulation based on real-time measurements of the user according to an embodiment.

Referring to FIG. 35, a method of using a retinal evaluation device for gaming simulations is generally indicated at 2200. In an aspect, method 2200 is an algorithm comprising processor-executable instructions embodied on a storage memory device of a computing device to provide retinal evaluation for gaming simulations via a software environment. For example, the algorithm of method 2200 may be provided as processor-executable instructions that comprise a procedure, a function, a routine, a method, and/or a subprogram utilized independently or in conjunction with additional aspects of the methods, systems, and/or devices described herein according to exemplary embodiment of the disclosure. For example, method 2200 is executed by a computer, such as one or more of computer 1419, computer 1519, computer 1619, and computer 1719 in accordance with one or more embodiments of the disclosure and/or with AI system 104.

In embodiments designed for entertainment or leisure, feedback gleaned from retinal imaging and evaluation can help a computer determine what a user enjoys. A game could use this information to determine pace, intensity, and content provided to the user, for example. In step 2202, the user starts the game. The gameplay proceeds based on a model of what the user likes in step 2204. If the user is new to the game, a default model can be used, or the game can be adapted to work without a model as well. All other steps preferably occur while step 2204 continues. As the user plays, the retina is imaged at step 2206. In addition to or instead of imaging the retina, other measurements could be taken that indicate reaction, such as heart rate and blood pressure for example. At decision point 2208, the user's enjoyment level is calculated by evaluating the retinal image. If the enjoyment level is sufficiently high, or perfect, the game continues without any updates to the model, and retinal images are captured and evaluated in step 2206 until an adjustment to the game is needed. If the enjoyment level is high, but could be higher, then only a slight adjustment is needed. There is a slight delay 2209 and in step 2210 a variable is adjusted to indicate that updates to the model should be smaller than they would be. At this point, or immediately after enjoyment level is found to be poor, a reason for lower enjoyment is hypothesized as shown at decision diamond 2212, which determines updates to the model of the user's preferences. For example, if the user seems bored, then based on previous experiences and how well the user is doing, the game might determine that it is too easy or slow, and increase pace or intensity or both as indicated at step 2214. In the alternative, it might decide that retinal images indicate boredom, but that the player is bored of the style, and adjust the style of gameplay in step 2218. On the other hand, if the user is frustrated, then the intensity and/or pace can be lessened at step 2216. In any of steps 2214-2218, or in other adjustments to the model of which these are only examples, the gameplay is not adjusted directly, but the model is updated, which will determine changes in gameplay. In other embodiments, the game could also be directly updated so that the model is stable and the difference can still be felt quickly. Gameplay is continued based on the updated model, returning to step 2204.

Many features of different embodiments such as those described in the previous paragraph could be done with opaque eyepieces, which can be used for a virtual reality, or alternatively with darkened but transparent lenses, which can be used, for example, for an augmented reality simulation. Information collected to determine pace, intensity, etc. can be used not only to determine what the player wants at the time, but can be used more generally for the player's experience with the game and in some cases even to evaluate potential updates for all players.

Method 2200 is used for training simulations in one or more embodiments. For example, in a high intensity military or self-defense training, the retinal images could reveal data relating to whether the person training feels scared. If the person does not feel scared, perhaps something could change to increase the intensity of the simulation in an attempt to force the person training to practice reacting to fear.

Figure 36:
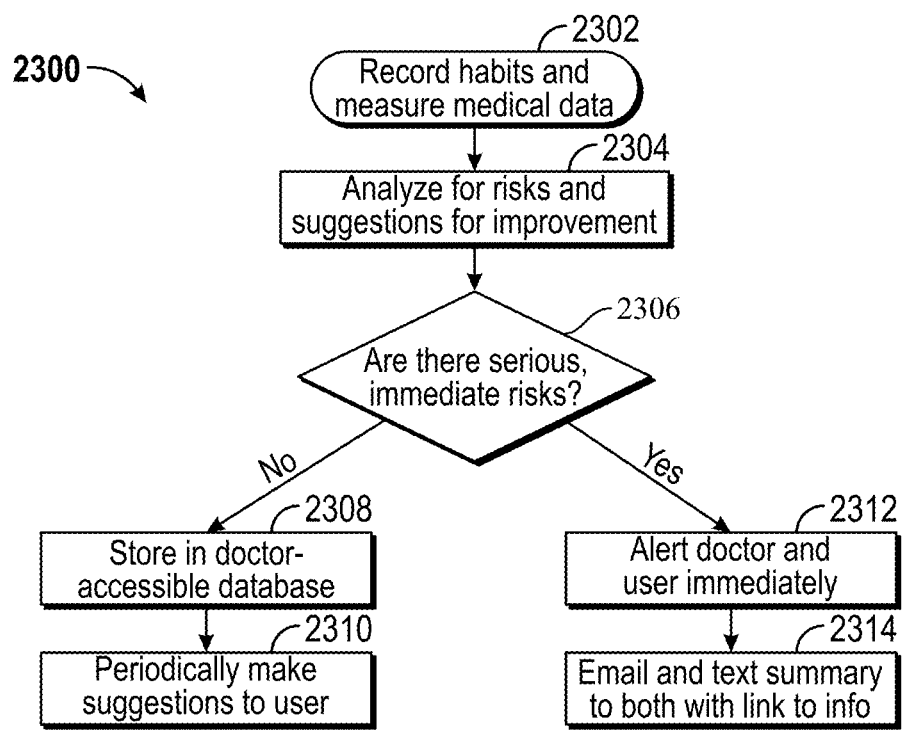
FIG. 36 is a flow chart of a method of continuously monitoring health by taking real-time measurements of the user according to an embodiment.

FIG. 36 is a diagram of a method of use for tracking health, which is generally indicated at 2300. In an aspect, method 2300 is an algorithm comprising processor-executable instructions embodied on a storage memory device of a computing device to provide health tracking via a software environment. For example, the algorithm of method 2300 may be provided as processor-executable instructions that comprise a procedure, a function, a routine, a method, and/or a subprogram utilized independently or in conjunction with additional aspects of the methods, systems, and/or devices described herein according to exemplary embodiment of the disclosure. For example, method 2300 is executed by a computer, such as one or more of computer 1419, computer 1519, computer 1619, and computer 1719 in accordance with one or more embodiments of the disclosure and/or with AI system 104.

In step 2302 medical data is gathered such as heart rate, information from retinal evaluations, blood pressure, and insulin and blood sugar levels, among other possibilities. Habits relating to health are also measured or entered by the user. For example, devices to measure sleep are known in the prior art. The user could record meals and snacks, as well as exercise. The data is analyzed in step 2304 to look for risks and suggestions for improvement. Comparisons with general norms and statistics of the user's demographic might be made. In some embodiments, the suggestions estimate quantified rewards for changing habits. For example, if the device has data that shows that the user generally has more energy for 50% of the day when they go to bed 30 minutes earlier, or burns 500 more calories throughout the afternoon if they work out in the morning, then the device can show the reward they get for one of those healthy behaviors. Tables of known data are preferably be consulted to ensure that promised rewards are reasonable.

Generally, when the device determines that there are no serious risks at decision point 2306 then the information is stored in a user-accessible database in step 2308. It could also be accessible to the user's doctor, insurance provider, both, or another trusted third party. Periodically or on request, the device suggests ways the user can improve health in step 2310. As discussed, estimated results from changes might be presented. In some embodiments, a wearer can use it to keep his physician apprised so that his physician knows if he has been compliant with what the physician has asked. However, when the device determines there is a serious and immediate health risk at 2306, then in step 2312 the device will immediately notify the user as well as predetermined third parties such as the user's doctor. In step 2314 the user's doctor and the user get an alert (e.g., a text message, an email, etc.) with a summary of the risk and a link to more information.

To help with overall health, sleep could also be tracked by an embodiment configured for a method similar to method 2300. Using ways to track sleep that are known in the art, such an embodiment could, for example, correlate sleep patterns with objective indicators, e.g., from retinal images, subjective reports, or both of how well the user is feeling. It could then estimate when and for how long the user should sleep and how dramatically it will affect the user's mood, health, and energy. Anything else that would regularly affect mood, health, and energy such as exercise, eating, and drinking, could be recorded, measured, or both. In some embodiments, Fitbit or similar health-tracking devices could be incorporated.

In any of the embodiments disclosed, tracking and analyzing habits and health indicators could not only benefit the user, but could also help advance medical science if shared.

Aspects of the systems and methods described herein are further described in U.S. Pat. Nos. 7,182,738 and 9,474,847, the entire disclosures of which are expressly incorporated herein by reference, including the contents and teachings of any references contained therein.

Embodiments described herein include the communication of data and/or signals among various components that are electrically and/or communicatively coupled. In an exemplary and non-limiting embodiment, the electrical and/or communicative couplings described herein are achieved via one or more communications networks capable of facilitating the exchange of data among various components the systems and/or devices described herein. For example, the one or more communications networks may include a wide area network (WAN) that is connectable to other telecommunications networks, including other WANs or portions of the Internet or an intranet, including local area networks (LANs) and/or personal area networks (PANs). The one or more communications networks may be any telecommunications network that facilitates the exchange of data, such as those that operate according to the IEEE 802.3 (e.g., Ethernet), the IEEE 802.11 (e.g., Wi-Fi™), and/or the IEEE 802.15 (e.g., Bluetooth®) protocols, for example. In another embodiment, the one or more communications networks are any medium that allows data to be physically transferred through serial or parallel communication channels (e.g., copper wire, optical fiber, computer bus, wireless communication channel, etc.).

In addition to the embodiments described above, embodiments of the present disclosure may comprise a special purpose computer including a variety of computer hardware, as described in greater detail below.

Embodiments within the scope of the present disclosure also include computer-readable media for carrying or having computer-executable instructions or data structures stored thereon. Such computer-readable media can be any available media that can be accessed by a special purpose computer. By way of example, and not limitation, computer-readable storage media include both volatile and nonvolatile, removable and non-removable media implemented in any method or technology for storage of information such as computer readable instructions, data structures, program modules or other data. Computer storage media are non-transitory and include, but are not limited to, random access memory (RAM), read only memory (ROM), electrically erasable programmable ROM (EEPROM), compact disk ROM (CD-ROM), digital versatile disks (DVD), or other optical disk storage, solid state drives (SSDs), magnetic cassettes, magnetic tape, magnetic disk storage, or other magnetic storage devices, or any other medium that can be used to carry or store desired program code means in the form of computer-executable instructions or data structures and that can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such connection is properly termed a computer-readable medium. Combinations of the above should also be included within the scope of computer-readable media. Computer-executable instructions comprise, for example, instructions and data which cause a general purpose computer, special purpose computer, or special purpose processing device to perform a certain function or group of functions.

The following discussion is intended to provide a brief, general description of a suitable computing environment in which aspects of the disclosure may be implemented. Although not required, aspects of the disclosure will be described in the general context of computer-executable instructions, such as program modules, being executed by computers in network environments. Generally, program modules include routines, programs, objects, components, data structures, etc. that perform particular tasks or implement particular abstract data types. Computer-executable instructions, associated data structures, and program modules represent examples of the program code means for executing steps of the methods disclosed herein. The particular sequence of such executable instructions or associated data structures represent examples of corresponding acts for implementing the functions described in such steps.

Those skilled in the art will appreciate that aspects of the disclosure may be practiced in network computing environments with many types of computer system configurations, including personal computers, hand-held devices, multiprocessor systems, microprocessor-based or programmable consumer electronics, network PCs, minicomputers, mainframe computers, and the like. Aspects of the disclosure may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing aspects of the disclosure includes a special purpose computing device in the form of a conventional computer, including a processing unit, a system memory, and a system bus that couples various system components including the system memory to the processing unit. The system bus may be any of several types of bus structures including a memory bus or memory controller, a peripheral bus, and a local bus using any of a variety of bus architectures. The system memory includes nonvolatile and volatile memory types. A basic input/output system (BIOS), containing the basic routines that help transfer information between elements within the computer, such as during start-up, may be stored in ROM. Further, the computer may include any device (e.g., computer, laptop, tablet, PDA, cell phone, mobile phone, a smart television, and the like) that is capable of receiving or transmitting an IP address wirelessly to or from the internet.

The computer may also include a magnetic hard disk drive for reading from and writing to a magnetic hard disk, a magnetic disk drive for reading from or writing to a removable magnetic disk, and an optical disk drive for reading from or writing to removable optical disk such as a CD-ROM or other optical media. The magnetic hard disk drive, magnetic disk drive, and optical disk drive are connected to the system bus by a hard disk drive interface, a magnetic disk drive-interface, and an optical drive interface, respectively. The drives and their associated computer-readable media provide nonvolatile storage of computer-executable instructions, data structures, program modules, and other data for the computer. Although the exemplary environment described herein employs a magnetic hard disk, a removable magnetic disk, and a removable optical disk, other types of computer readable media for storing data can be used, including magnetic cassettes, flash memory cards, digital video disks, Bernoulli cartridges, RAMs, ROMs, SSDs, and the like.

Communication media typically embody computer readable instructions, data structures, program modules or other data in a modulated data signal such as a carrier wave or other transport mechanism and includes any information delivery media.

One or more aspects of the disclosure may be embodied in computer-executable instructions (i.e., software), routines, or functions stored in system memory or nonvolatile memory as application programs, program modules, and/or program data. The software may alternatively be stored remotely, such as on a remote computer with remote application programs. Generally, program modules include routines, programs, objects, components, data structures, etc. that perform particular tasks or implement particular abstract data types when executed by a processor in a computer or other device. The computer executable instructions may be stored on one or more tangible, non-transitory computer readable media (e.g., hard disk, optical disk, removable storage media, solid state memory, RAM, etc.) and executed by one or more processors or other devices. As will be appreciated by one of skill in the art, the functionality of the program modules may be combined or distributed as desired in various embodiments. In addition, the functionality may be embodied in whole or in part in firmware or hardware equivalents such as integrated circuits, application specific integrated circuits, field programmable gate arrays (FPGA), and the like.

The computer may operate in a networked environment using logical connections to one or more remote computers. The remote computers may each be another personal computer, a tablet, a PDA, a server, a router, a network PC, a peer device, or other common network node, and typically include many or all of the elements described above relative to the computer. The logical connections include a local area network (LAN) and a wide area network (WAN) that are presented here by way of example and not limitation. Such networking environments are commonplace in office-wide or enterprise-wide computer networks, intranets and the Internet.

When used in a LAN networking environment, the computer is connected to the local network through a network interface or adapter. When used in a WAN networking environment, the computer may include a modem, a wireless link, or other means for establishing communications over the wide area network, such as the Internet. The modem, which may be internal or external, is connected to the system bus via the serial port interface. In a networked environment, program modules depicted relative to the computer, or portions thereof, may be stored in the remote memory storage device. It will be appreciated that the network connections shown are exemplary and other means of establishing communications over wide area network may be used.

Preferably, computer-executable instructions are stored in a memory, such as the hard disk drive, and executed by the computer. Advantageously, the computer processor has the capability to perform all operations (e.g., execute computer-executable instructions) in real-time.

The order of execution or performance of the operations in embodiments illustrated and described herein is not essential, unless otherwise specified. That is, the operations may be performed in any order, unless otherwise specified, and embodiments may include additional or fewer operations than those disclosed herein. For example, it is contemplated that executing or performing a particular operation before, contemporaneously with, or after another operation is within the scope of aspects of the disclosure.

Embodiments may be implemented with computer-executable instructions. The computer-executable instructions may be organized into one or more computer-executable components or modules. Aspects of the disclosure may be implemented with any number and organization of such components or modules. For example, aspects of the disclosure are not limited to the specific computer-executable instructions or the specific components or modules illustrated in the figures and described herein. Other embodiments may include different computer-executable instructions or components having more or less functionality than illustrated and described herein.

When introducing elements of aspects of the disclosure or the embodiments thereof, the articles "a", "an", "the" and "said" are intended to mean that there are one or more of the elements. The terms "comprising", "including", and "having" are intended to be inclusive and mean that there may be additional elements other than the listed elements.

Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

What is claimed is:

1. A system, comprising:
a plurality of sensors each configured to sense one or more physical properties of a user and to generate at least one signal representative thereof, wherein at least one of the plurality of sensors comprises a first sensor configured to be worn by the user and at least one of the plurality of sensors comprises a second sensor configured for use with an immersive technology system, wherein the one or more physical properties sensed by the first sensor comprises an activity level of the user, and wherein the one or more physical properties sensed by the second sensor comprises a physiological response of the user;
one or more processors; and
one or more non-transitory computer-readable media storing:
an artificial intelligence (AI) system configured to generate a regimen of activity parameters optimized or personalized to the user, the activity parameters each associated with an action taken on behalf of the user, wherein at least one of the activity parameters comprises a designated dosage of medication and at least one other of the activity parameters comprises stimuli for causing the physiological response sensed by the second sensor; and
instructions that, when executed by the one or more processors, configure the system to perform operations, the operations comprising:
receiving, by the AI system, data associated with the one or more physical properties via the signal from the plurality of sensors;
processing the received data with the AI system to monitor the one or more physical properties including at least the activity level and the physiological response of the user and to generate the regimen based thereon, wherein the generated regimen specifies adjusting the designated dosage of medication to be administered to the user based on the activity level and the physiological response thereof; and
providing the regimen as an output of the AI system to the immersive technology system, the immersive technology system generating an immersive environment in which the user performs the regimen, wherein the immersive environment presents the stimuli to the user causing the physiological response sensed by the second sensor.

2. The system of claim 1, further comprising a portable computing device in communication with the one or more processors and the sensors, the portable computing device configured to receive the signals from the sensors and to send the data associated with the one or more physical properties of the user to the one or more processors executing the AI system, wherein the portable computing device is configured to receive the regimen output by the AI system and present the regimen to the user via the portable computing device.

3. The system of claim 1, wherein the AI system is configured to store information relating to the monitored physical properties in the non-transitory computer-readable media.

4. The system of claim 1, wherein processing the received data comprises analyzing, by the AI system, the monitored physical properties to predict a biologic function of the user and/or determine a user's response to the activity parameters of the regimen.

5. The system of claim 1, wherein the AI system implements one or more of predictive learning, machine learning, automated planning and scheduling, machine perception, computer vision and affective computing to generate said activity parameters of the regimen optimized or personalized to the user.

6. The system of claim 1, wherein the activity level of the user is a state of sleep of the user, the AI system configured to access a medication schedule, and wherein the activity parameters of the regimen comprise a time for the user to take medicine based on the medication schedule and the state of sleep of the user.

7. The system of claim 1, wherein the activity level of the user is a state of sleep of the user, wherein the activity parameters of the regimen comprise a designated optimal time to activate an automated blood pressure measurement based on the state of sleep of the user.

8. The system of claim 1, wherein the activity parameters of the regimen comprise an optimal schedule for the user to perform at least one of the following activities: eating, sleeping, exercising, studying, working, rehabilitating, having intercourse, taking medications, reading for comprehension, concentrating, resting, socializing, calling, text messaging, and dieting.

9. The system of claim 1, wherein the activity parameters of the regimen comprise a designated optimal time for the user to undergo a medical procedure.

10. The system of claim 1, wherein the activity parameters of the regimen comprise a designated optimal diet for the user.

11. The system of claim 1, wherein the one or more physical properties of the user comprises at least one of the following in addition to the activity level of the user: biometric data, cellular data, biologic data, and non-biologic data.

12. The system of claim 1, wherein the one or more physical properties of the user comprises at least one of the following in addition to the activity level of the user: calories consumption, quality of sleep, activity, heart rhythm, pulse rate, blood pressure, temperature, perspiration, and blood chemistry.

13. The system of claim 1, wherein the AI system is configured to access a medication schedule, and wherein the activity parameters of the regimen comprise a time for the user to take medicine based on the medication schedule and the activity level of the user.

14. The system of claim 1, wherein the regimen comprises physical therapy performed using a therapy device, wherein the second sensor is coupled to the therapy device, and wherein the immersive technology system generates the immersive environment in which the user performs the physical therapy regimen using the therapy device.

15. The system of claim 1, wherein at least one of the plurality of sensors comprises a camera coupled to the immersive technology system for tracking motion of the user to monitor compliance with the regimen.

16. A method of generating a regimen of activity parameters optimized or personalized to a user, comprising:
receiving, by an artificial intelligence (AI) system, data associated with one or more physical properties of a user, wherein the data is received via a signal from a plurality of sensors each configured to sense the one or more physical properties of the user and to generate the signal representative thereof, wherein at least one of the plurality of sensors comprises a first sensor configured to be worn by the user and at least one of the plurality of sensors comprises a second sensor configured for use with an immersive technology system, wherein the one or more physical properties sensed by the first sensor comprises an activity level of the user, and wherein the one or more physical properties sensed by the second sensor comprises a physiological response of the user; and executing, by one or more processors, instructions stored on one or more non-transitory computer-readable media to configure the AI system to perform operations, the operations comprising:

processing the received data with the AI system to monitor the one or more physical properties including at least the activity level and the physiological response of the user and to generate the regimen based thereon, wherein the regimen comprises a plurality of activity parameters and at least one of the activity parameters comprises a designated dosage of medication and at least one other of the activity parameters comprises stimuli for causing the physiological response sensed by the second sensor, and wherein the generated regimen specifies adjusting the designated dosage of medication to be administered to the user based on the activity level and the physiological response thereof; and providing the regimen as an output of the AI system to the immersive technology system, the immersive technology system generating an immersive environment in which the user performs the regimen, the activity parameters of the regimen each associated with an action taken on behalf of the user, wherein the immersive environment presents the stimuli to the user causing the physiological response sensed by the second sensor.

17. The method of claim 16, wherein processing the received data comprises analyzing, by the AI system, the monitored physical properties to predict a biologic function of the user and/or determine a user's response to the activity parameters of the regimen.

18. The method of claim 16, wherein processing the received data with the AI system to generate the regimen comprises determining an optimal schedule for the user to perform at least one of the following activities: eating, sleeping, exercising, studying, working, rehabilitating, having intercourse, taking medications, reading for comprehension, concentrating, resting, socializing, calling, text messaging, and dieting.

19. The method of claim 16, wherein processing the received data with the AI system to generate the regimen comprises determining a designated optimal time for the user to undergo a medical procedure.

20. The method of claim 16, wherein processing the received data with the AI system to generate the regimen comprises determining a designated optimal diet for the user.

21. The method of claim 16, wherein the AI system is configured to access a medication schedule, and wherein processing the received data with the AI system to generate the regimen comprises determining a time for the user to take medicine based on the medication schedule and the activity level of the user.

22. The method of claim 16, wherein the regimen comprises physical therapy performed using a therapy device and wherein the second sensor is coupled to the therapy device, and further comprising generating, by the immersive technology system, the immersive environment in which the user performs the physical therapy regimen using the therapy device.

23. The method of claim 16, wherein at least one of the plurality of sensors comprises a camera coupled to the immersive technology system, and further comprising tracking motion of the user with the camera to monitor compliance with the regimen.

\* \* \* \* \*